(12) United States Patent
Goldstein et al.

(10) Patent No.: US 8,962,622 B2
(45) Date of Patent: Feb. 24, 2015

(54) BENZOTRIAZOLE KINASE MODULATORS

(75) Inventors: David Michael Goldstein, San Jose, CA (US); Levi Gong, San Mateo, CA (US); Christophe Michoud, New York, NY (US); Wylie Solang Palmer, Mountain View, CA (US); Achyutharao Sidduri, Livingston, NJ (US)

(73) Assignee: Roche Palo Alto LLC, Palo Alto, CA (US)

( * ) Notice: Subject to any disclaimer, the term of this patent is extended or adjusted under 35 U.S.C. 154(b) by 1767 days.

(21) Appl. No.: 11/899,758

(22) Filed: Sep. 7, 2007

(65) Prior Publication Data

US 2008/0103142 A1 May 1, 2008

Related U.S. Application Data

(60) Provisional application No. 60/843,090, filed on Sep. 8, 2006.

(51) Int. Cl.
*C07D 403/04* (2006.01)
*A61K 31/505* (2006.01)
*C07D 403/14* (2006.01)

(52) U.S. Cl.
CPC ............ *C07D 403/04* (2013.01); *C07D 403/14* (2013.01)
USPC ................... 514/235.8; 514/252.19; 514/275; 544/122; 544/295; 544/296; 544/324

(58) Field of Classification Search
USPC ............... 544/122, 295, 296, 324; 514/235.8, 514/252.19, 275
See application file for complete search history.

(56) References Cited

U.S. PATENT DOCUMENTS 6,498,165 B1   12/2002   Armstrong et al.

FOREIGN PATENT DOCUMENTS

| EP | 2004625 | 12/2008 |
|---|---|---|
| WO | WO 01/00207 A1 | 1/2001 |
| WO | WO 01/00213 A1 | 1/2001 |
| WO | WO 01/60816 A1 | 8/2001 |
| WO | WO 2004/005283 A1 | 1/2004 |
| WO | WO 2004/089913 A1 | 10/2004 |
| WO | 2005/123719 | 12/2005 |
| WO | WO 2006/038001 A1 | 4/2006 |
| WO | WO 2006/075152 A1 | 7/2006 |
| WO | 2006/135644 | 12/2006 |

OTHER PUBLICATIONS

Fabbro et al., Protein kinases as targets for anticancer agents: from inhibitors to useful drugs, Pharmacology & Therapeutics, 93, pp. 79-98, 2002.*
Traxler, Protein tyrosine kinase inhibitors in cancer treatment, Exp. Opin. Ther. Patents, 7(6), pp. 571-588, 1997.*
Layzer, Degenerative diseases of the nervous system, Cecil Textbook of Medicine, 20th Edition, vol. 2, pp. 2050-2057, 1996.*
Damasio, Alzheimer's Disease and related dementias, Cecil Textbook of Medicine, 20th Edition, vol. 2, pp. 1992-1996, 1996.*
Simone, Oncology: Introduction, 20$^{th}$ Edition, vol. 1, pp. 1004-1010, 1996.*
Gompper et al., Chemistry and Nonlinear Optical Properties of New 2H-Benzotriazole Derivatives, Tetrahedron, vol. 52, No. 46, pp. 14607-14624, 1996.*
Bradley, B. L., et. al. "Eosinophils, T-lymphocytes, mast cells, neutrophils, and macrophages in bronchial biopsy specimens from atopic subjects with asthma: Comparison with biopsy specimens from atopic subjects without asthma and normal control subjects and relationship to bronchial hyperresponsiveness," *Journal of Allergy Clin. Immunology* 1991, vol. 88, pp. 661-674.
Derijard, B., et. al. "JNK1: A Protein Kinase Stimulated by UV Light and Ha-Ras That Binds and Phosphorylates the c-Jun Activation Domain," *Cell*, 1994, vol. 76, pp. 1025-1037.
Han, Z., et. al., "Joint Damage and Inflammation in c-Jun N-Terminal Kinase 2 Knockout Mice With Passive Murine Collagen-Induced Arthritis," *Arthritis & Rheumatism*, 2002, vol. 46 (3), pp. 818-823.
Han, Z., et. al., "c-Jun N-terminal kinase is required for metalloproteinase expression and joint destruction in inflammatory arthritis," *J. Clinical Investigation*, 2001 vol. 108 (1), pp. 73-81.
Ip, Y. T., et. al., "Signal transduction by the c-Jun N-terminal kinase (JNK)—from inflammation to development," *Current Opinion Cell Biology*, 1998, vol. 10, pp. 205-219.
Jaeschke, A, et. al. "Disruption of the Jnk2 (Mapk9) gene reduces destructive insulitis and diabetes in a mouse model of type 1 diabetes," *PNAS*, 2005, vol. 102 (19), pp. 6931-6935.
Lee, Y. H., et. al. "c-Jun N-terminal Kinase (JNK) Mediates Feedback Inhibition of the Insulin Signaling Cascade*" *Journal of Biological Chemistry*, 2003, vol. 278 (5), pp. 2896-2902.
Manning, A. M., et. al., "Targeting JNK for Therapeutic Benefit: From Junk to Gold?" *Nature* 2003, vol. 2, pp. 554-565.
Nakatani, Y., et. al. "Modulation of the JNK Pathway in Liver Affects Insulin Resistance Status*" *Journal of Biological Chemistry*, 2004, vol. 279 (44), pp. 45803-45809.
Schett, G., et. al., "Activation, Differential Localization, and Regulation of the Stress-Activated Protein kinases, Extracellular Signal-Regulated Kinase, c-Jun N-Terminal Kinase, and p38 Mitogen-Activated Protein Kinase, in Synovial Tissue and Cells in Rheumatoid Arthritis," *Arthritis & Rheumatism*, 2000, vol. 43 (11), pp. 2501-2512.

(Continued)

Primary Examiner — Deepak Rao

(57) ABSTRACT

Compounds of formula I modulate jnk and cdk:

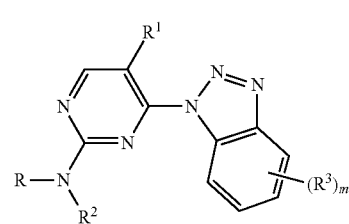

or a pharmaceutically acceptable salt thereof, where R, $R^1$, $R^2$, $R^3$, and m are defined herein.

32 Claims, No Drawings

(56) References Cited

OTHER PUBLICATIONS

Stebbins, J. L., et. al., Identification of a new JNK Inhibitor Targeting the JNK-JIP interaction site, *PNAS*, 2008, vol. 105 (43), pp. 16809-16813.

Yang, D. D., et. al., Absence of excitotoxicity-induced apoptosis in the hippocampus of mice lacking the Jnk3 gene, *Nature*, 1997, vol. 389, pp. 865-870.

Yasuda, J., et. al., "The JIP Group of Mitogen-Activated Protein Kinase Scaffold Proteins," *Molecular and Cellular Biology*, 1999, vol. 19 (10), pp. 7245-7254.

Antonyak, M. A., et. al. "Elevated JNK activation contributes to the pathogenesis of human brain tumors," *Oncogene* 2002, vol. 21, pp. 5038-5046.

Bennett, B. L., et. al. "JNK: a new therapeutic target for diabetes," *Current Opinion in Pharma.*, 2003, vol. 3, pp. 420-425.

Blease, K., et. al. "Emerging Treatment for Asthma," *Expert. Opin. Emerging Drugs*, 2003, vol. 8 (1), pp. 73-81.

Bousquet, J., et. al. "Asthma from Bronchoconstriction to Airways Inflammation and Remodeling," *American J. Respiratory and Critical Care Med.* 2000, vol. 161, pp. 1720-1745.

Bozyczko-Coyne, D., et. al. "Targeting the JNK Pathway for Therapeutic Benefit in CNS Disease," *Current Drug Target*, 2002, vol. 1, pp. 31-49.

Cripe, L.D., et. al. "Role for c-jun N-terminal kinase in treatment-refractory acute myeloid leukemia (AML): signaling to multidrug-efflux and hyperproliferation," *Leukemia*, 2002, vol. 16, pp. 799-812.

Eynott, P. R., et. al. "Allergen-induced inflammation and airway epithelial and smooth muscle cell proliferation: role of Jun N-terminal kinase," *British J. Pharmacology*, 2003, vol. 140, pp. 1373-1380.

Hess, P., et. al. "Survival signaling mediated by c-Jun NH2-terminal kinase in transformed B lymphoblasts," *Nature Genetics* 2002, vol. 32, pp. 201-205.

Hirosumi, J., et. al. "A Central Role for JNK in Obesity and Insulin Resistance," *Nature*, 2002, vol. 420, pp. 333-336.

Kaneto, H., et. al. "Possible novel therapy for diabetes with cell-permeable JNK-inhibitory peptide," *Nature Medicine* 2004, vol. 10 (10), pp. 1128-1132.

Kaneto, H., et. al "The JNK pathway as a therapeutic target for diabetes," *Expert Opin. Ther. Targets*, 2005, vol. 9 (3), pp. 581-592.

Nath, P., et. al. "Potential role of c-Jun NH2-terminal kinase in allergic airway inflammation and remodeling: effects of SP600125," *European J. Pharmacology*, 2005, vol. 506, pp. 273-283.

Pei, J., et. al. "Localization of active forms of C-jun kinase (JNK) and p38 kinase in Alzheimer's disease brains at different stages of neurofibrillary degeneration," *J. Alzheimer's Disease*, 2001, vol. 3, pp. 41-48.

Saporito, M. S., et. al. "MPTP Activates c-Jun NH2-Terminal Kiinase (JNK) and Its Upstream Regulatory Kinase MKK4 in Nigrostriatal Neurons In Vivo," *J. Neurochemistry*, 2000, vol. 75 (3), pp. 1200-1208.

Xia, X. G., et. al. "Gene transfer of the JNK interacting protein-1 protects dopaminergic neurons in the MPTP model of Parkinson's disease," *PNAS*, 2001, vol. 98 (18), pp. 10433-10438.

Chilean Office Action in related case 2572-2007.

(Translation of Jap Off Act in Corres Jap Appl 2009527118 Jun. 12, 2012).

\* cited by examiner

BENZOTRIAZOLE KINASE MODULATORS

RELATED APPLICATIONS

This application claims priority from U.S. Ser. No. 60/843,090, filed Sep. 8, 2006, incorporated herein by reference in full.

FIELD OF THE INVENTION

The present invention relates to a method for modulating c-Jun N-terminal kinases (JNK) and cyclin-dependent kinases (CDK), and a method for treating a subject afflicted with a disease or condition that can be alleviated by modulating JNKs or CDKs with heterocyclic compounds, more particularly, to benzotriazole derivatives. The invention further relates to novel heterocyclic compounds and pharmaceutical compositions comprising said compound.

BACKGROUND OF THE INVENTION

The c-Jun N-terminal kinases (JNKs) are members of mitogen-activated protein kinase family along with p38 and extracellular signal-regulated kinases (ERKs). Three distinct genes (jnk1, jnk2 and jnk3) encoding 10 splice variants have been identified (Y. T. Ip and R. J. Davis, *Curr. Opin. Cell Biol.* (1998) 10:205-19). JNK1 and JNK2 are expressed in a wide variety of tissues, whereas JNK3 is mainly expressed in neurons, and to a lesser extent in heart and testes (D. D. Yang et al., *Nature* (1997) 389:865-70). Members of JNK family are activated by pro-inflammatory cytokines such as tumor necrosis factor α (TNF-α) and interleukin-1β (IL-β), as well as environmental stresses. The activation of JNKs is mediated by its upstream kinases, MKK4 and MKK7, via dual phosphorylation of Thr-183 and Tyr-185 (B. Derijard et al., *Cell* (1994) 76:1025-37). It has been shown that MKK4 and MMK7 can be activated by the diverse upstream kinases, including MEKK1 and MEKK4, depending upon the external stimuli and cellular context (D. Boyle et al., *Arthritis Rheum* (2003) 48:2450-24). The specificity of JNK signaling is achieved by forming a JNK-specific signaling complex containing multiple components of the kinase cascade using scaffold proteins called JNK-interacting proteins (J. Yasuda et al., *Mol. Cell. Biol.* (1999) 19:7245-54). JNKs have been shown to play important roles in inflammation, T cell functions, apoptosis and cellular survival by phosphorylating specific substrates, including transcription factors such as c-Jun, the component of activator protein-1 (API) family, and ATF2, as well as non-transcription factors such as IRS-1 and Bcl-2 (A. M. Manning and R. J. Davis, *Nat. Rev. Drug Discov.* (2003) 2:554-65). Over-activation of JNK is believed to be an important mechanism in autoimmune, inflammatory, metabolic, neurological diseases as well as cancer.

Rheumatoid arthritis (RA) is a systemic autoimmune disease characterized by chronic inflammation of the joints. In addition to the joint swelling and pain caused by the inflammatory process, most RA patients ultimately develop debilitating joint damage and deformation. Several lines of compelling pharmacological and genetic evidence in cellular and animal models strongly suggest the relevance and importance of the activated JNK in the pathogenesis of RA. First, abnormal activation of JNK was detected in both human arthritic joints from RA patients (G. Schett et al., *Arthritis Rheum* (2000) 43:2501-12) and rodent arthritic joints from animal models of arthritis (Z. Han et al., *J. Clin. Invest.* (2001) 108:73-81). In addition, inhibition of JNK activation by selective JNK inhibitors blocked proinflammatory cytokines and MMP production in human synoviocytes, macrophages and lymphocytes (Z. Han et al., (2001) supra). Importantly, administration of the selective JNK inhibitors in rats with adjuvant arthritis (Z. Han et al., (2001) supra) or in mice with collagen-induced arthritis (P. Gaillard et al., *J Med. Chem.* (2005) 14:4596-607) effectively protected joints from destruction and significantly reduced paw swelling by inhibiting cytokine and collagenase expression. Furthermore, JNK2 deficient mice were partially protected from joint destruction, but showed little effect on paw swelling and inflammation in the passive collagen-induced arthritis model. These studies indicate that JNK2 is functionally redundant with JNK1 in regard to their roles in matrix degradation, inflammation and paw swelling. Therefore, combined inhibition of both JNK1 and JNK2 activities is required for effective therapy for RA (Z. Han et al., *Arthritis Rheum.* (2002) 46:818-23).

Asthma is a chronic inflammatory disease of airways, characterized by the presence of a cellular inflammatory process and by bronchial hyper-responsiveness associated with structural changes of the airways (B. Bradley et al., *J. Allergy Clin. Immunol.* (1991) 88:661-74). This disorder has been shown to be driven by many cell types in the airways, including T lymphocytes, eosinophils, mast cells, neutrophils and epithelial cells (J. Bousquet et al., *Am. J. Respir. Crit. Care Med.* (2000) 161:1720-45). JNKs have emerged as promising therapeutic targets for asthma based upon the recent proof-of-concept studies in the cellular and animal models of asthma using selective JNK inhibitors (K. Blease et al., *Expert Opin. Emerg. Drugs* (2003) 8:71-81). It was shown that JNK inhibitors significantly blocked RANTES production in activated human airway smooth cells (K. Kujime et al., *J. Immunol.* (2000) 164:3222-28). More importantly, the JNK inhibitors showed good efficacy in chronic rat and mouse models for their abilities to reduce cellular infiltration, inflammation, hyper-responsiveness, smooth muscle proliferation, and IgE production (P. Nath et al., *Eur. J. Pharmacol.* (2005) 506:273-83; P. Eynott et al., *Br. J. Pharmacol.* (2003) 140:1373-80). These observations suggest important roles of JNKs in the allergic inflammation, airway remodeling process associated with hyper-responsiveness. Therefore, blockade of JNK activity is expected to be beneficial for the treatment of asthma.

Type 2 diabetes is the most serious and prevalent metabolic disease characterized by insulin resistance and insulin secretion impairment as a result of chronic low-level inflammation and abnormal lipid metabolism associated with oxidative stress. It has been reported that JNK activity is abnormally elevated in various diabetic target tissues under obese and diabetic conditions (J. Hirosumi et al., *Nature* (2002) 420:333-36; H. Kaneto, *Expert. Opin. Ther. Targets* (2005) 9:581-92). Activation of the JNK pathway by pro-inflammatory cytokines and oxidative stresses negatively regulates insulin signaling via phosphorylation of insulin receptor substrate-1 (IRS-1) at $Ser^{307}$, therefore contributes to insulin resistance and glucose tolerance (J. Hirosumi et al., *Nature* (2002) supra; Y. Lee et al., *J. Biol. Chem.* (2003) 278:2896-902; Y. Nakatani et al., *J. Biol. Chem.* (2004) 279:45803-09). Compelling genetic evidence came from elegant animal model studies using $jnk^{-/-}$ mice crossed with either genetic (ob/ob) obese mice or dietary obese mice. Loss of JNK1($JNK1^{-/-}$), but not JNK2 functions ($jnk^{-/-}$), protected obese mice from body gains, increased steady-state levels of blood glucose, and decreased plasma insulin levels (J. Hirosumi et al., *Nature* (2002) supra). Furthermore, the beneficial effects were observed in a genetic diabetic model (db/db mice) by administration of either a small molecule JNK inhibitor, CC105 (B. Bennett et al., *Curr. Opin. Pharmacol.* (2003) 3:420-25) or a JNK inhibitory peptide I(JIP) derived from the JNK binding domain of the JNK-interacting protein-1 (JIP-1) (H. Kaneto et al., *Nat. Med.* (2004) 10:1128-32), including significant lower blood glucose and higher plasma insulin levels. More interestingly, another recent report (A. Jaeschke et al., *Proc. Natl. Acad. Sci. USA*. (2005) 102:6931-35) revealed that JNK2 plays an important role in type I diabetes caused by autoimmune destruction of insulin-producing β cells. Non-obese diabetic mice deficient in JNK2 expression showed reduced destructive insulitis and less disease progression to diabetes, probably due to biased polarization toward the Th2 phenotype. Taken together, these studies demonstrated the utility of JNK inhibitors in the treatment of obesity/type 2 diabetes.

Neurodegenerative diseases, such as Alzheimer's (AD), Parkinson's (PD) and stroke are characterized by synaptic loss, neuronal atrophy and death. The JNK pathway leading to c-Jun activation has been shown to play a causal role in apoptosis of isolated primary embryonic neurons and multiple neuronal cell lines upon induction of a variety of stimuli (D. Bozyczko-Coyne et al., *Curr. Drug Targets CNS Neurol. Disord.* (2002) 1:31-49). Over-activation of JNK was observed in human brains from AD patients (J. Pei et al., *J. Alzheimers Dis.* (2001) 3:41-48) or rodent brain sections derived from animal models of neurodegenerative diseases (M. Saporito et al., *J. Neurochem.* (2000) 75:1200-08). For example, increased phospho-JNKs were detected in the postmortem brains from the AD patients. Administration of JNK inhibitory peptide (JIP-1 peptide) in the rodent model of AD induced by β-amyloid peptide administration prevented the impairment of synaptic plasticity. In the animal models of PD (MPTP model), elevated phospho-MKK4 and phospho-JNKs were observed concomitantly with the neuronal cell death. Adenoviral gene transfer of JNK inhibitory peptide (JIP-1 peptide) into striatum of mice attenuated behavioral impairment by inhibiting MPTP-mediated JNK, c-Jun and caspase activation, therefore blocking neuronal cell death in the substantia nigra (X. Xia et al., *Proc. Natl. Acad. Sci. USA*. (2001) 98:10433-38). In addition, in the animal model of ischemic stroke induced by glutamate excitotoxicity, mice deficient in JNK3, but not JNK1 or JNK2, were resistant to kainic acid (glutamate receptor agonist)-mediated seizure or neuronal death (D. D. Yang et al., *Nature* (1997) 389:865-70). These data suggest JNK3 was mainly responsible for glutamate excitotoxicity, an important component in ischemic conditions. Taken together, the data suggests that JNKs are an attractive target for multiple CNS diseases associated with neuronal cell death.

Uncontrolled cellular growth, proliferation and migration along with de-regulated angiogenesis lead to the formation of malignant tumors. The JNK signal transduction pathway may not act exclusively in apoptosis, sustained JNK activation leading to AP1 activation has recently been implicated to contribute to the cellular survival of specific cancer types such as glial tumors and BCL-ABL transformed B lymphoblasts (M. Antonyak et al., *Oncogene* (2002) 21:5038-46; P. Hess et al., Nat. Genet. (2002) 32:201-05). In the case of glial tumors, enhanced JNK/AP1 activity was seen in most of the primary brain tumor samples. For the transformed B lymphoblasts, BCL-ABL was shown to activate the JNK pathway which in turn up-regulated expression of anti-apoptotic bcl-2 gene. Interestingly, the multi-drug resistance and hyper-proliferation seen in treatment-refractory AML patients has been causally linked to the sustained JNK activity present in these AML samples (L. Cripe et al., *Leukemia* (2002) 16:799-812). Activation of JNK in leukemic cells resulted in induced expression of efflux pumps such as mdr1 and MRP1 responsible for multidrug resistance. Also, genes with a survival benefit in response to oxidative stress including glutathione-S-transferase π and γ-glutamyl cysteine synthase were also upregulated by the activated JNK pathway.

Accordingly, JNK modulators are useful in treating a variety of diseases and/or conditions.

The role of cyclin-dependent kinases ("cdks") in the regulation of cellular proliferation is well established. There is an extensive body of literature validating the use of compounds that inhibit targets in the Cdk4, Cdk2 and Cdk1 pathways as anti-proliferative therapeutic agents. See, e.g., J. Lukas et al., *Nature* (1995) 79:573-82; J. R. Nevins, *Science* (1992) 258: 424-29; I. K. Lim et al., *Mol Carcinogen* (1998) 23:25-35; S. W. Tam et al., *Oncogene* (1994) 9:2663-74; B. Driscoll et al., *Am. J. Physiol.* (1997) 273 (*Lung Cell. Mol. Physiol.*) L941-L949; and J. Sang et al., *Chin. Sci. Bull.* (1999) 44:541-44. Inhibitors of cellular proliferation act as reversible cytostatic agents that are useful in the treatment of disease processes which feature abnormal cellular growth, such as cancers and other cell proliferative disorders including, for example inflammation (e.g. benign prostate hyperplasia, familial adenomauosis, polyposis, neuro-fibromatosis, atherosclerosis, pulmonary fibrosis, arthritis, psoriasis, inflammatory bowel disease, transplantation rejections infections), viral infections (including, without limitation, herpesvirus, poxvirus, Epstein-Barr virus), autoimmune disease (e.g. lupus, rheumatoid arthritis, psoriasis, inflammatory bowel disease), neurodegenerative disorders (including, without limitation, Alzheimer's disease), and neurodegenerative diseases (e.g. Parkinson's disease, amyotrophic lateral sclerosis, retinitis pigmentosa, spinal muscular atrophy, and cerebral degeneration).

SUMMARY OF THE INVENTION

One aspect of the invention provides a compound of formula I:

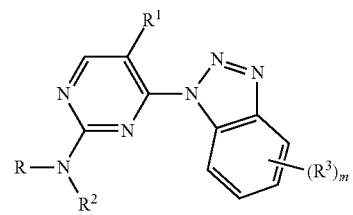

or a pharmaceutically acceptable salt thereof,
wherein
R is lower alkyl, hydroxy lower alkyl, or a radical selected from:

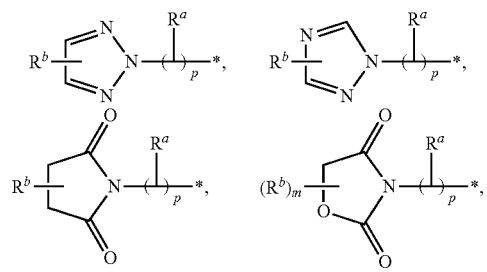

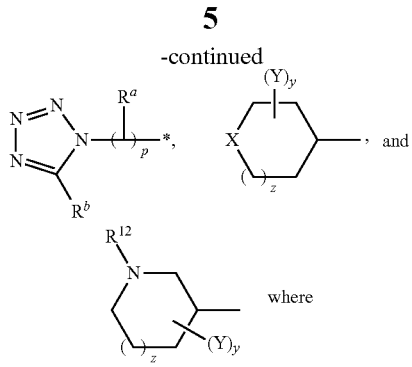

each $R^a$ is independently H, lower alkyl, OH, or hydroxy-lower alkyl;
each $R^b$ is independently H, lower alkyl, halo, nitro, or halo-lower alkyl;
p is 1, 2, 3, or 4;
X is O, $CR^4R^5$, C(=O), or $S(O)_x$;
$R^1$ is hydrogen, halo, alkyl, or $NH_2$;
each of $R^3$ is independently halo, —$NO_2$, lower alkyl, —CN, —$OR^7$, —$NR^8R^9$, —C(O)—$R^7$, —O—C(O)—$R^7$, —$CF_3$, —$CHF_2$, —$SO_2$—$R^{10}$, or two of $R^3$ form alkylene dioxy;
$R^4$ is hydrogen, lower alkyl, cyano, —$(CH_2)_nOR^7$, —$(CH_2)_nNR^8R^9$, —$(CH_2)_n$—C(O)$NR^8R^9$, —$(CH_2)_n$—OC(O)—$NR^8R^9$, —$(CH_2)_n$—$C(O)OR^7$; —$NR^7$—$SO_2$—$R^{10}$, —$(CH_2)_n$—$NR^8$—C(O)—$R^{11}$, or —$(CH_2)_n$—$NR^8$—C(O)—$OR^6$;
$R^5$ is hydrogen or alkyl;
or $R^4$ and $R^5$ together form alkylene dioxy;
$R^6$ is hydrogen, lower alkyl, heteroalkyl, cycloalkyl, heterocyclylalkyl, or —$NR^8R^9$;
$R^{10}$ is alkyl, cycloalkyl, heterocyclylalkyl, or —$NR^8R^9$;
$R^{11}$ is alkyl, cycloalkyl, heteroalkyl, or (heterocyclyl)alkyl;
$R^2$ and $R^7$ are each independently hydrogen, lower alkyl, hydroxyalkyl, or cycloalkyl;
$R^8$ is hydrogen, lower alkyl, or acyl;
$R^9$ is hydrogen, lower alkyl, heteroalkyl, aryl, heteroaryl, heterocyclyl, cycloalkyl;
or $R^8$ and $R^9$ together with the nitrogen atom to which they are connected to form a heterocyclyl comprising at least one nitrogen ring atom, optionally substituted with OH, oxo, lower alkyl, lower alkoxy, or acyl;
$R^{12}$ is H, lower alkyl, cycloalkyl, —C(O)—$R^7$, —$SO_2$—$R^{11}$;
each of m and x is independently an integer from 0 to 2;
Y is hydrogen, —$(CH_2)_n$—$OR^7$, —$(CH_2)_n$—C(O)—$R^7$ or —$(CH_2)_n$—$C(O)OR^7$;
each of y and z is independently 0 or 1; and
n is an integer from 0 to 4.

The invention also provides pharmaceutical compositions, methods of using, and methods of preparing the aforementioned compounds.

Compounds and compositions of the invention are useful in the treatment and/or prevention of a c-Jun N-terminal kinase mediated disorder, such as autoimmune disorders, inflammatory disorders, metabolic disorders, neurological diseases, and cancer. In some embodiments, compounds and compositions of the invention are useful in treating and/or preventing rheumatoid arthritis, asthma, type II diabetes, Alzheimer's disease, Parkinson's disease and/or stroke.

Compounds and compositions of the invention are useful in the treatment and/or prevention of a CDK mediated disorder, which are generally disease processes which feature abnormal cellular growth, such as cancers and other cell proliferative disorders including, for example inflammation (e.g. benign prostate hyperplasia, familial adenomauosis, polyposis, neuro-fibromatosis, atherosclerosis, pulmonary fibrosis, arthritis, psoriasis, inflammatory bowel disease, transplantation rejections infections), viral infections (including, without limitation, herpesvirus, poxvirus, Epstein-Barr virus), autoimmune disease (e.g. lupus, rheumatoid arthritis, psoriasis, inflammatory bowel disease), neurodegenerative disorders (including, without limitation, Alzheimer's disease), and neurodegenerative diseases (e.g. Parkinson's disease, amyotrophic lateral sclerosis, retinitis pigmentosa, spinal muscular atrophy, and cerebral degeneration).

DETAILED DESCRIPTION OF THE INVENTION

Definitions

Unless otherwise stated, the following terms used in this application, including the specification and claims, have the definitions given below. It must be noted that, as used in the specification and the appended claims, the singular forms "a", "an," and "the" include plural referents unless the context clearly dictates otherwise.

"Alkyl" means the monovalent linear or branched saturated hydrocarbon moiety, consisting solely of carbon and hydrogen atoms, having from one to twelve carbon atoms. "Lower alkyl" refers to an alkyl group of one to six carbon atoms, i.e. $C_1$-$C_6$ alkyl. Examples of alkyl groups include, but are not limited to, methyl, ethyl, propyl, isopropyl, isobutyl, sec-butyl, tert-butyl, pentyl, n-hexyl, octyl, dodecyl, and the like. "Branched alkyl" refers to an alkyl moiety having at least one branch, for example, isopropyl, isobutyl, tert-butyl, and the like. Similarly, "lower alkoxy" refers to a moiety of the form —OR, and "acyl" refers to a moiety of the form —C(O)R, where R is lower alkyl.

"Alkylene" means a linear saturated divalent hydrocarbon moiety of one to six carbon atoms or a branched saturated divalent hydrocarbon radical of three to six carbon atoms, e.g., methylene, ethylene, 2,2-dimethylethylene, propylene, 2-methylpropylene, butylene, pentylene, and the like.

"Alkylene dioxy" means a divalent moiety of the formula —O—R—O—, where R is alkylene as defined herein.

"Aryl" means a monovalent cyclic aromatic hydrocarbon moiety consisting of a mono-, bi- or tricyclic aromatic ring. The aryl group can be optionally substituted as defined herein. Examples of aryl moieties include, but are not limited to, optionally substituted phenyl, naphthyl, phenanthryl, fluorenyl, indenyl, pentalenyl, azulenyl, oxydiphenyl, biphenyl, methylenediphenyl, aminodiphenyl, diphenylsulfidyl, diphenylsulfonyl, diphenylisopropylidenyl, benzodioxanyl, benzofuranyl, benzodioxylyl, benzopyranyl, benzoxazinyl, benzoxazinonyl, benzopiperadinyl, benzopiperazinyl, benzopyrrolidinyl, benzomorpholinyl, methylenedioxyphenyl, ethylenedioxy-phenyl, and the like, including partially hydrogenated derivatives thereof.

"Cycloalkyl" means a monovalent saturated carbocyclic moiety consisting of mono- or bicyclic rings. Cycloalkyl can optionally be substituted with one or more substituents, wherein each substituent is independently hydroxy, alkyl, alkoxy, halo, haloalkyl, amino, monoalkyl-amino, or dialkylamino, unless otherwise specifically indicated. Examples of cycloalkyl moieties include, but are not limited to, cyclopropyl, cyclobutyl, cyclopentyl, cyclohexyl, cycloheptyl, and the like, including partially unsaturated derivatives thereof.

"Cycloalkylalkyl" mean a moiety of the formula —$R^a$—$R^b$, where $R^a$ is alkylene and $R^b$ is cycloalkyl as defined herein.

"Heteroalkyl" means an alkyl moiety as defined herein, including a branched $C_4$-$C_7$ alkyl, wherein one, two or three hydrogen atoms have been replaced with a substituent independently selected from the group consisting of —$OR^a$, —$NR^bR^c$, and —$S(O)R^d$ (where n is an integer from 0 to 2), with the understanding that the point of attachment of the heteroalkyl radical is through a carbon atom, wherein $R^a$ is hydrogen, acyl, alkyl, cycloalkyl, or cycloalkylalkyl; $R^b$ and $R^c$ are independently of each other hydrogen, acyl, alkyl, cycloalkyl, or cycloalkylalkyl; and when n is 0, $R^d$ is hydrogen, alkyl, cycloalkyl, or cycloalkylalkyl; when n is 1, $R^d$ is alkyl, cycloalkyl, or cycloalkylalkyl; and when n is 2, $R^d$ is alkyl, cycloalkyl, cycloalkylalkyl, amino, acylamino, monoalkylamino, or dialkylamino. Representative examples include, but are not limited to, 2-hydroxyethyl, 3-hydroxypropyl, 2-hydroxy-1-hydroxymethylethyl, 2,3-dihydroxypropyl, 1-hydroxymethylethyl, 3-hydroxybutyl, 2,3-dihydroxybutyl, 2-hydroxy-1-methylpropyl, 2-aminoethyl, 3-aminopropyl, 2-methylsulfonylethyl, aminosulfonylmethyl, aminosulfonylethyl, aminosulfonylpropyl, methylaminosulfonylmethyl, methylaminosulfonylethyl, methylaminosulfonylpropyl, and the like.

"Heteroaryl" means a monocyclic or bicyclic moiety of 5 to 12 ring atoms having at least one aromatic ring containing one, two, or three ring heteroatoms selected from N, O, or S, the remaining ring atoms being C, with the understanding that the attachment point of the heteroaryl radical will be on an aromatic ring. The heteroaryl ring may be optionally substituted as defined herein. Examples of heteroaryl moieties include, but are not limited to, optionally substituted imidazolyl, oxazolyl, isoxazolyl, thiazolyl, isothiazolyl, oxadiazolyl, thiadiazolyl, pyrazinyl, thienyl, thiophenyl, furanyl, pyranyl, pyridinyl, pyrrolyl, pyrazolyl, pyrimidyl, pyridazinyl, quinolinyl, isoquinolinyl, benzofuryl, benzofuranyl, benzothiophenyl, benzothiopyranyl, benzimidazolyl, benzoxazolyl, benzooxadiazolyl, benzothiazolyl, benzothiadiazolyl, benzo-pyranyl, indolyl, isoindolyl, indazolyl, triazolyl, triazinyl, quinoxalinyl, purinyl, quinazolinyl, quinolizinyl, naphthyridinyl, pteridinyl, carbazolyl, azepinyl, diazepinyl, acridinyl and the like, including partially hydrogenated derivatives thereof.

The terms "halo," "halogen," and "halide" are used interchangeably herein and refer to a substituent fluoro, chloro, bromo, or iodo.

"Haloalkyl" means alkyl as defined herein in which one or more hydrogen has been replaced with same or different halogen. Exemplary haloalkyls include —$CH_2Cl$, —$CH_2CF_3$, —$CH_2CCl_3$, perfluoroalkyl (e.g., —$CF_3$), and the like.

"Heterocyclyl" means a monovalent saturated moiety, consisting of one to three rings, incorporating one, two, or three or four heteroatoms (chosen from nitrogen, oxygen or sulfur). The heterocyclyl ring may be optionally substituted as defined herein. Examples of heterocyclyl moieties include, but are not limited to, optionally substituted piperidinyl, piperazinyl, homo-piperazinyl, azepinyl, pyrrolidinyl, pyrazolidinyl, imidazolinyl, imidazolidinyl, pyridinyl, pyridazinyl, pyrimidinyl, oxazolidinyl, isoxazolidinyl, morpholinyl, thiazolidinyl, isothiazol-idinyl, quinuclidinyl, quinolinyl, isoquinolinyl, benzimidazolyl, thiadiazolylidinyl, benzo-thiazolidinyl, benzoazolylidinyl, dihydrofuryl, tetrahydrofuryl, dihydropyranyl, tetrahydro-pyranyl, thiamorpholinyl, thiamorpholinylsulfoxide, thiamorpholinylsulfone, dihydroquinolinyl, dihydroisoquinolinyl, tetrahydroquinolinyl, tetrahydrisoquinolinyl, and the like.

"Optionally substituted", when used in association with "aryl", "phenyl", "heteroaryl" or "heterocyclyl", means an aryl, phenyl, heteroaryl or heterocyclyl which is optionally substituted independently with one or more substituents, preferably one to four, and more preferably, one to three substituents selected from $C_{1-6}$ alkyl, $C_{1-6}$ heteroalkyl, oxo (i.e., =O), haloalkyl, —$(CH_2)_mCOX^1$, —$(CH_2)_mSO_2X^2$, $C_{1-6}$ alkoxy, halogen, $C_{1-6}$ alkylthio, $C_{1-6}$ alkylsulfonyl, —$SO_2NR^4R^5$, cyano, nitro, and —$NR^6R^7$, where m, $X^1$, $X^2$, $R^4$, and $R^5$ are as defined herein.

"Leaving group" means a group with the meaning conventionally associated with it in synthetic organic chemistry, i.e., an atom or group displaceable under substitution reaction conditions. Examples of leaving groups include, but are not limited to, halogen, alkane- or arylenesulfonyloxy, such as methanesulfonyloxy, ethanesulfonyloxy, thiomethyl, benzene-sulfonyloxy, tosyloxy, and thienyloxy, dihalophosphinoyloxy, optionally substituted benzyloxy, isopropyloxy, acyloxy, and the like.

"Optional" or "optionally" means that the subsequently described event or circumstance may but need not occur, and that the description includes instances where the event or circumstance occurs and instances in which it does not.

"Disease" and "Disease state" means any disease, condition, symptom, disorder or indication.

"Inert organic solvent" or "inert solvent" means the solvent is inert under the conditions of the reaction being described in conjunction therewith, including for example, benzene, toluene, acetonitrile, tetrahydrofuran, N,N-dimethylformamide, chloroform, methylene chloride or dichloromethane, dichloroethane, diethyl ether, ethyl acetate, acetone, methyl ethyl ketone, methanol, ethanol, propanol, isopropanol, tert-butanol, dioxane, pyridine, and the like. Unless specified to the contrary, the solvents used in the reactions of the present invention are inert solvents.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

"Pharmaceutically acceptable salts" of a compound means salts that are pharmaceutically acceptable, as defined herein, and that possess the desired pharmacological activity of the parent compound. Such salts include:

acid addition salts formed with inorganic acids such as hydrochloric acid, hydrobromic acid, sulfuric acid, nitric acid, phosphoric acid, and the like; or formed with organic acids such as acetic acid, benzenesulfonic acid, benzoic, camphorsulfonic acid, citric acid, ethanesulfonic acid, fumaric acid, glucoheptonic acid, gluconic acid, glutamic acid, glycolic acid, hydroxynaphtoic acid, 2-hydroxyethanesulfonic acid, lactic acid, maleic acid, malic acid, malonic acid, mandelic acid, methane-sulfonic acid, muconic acid, 2-naphthalene-sulfonic acid, propionic acid, salicylic acid, succinic acid, tartaric acid, p-toluenesulfonic acid, trimethylacetic acid, and the like; or salts formed when an acidic proton present in the parent compound either is replaced by a metal ion, e.g., an alkali metal ion, an alkaline earth ion, or an aluminum ion; or coordinates with an organic or inorganic base. Acceptable organic bases include diethanolamine, ethanolamine, N-methylglucamine, triethanolamine, trometh-amine, and the like. Acceptable inorganic bases include aluminum hydroxide, calcium hydroxide, potassium hydroxide, sodium carbonate, sodium hydroxide, and the like.

The preferred pharmaceutically acceptable salts are the salts formed from acetic acid, hydrochloric acid, sulfuric acid, methanesulfonic acid, maleic acid, phosphoric acid, tartaric acid, citric acid, sodium, potassium, calcium, zinc, and magnesium.

"Protective group" or "protecting group" means the group which selectively blocks one reactive site in a multifunctional compound such that a chemical reaction can be carried out selectively at another unprotected reactive site in the meaning conventionally associated with it in synthetic chemistry. Certain processes of this invention rely upon the protective groups to block reactive nitrogen and/or oxygen atoms present in the reactants. For example, the terms "amino-protecting group" and "nitrogen protecting group" are used interchangeably herein and refer to those organic groups intended to protect the nitrogen atom against undesirable reactions during synthetic procedures. Exemplary nitrogen protecting groups include, but are not limited to, trifluoroacetyl, acetamido, benzyl (Bn), benzyloxycarbonyl (carbobenzyloxy, CBZ), p-methoxybenzyloxycarbonyl, p-nitrobenzyloxycarbonyl, tert-butoxycarbonyl (BOC), and the like. Skilled persons will know how to choose a group for the ease of removal and for the ability to withstand the following reactions.

"Subject" means mammals and non-mammals. Mammals means any member of the mammalia class including, but not limited to, humans; non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. The term "subject" does not denote a particular age or sex.

"Therapeutically effective amount" means an amount of a compound that, when administered to a subject for treating a disease state, is sufficient to effect such treatment for the disease state. The "therapeutically effective amount" will vary depending on the compound, disease state being treated, the severity or the disease treated, the age and relative health of the subject, the route and form of administration, the judgment of the attending medical or veterinary practitioner, and other factors.

The terms "those defined above" and "those defined herein" when referring to a variable incorporates by reference the broad definition of the variable as well as preferred, more preferred and most preferred definitions, if any.

"Treating" or "treatment" of a disease state includes:

(i) preventing the disease state, i.e. causing the clinical symptoms of the disease state not to develop in a subject that may be exposed to or predisposed to the disease state, but does not yet experience or display symptoms of the disease state.

(ii) inhibiting the disease state, i.e., arresting the development of the disease state or its clinical symptoms, or (iii) relieving the disease state, i.e., causing temporary or permanent regression of the disease state or its clinical symptoms.

The terms "treating", "contacting" and "reacting" when referring to a chemical reaction means adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

Nomenclature and Structures

In general, the nomenclature used in this application is based on AUTONOM™ v.4.0, a Beilstein Institute computerized system for the generation of IUPAC systematic nomenclature. Chemical structures shown herein were prepared using ISIS® version 2.2. Any open valency appearing on a carbon, oxygen or nitrogen atom in the structures herein indicates the presence of a hydrogen atom.

Whenever a chiral carbon is present in a chemical structure, it is intended that all stereoisomers associated with that chiral carbon are encompassed by the structure.

All patents and publications identified herein are incorporated herein by reference in their entirety.

Compounds of the Invention

One aspect of the invention provides compounds of formula I:

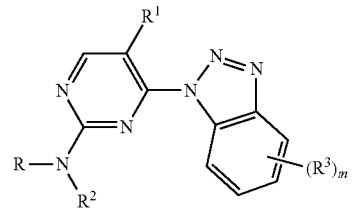

or a pharmaceutically acceptable salt thereof,
wherein
R is lower alkyl, hydroxy lower alkyl, or a radical selected from:

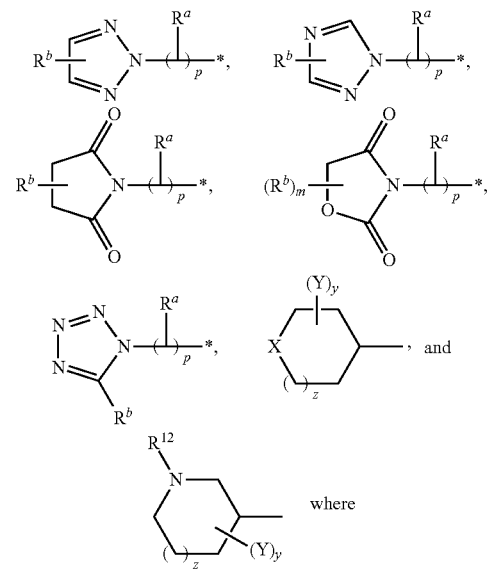

each $R^a$ is independently H, lower alkyl, OH, or hydroxy-lower alkyl;
each $R^b$ is independently H, lower alkyl, halo, nitro, or halo-lower alkyl;
p is 1, 2, 3, or 4;
X is O, $CR^4R^5$, C(=O), or $S(O)_x$;

$R^1$ is hydrogen, halo, alkyl, or $NH_2$;

each of $R^3$ is independently halo, —$NO_2$, lower alkyl, —CN, —$OR^7$, —$NR^8R^9$, —C(O)—$R^7$, —O—C(O)—$R^7$, —$CF_3$, —$CHF_2$, —$SO_2$—$R^{10}$, or two of $R^3$ form alkylene dioxy;

$R^4$ is hydrogen, lower alkyl, cyano, —$(CH_2)_nOR^7$, —$(CH_2)_nNR^8R^9$, —$(CH_2)_n$—C(O)—$NR^8R^9$, —$(CH_2)_n$—OC(O)—$NR^8R^9$, —$(CH_2)_n$—C(O)—$OR^7$; —NR—$SO_2$—$R^{10}$, —$(CH_2)_n$—$NR^8$—C(O)—$R^{11}$, or —$(CH_2)_n$—$NR^8$—C(O)—$OR^6$;

$R^5$ is hydrogen or alkyl;

or $R^4$ and $R^5$ together form alkylene dioxy;

$R^6$ is hydrogen, lower alkyl, heteroalkyl, cycloalkyl, heterocyclylalkyl, or —$NR^8R^9$;

$R^{10}$ is alkyl, cycloalkyl, heterocyclylalkyl, or —$NR^8R^9$;

$R^{11}$ is alkyl, cycloalkyl, heteroalkyl, or (heterocyclyl)alkyl;

$R^2$ and $R^7$ are each independently hydrogen, lower alkyl, hydroxyalkyl, or cycloalkyl;

$R^8$ is hydrogen, lower alkyl, or acyl;

$R^9$ is hydrogen, lower alkyl, heteroalkyl, aryl, heteroaryl, heterocyclyl, cycloalkyl;

or $R^8$ and $R^9$ together with the nitrogen atom to which they are connected to form a heterocyclyl comprising at least one nitrogen ring atom, optionally substituted with OH, oxo, lower alkyl, lower alkoxy, or acyl;

$R^{12}$ is H, lower alkyl, cycloalkyl, —C(O)—$R^7$, —$SO_2$—$R^{11}$;

each of m and x is independently an integer from 0 to 2;

Y is hydrogen, —$(CH_2)_n$—$OR^7$, —$(CH_2)_n$—C(O)—$R^7$ or —$(CH_2)_n$—C(O)$OR^7$;

each of y and z is independently 0 or 1; and n is an integer from 0 to 4.

In some embodiments, $R^2$ is hydrogen or methyl.

In other embodiments, R is

[structure: cyclohexyl ring with X substituent, $Y_y$ substituent, and $(\ )_z$]

where z is 1 and X is O or $CR^4R^5$. In some embodiments, $R^4$ is OH, —C(O)$NR^8R^9$, —$NR^8R^9$, —$NR^7SO_2R^{10}$, or —$OR^7$.

Still in other embodiments, m is 0.

Yet in other embodiments, $R^1$ is hydrogen, methyl, chloro, or fluoro.

In one embodiment, X is $CR^4R^5$, where $R^4$ and $R^5$ are those defined herein.

In other embodiments, $R^5$ is hydrogen or methyl.

Still in some embodiments, z is 1.

Still yet in other embodiments, $R^4$ is —$NR^7$—$SO_2$—$R^{10}$, where $R^7$, and $R^{10}$ are those defined herein.

In other embodiments, x is 2, $R^7$ is hydrogen or methyl, and $R^{10}$ is methyl, ethyl, or —$N(CH_3)_2$.

Yet still in other embodiments, z is 1, and $R^4$ is hydrogen, lower alkyl, cyano, —$(CH_2)_nOR^7$, or —$(CH_2)_nNR^8R^9$, or $R^4$ and $R^5$ together form alkylene dioxy, where n, $R^7$, $R^8$, and $R^9$ are those defined herein.

In yet other embodiments, $R^4$ is —$(CH_2)_nOR^7$, n is 0 or 1, and $R^7$ is hydrogen or methyl.

Still in other embodiments, $R^4$ is —$(CH_2)_nNR^8R^9$, where n, $R^8$, and $R^9$ are those defined herein. Within these embodiments, in cases n is 0 and $R^8$ is hydrogen, and $R^9$ is hydrogen, pyrimidin-2-yl, or pyridin-2-yl. Still in other cases within these embodiments, n is 0 and $R^8$ and $R^9$ together with the nitrogen-atom to which they are connected to form 2,5-dioxo-pyrrolidin-1-yl.

Yet in other embodiments, $R^4$ is hydrogen, methyl, ethyl, or cyano.

In other embodiments, $R^4$ and $R^5$ together form ethylene dioxy.

Still in other embodiments, compounds of formula I include those where z is 1, and $R^4$ is —$(CH_2)_n$—$NR^8$—C(O)—$R^{11}$, where n, $R^8$, and $R^{11}$ are those defined herein. Within these embodiments, in some instances n is 0, $R^8$ is hydrogen or methyl, and $R^{11}$ is methyl, ethyl, methoxymethyl, hydroxymethyl, (morpholin-4-yl)methyl, or (4-methyl-piperazin-1-yl)methyl.

Yet in other embodiments, z is 1, and $R^4$ is —$(CH_2)_n$—C(O)$NR^8R^9$, wherein n, $R^8$, and $R^9$ are those defined herein. Within these embodiments, in some instances n is 0, and $R^8$ and $R^9$ together with the nitrogen-atom to which they are connected to form morpholin-4-yl, pyrrolidin-1-yl, or 4-methyl-piperazin-1-yl. Still in other instances n is 0, and $R^8$ is hydrogen or methyl, and $R^9$ is (2-amino-2-methyl)propyl, (2-hydroxy)ethyl, tetrahydropyran-4-yl, cyclopropyl, or ethyl.

In other embodiments, z is 1, and $R^4$ is —$(CH_2)_n$—C(O)—$OR^7$, wherein n and $R^7$ are those defined herein. Within these embodiments, in some instances n is 0 and $R^7$ is hydrogen or methyl.

Still in other embodiments, $R^4$ and $R^5$ are hydrogen, z is 0, y is 1, and Y is hydroxy on the 3-position of the cyclopentyl ring moiety.

Yet in other embodiments, $R^4$ and $R^5$ are hydrogen, z is 1, y is 1, and Y is hydroxy, hydroxymethyl, or —$CO_2CH_2CH_3$ group on the 2-position of the cyclohexyl ring moiety.

In some embodiments of compound of formula I, z is 1, and X is O, C(=O), or S(O)$_2$.

In other embodiments of compound of formula I, X is $NR^6$, wherein $R^6$ is that defined in Claim 1. Within these embodiments, in some instances $R^6$ is hydrogen, —S(O)$_2CH_3$, or —$H_2C(O)NH_2$.

It should be appreciated that combinations of the different groups described herein may form other embodiments. In this manner, a variety of different compounds are embodied within the present invention. For example, in one embodiment, X is $CR^4R^5$, where $R^4$ and $R^5$ are those defined herein. Within this embodiment, in some instances $R^5$ is hydrogen or methyl. Still in other instances within this embodiment, z is 1, and $R^4$ is —$NR^7$—$SO_2$—$R^{10}$, where $R^7$ and $R^{10}$ are those defined herein. Within these instances, in some cases $R^7$ is hydrogen or methyl, and $R^{10}$ is methyl, ethyl, or —$N(CH_3)_2$. Yet in other instances within this embodiment, z is 1, and $R^4$ is hydrogen, lower alkyl, cyano, —$(CH_2)_nOR^7$, or —$(CH_2)_n$ $NR^8R^9$, or $R^4$ and $R^5$ together form alkylene dioxy, where n, $R^7$, $R^8$, and $R^9$ are those defined herein. Within these instances, in some cases $R^4$ is —$(CH_2)_nOR^7$, n is 0 or 1, and $R^7$ is hydrogen or methyl. In other cases within these instances, $R^4$ is —$(CH_2)_nNR^8R^9$, where n, $R^8$, and $R^9$ are those defined herein. Within these cases, some of the particular compounds include those where n is 0 and $R^8$ is hydrogen, and $R^9$ is hydrogen, pyrimidin-2-yl, or pyridin-2-yl. Other particular compounds within these cases include those where n is 0 and $R^8$ and $R^9$ together with the nitrogen-atom to which they are connected to form 2,5-dioxo-pyrrolidin-1-yl. Still in other cases, $R^4$ is hydrogen, methyl, ethyl, or cyano. In some instances within this embodiment, $R^4$ and $R^5$ together form ethylene dioxy.

Still in other embodiments, compounds of formula I include those where z is 1, and $R^4$ is —$(CH_2)_n$—$NR^8$—C (O)—R¹¹, where n, R⁸, and R¹¹ are those defined herein. Within these embodiments, in some instances n is 0, R⁸ is hydrogen or methyl, and R¹¹ is methyl, ethyl, methoxymethyl, hydroxymethyl, (morpholin-4-yl)methyl, or (4-methyl-piperazin-1-yl)methyl.

Yet in other embodiments, z is 1, and R⁴ is —(CH₂)ₙ—C(O)—NR⁸R⁹, wherein n, R⁸, and R⁹ are those defined herein. Within these embodiments, in some instances n is 0, and R⁸ and R⁹ together with the nitrogen-atom to which they are connected to form morpholin-4-yl, pyrrolidin-1-yl, or 4-methyl-piperazin-1-yl. Still in other instances n is 0, and R⁸ is hydrogen or methyl, and R⁹ is (2-amino-2-methyl)propyl, (2-hydroxy)ethyl, tetrahydropyran-4-yl, cyclopropyl, or ethyl.

In other embodiments, z is 1, and R⁴ is —(CH₂)ₙ—C(O)OR⁷, wherein n and R⁷ are those defined herein. Within these embodiments, in some instances n is 0 and R⁷ is hydrogen or methyl.

Still in other embodiments, R⁴ and R⁵ are hydrogen, z is 0, y is 1, and Y is hydroxy on the 3-position of the cyclopentyl ring moiety.

Yet in other embodiments, R⁴ and R⁵ are hydrogen, z is 1, y is 1, and Y is hydroxy, hydroxymethyl, or —CO₂CH₂CH₃ group on the 2-position of the cyclohexyl ring moiety.

In some embodiments of compound of formula I, z is 1, and X is O, C(=O), or S(O)₂.

In other embodiments of compound of formula I, X is NR⁶, wherein R⁶ is that defined in Claim 1. Within these embodiments, in some instances R⁶ is hydrogen, —S(O)₂CH₃, or —CH₂C(O)NH₂.

Still in other embodiments, compounds of formula I are of the formula IA:

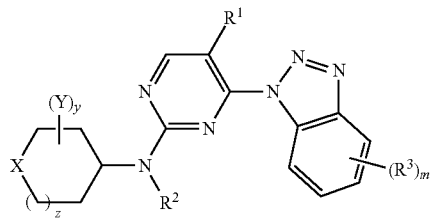

IA or a pharmaceutically acceptable salt thereof, where X, R¹, R², R³, X, Y, m, y, and z are those defined herein.

Representative compounds of the invention are shown in Table 1 below.

TABLE 1

Representative compounds of Formula I.

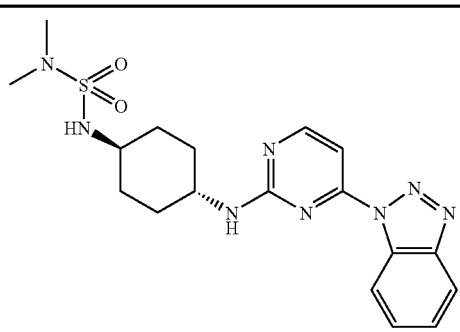

TABLE 1-continued

Representative compounds of Formula I.

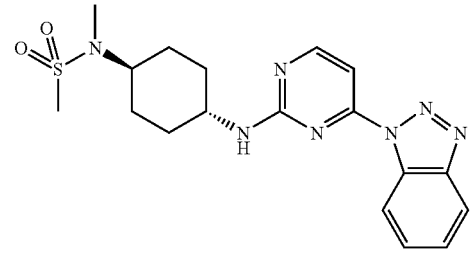 [SMILES: CN([C@H]1CC[C@H](Nc2nccc(-n3nnc4ccccc43)n2)CC1)S(C)(=O)=O]

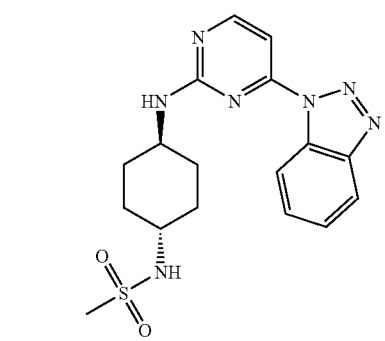 [SMILES: CS(=O)(=O)N[C@H]1CC[C@H](Nc2nccc(-n3nnc4ccccc43)n2)CC1]

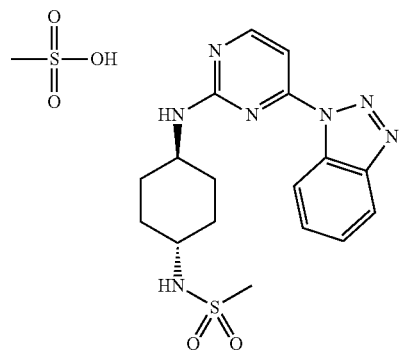

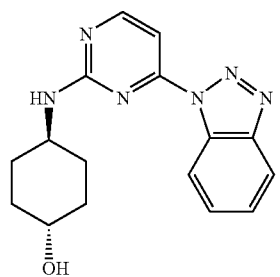 [SMILES: O[C@H]1CC[C@H](Nc2nccc(-n3nnc4ccccc43)n2)CC1]

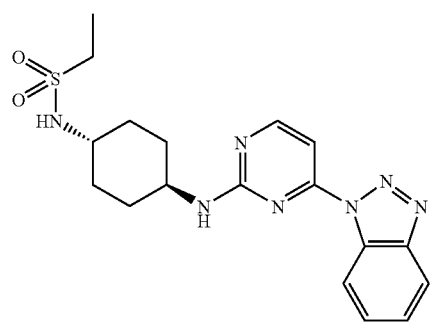 [SMILES: CCS(=O)(=O)N[C@H]1CC[C@H](Nc2nccc(-n3nnc4ccccc43)n2)CC1]

TABLE 1-continued
Representative compounds of Formula I.
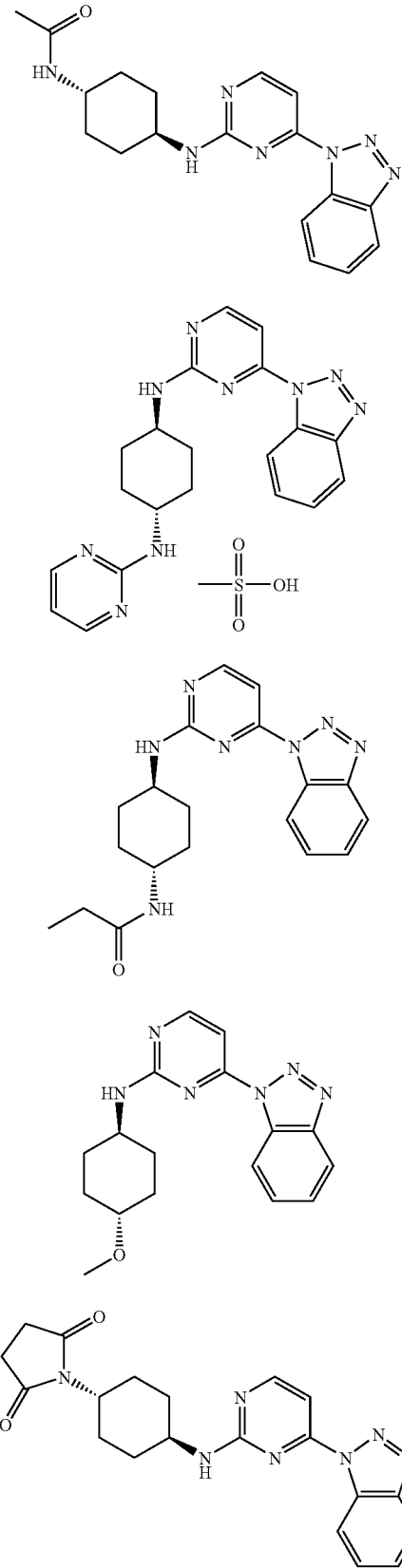
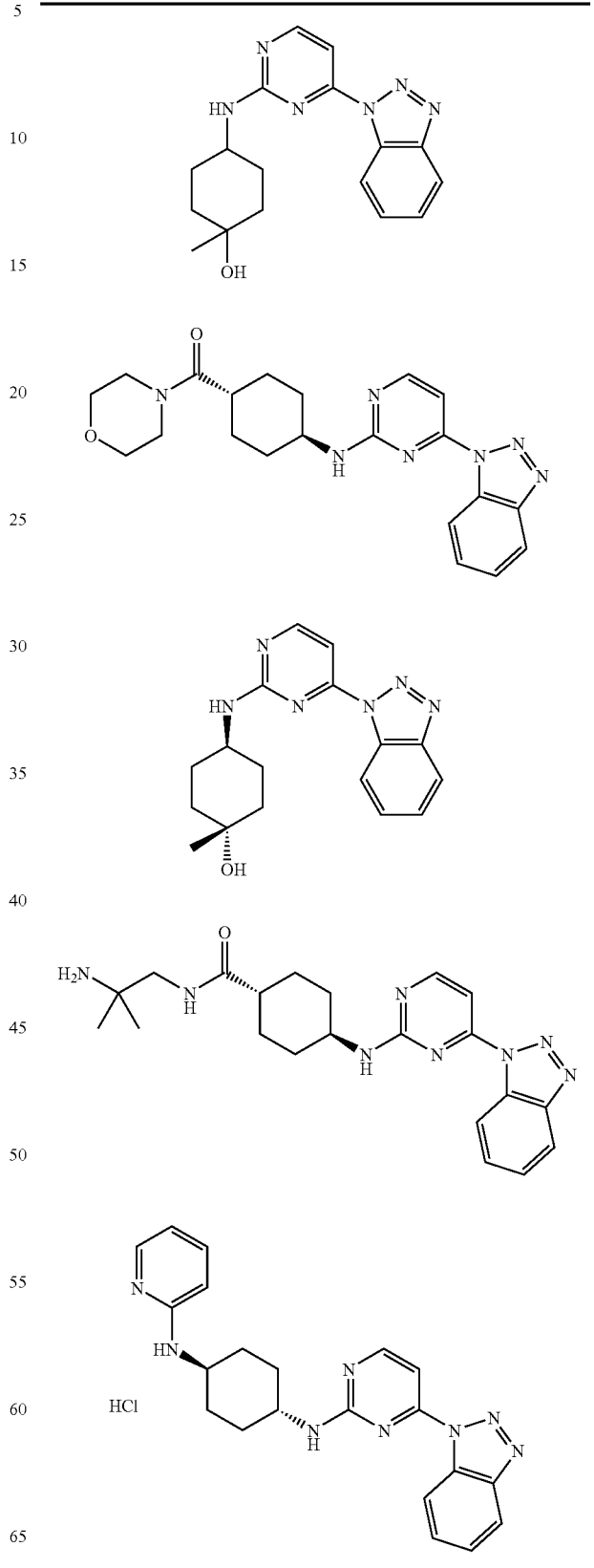

TABLE 1-continued
Representative compounds of Formula I.
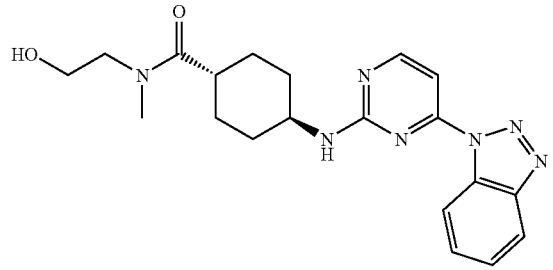 [SMILES: CN(CCO)C(=O)[C@H]1CC[C@H](Nc2nccc(-n3nnc4ccccc43)n2)CC1]
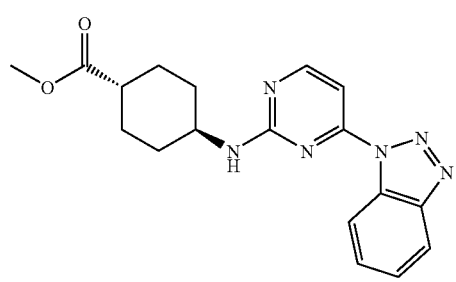 [SMILES: COC(=O)[C@H]1CC[C@H](Nc2nccc(-n3nnc4ccccc43)n2)CC1]
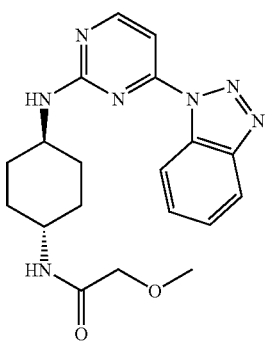 [SMILES: COCC(=O)N[C@H]1CC[C@H](Nc2nccc(-n3nnc4ccccc43)n2)CC1]
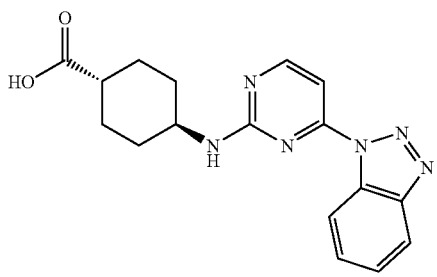 [SMILES: O=C(O)[C@H]1CC[C@H](Nc2nccc(-n3nnc4ccccc43)n2)CC1]
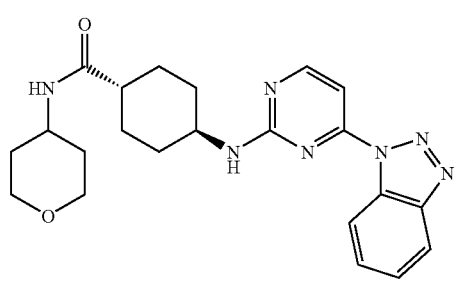 [SMILES: O=C(NC1CCOCC1)[C@H]1CC[C@H](Nc2nccc(-n3nnc4ccccc43)n2)CC1]
TABLE 1-continued
Representative compounds of Formula I.
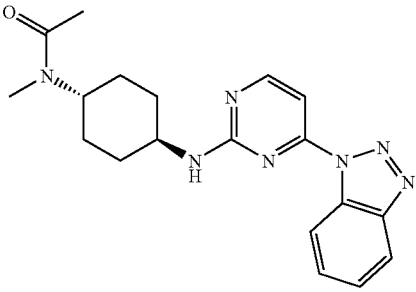 [SMILES: CC(=O)N(C)[C@H]1CC[C@H](Nc2nccc(-n3nnc4ccccc43)n2)CC1]
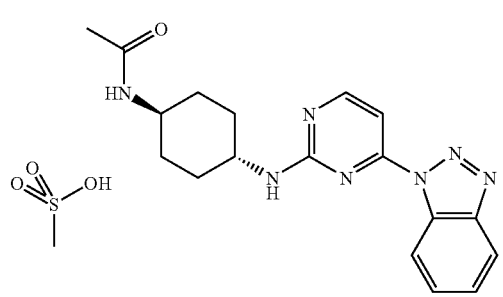
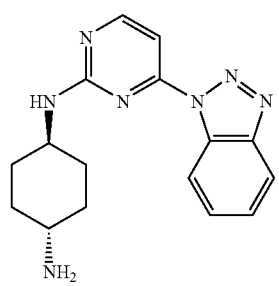 [SMILES: N[C@H]1CC[C@H](Nc2nccc(-n3nnc4ccccc43)n2)CC1]
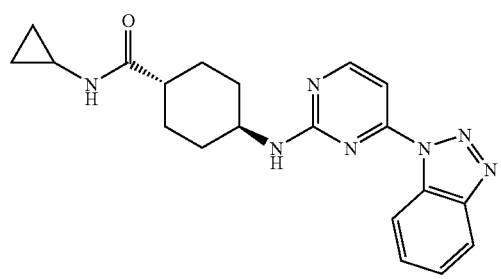 [SMILES: O=C(NC1CC1)[C@H]1CC[C@H](Nc2nccc(-n3nnc4ccccc43)n2)CC1]
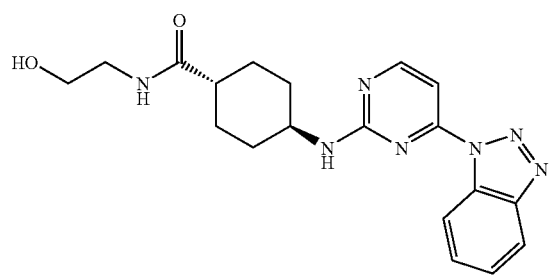 [SMILES: O=C(NCCO)[C@H]1CC[C@H](Nc2nccc(-n3nnc4ccccc43)n2)CC1]

TABLE 1-continued
Representative compounds of Formula I.
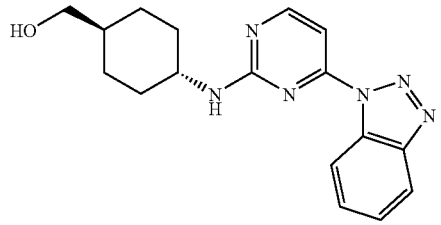 [SMILES: OC[C@H]1CC[C@H](Nc2nccc(-n3nnc4ccccc43)n2)CC1]
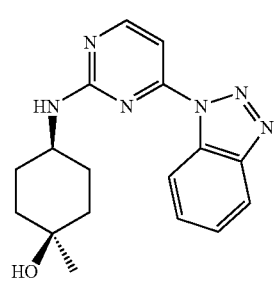 [SMILES: C[C@]1(O)CC[C@@H](Nc2nccc(-n3nnc4ccccc43)n2)CC1]
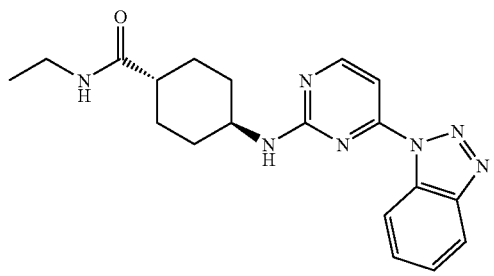 [SMILES: CCNC(=O)[C@H]1CC[C@H](Nc2nccc(-n3nnc4ccccc43)n2)CC1]
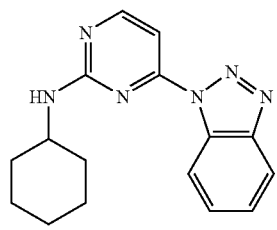 [SMILES: c1ccc2c(c1)nnn2-c1ccnc(NC2CCCCC2)n1]
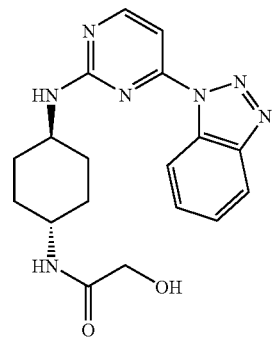 [SMILES: O=C(CO)N[C@H]1CC[C@H](Nc2nccc(-n3nnc4ccccc43)n2)CC1]
TABLE 1-continued
Representative compounds of Formula I.
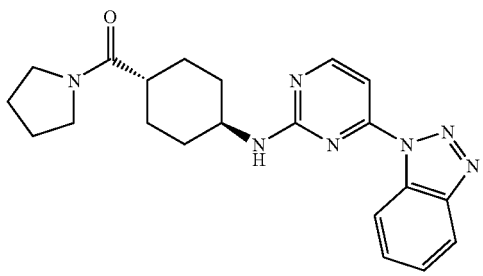 [SMILES: O=C([C@H]1CC[C@H](Nc2nccc(-n3nnc4ccccc43)n2)CC1)N1CCCC1]
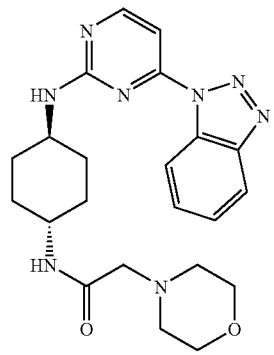 [SMILES: O=C(CN1CCOCC1)N[C@H]1CC[C@H](Nc2nccc(-n3nnc4ccccc43)n2)CC1]
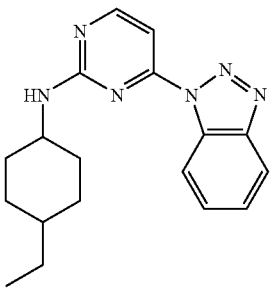 [SMILES: CCC1CCC(Nc2nccc(-n3nnc4ccccc43)n2)CC1]
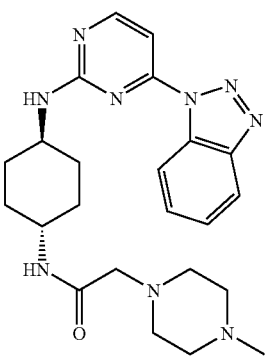 [SMILES: CN1CCN(CC(=O)N[C@H]2CC[C@H](Nc3nccc(-n4nnc5ccccc54)n3)CC2)CC1]
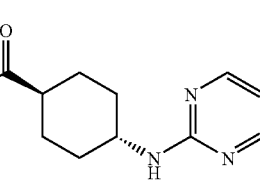

TABLE 1-continued
Representative compounds of Formula I.
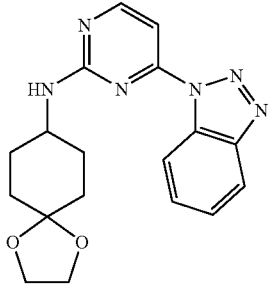 [SMILES: c1ccc2c(c1)nnn2-c1ccnc(NC2CCC3(CC2)OCCO3)n1]
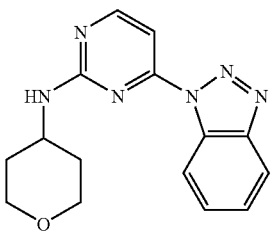 [SMILES: c1ccc2c(c1)nnn2-c1ccnc(NC2CCOCC2)n1]
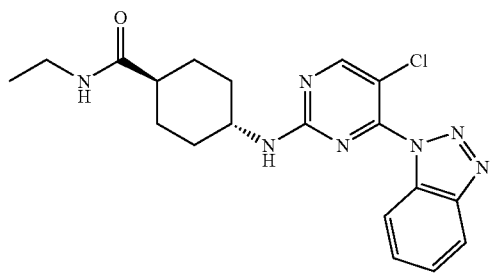 [SMILES: CCNC(=O)[C@H]1CC[C@H](Nc2ncc(Cl)c(-n3nnc4ccccc43)n2)CC1]
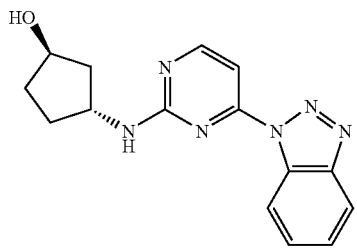 [SMILES: O[C@@H]1CC[C@@H](Nc2nccc(-n3nnc4ccccc43)n2)C1]
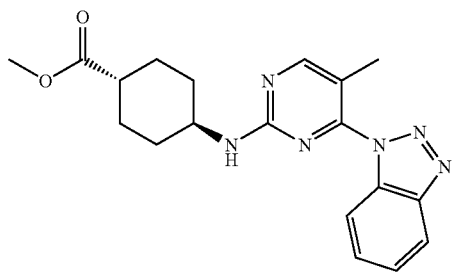
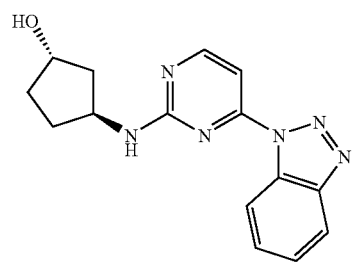 [SMILES: O[C@H]1CC[C@H](Nc2nccc(-n3nnc4ccccc43)n2)C1]
TABLE 1-continued
Representative compounds of Formula I.
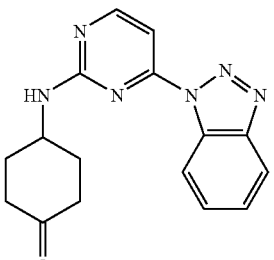
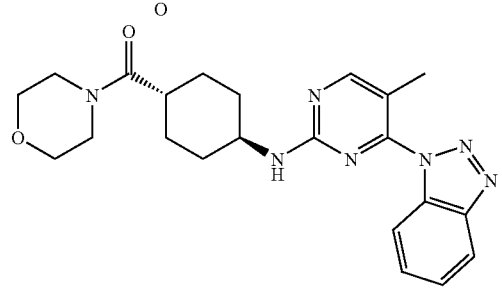
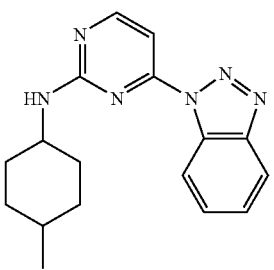 [SMILES: CC1CCC(Nc2nccc(-n3nnc4ccccc43)n2)CC1]
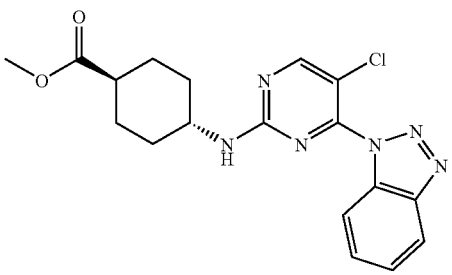 [SMILES: COC(=O)[C@H]1CC[C@H](Nc2ncc(Cl)c(-n3nnc4ccccc43)n2)CC1]
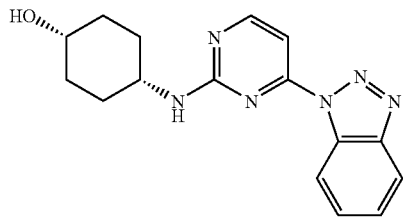 [SMILES: O[C@H]1CC[C@@H](Nc2nccc(-n3nnc4ccccc43)n2)CC1]
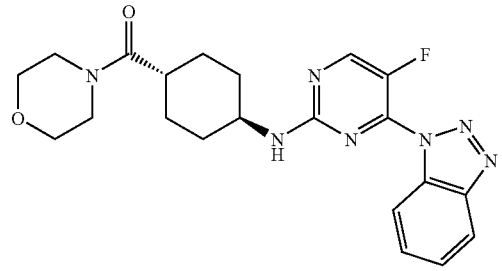 [SMILES: O=C([C@H]1CC[C@H](Nc2ncc(F)c(-n3nnc4ccccc43)n2)CC1)N1CCOCC1]

TABLE 1-continued
Representative compounds of Formula I.
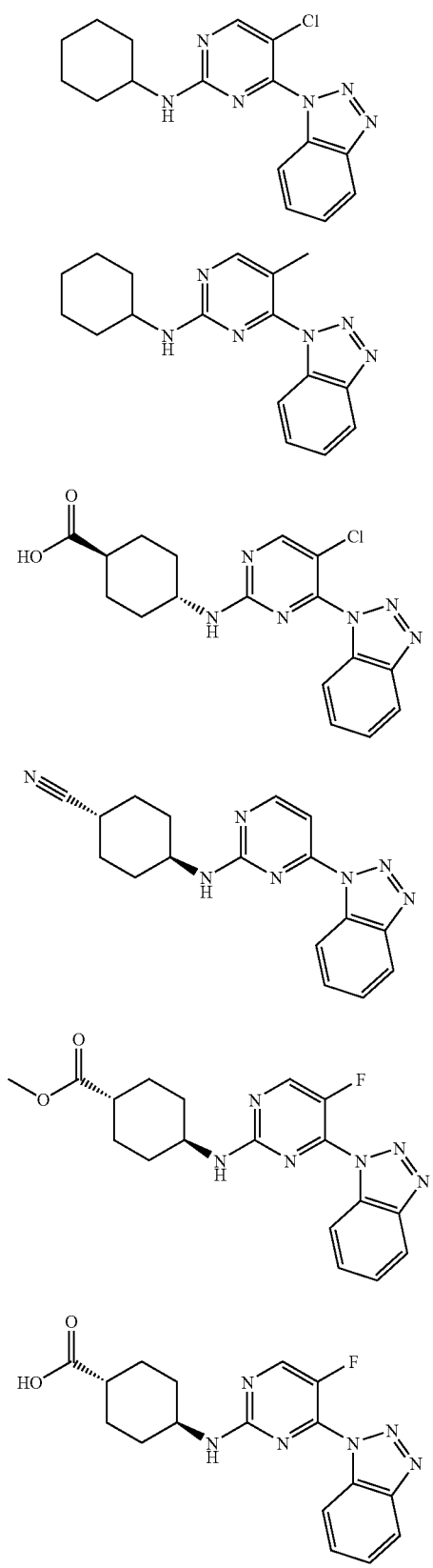
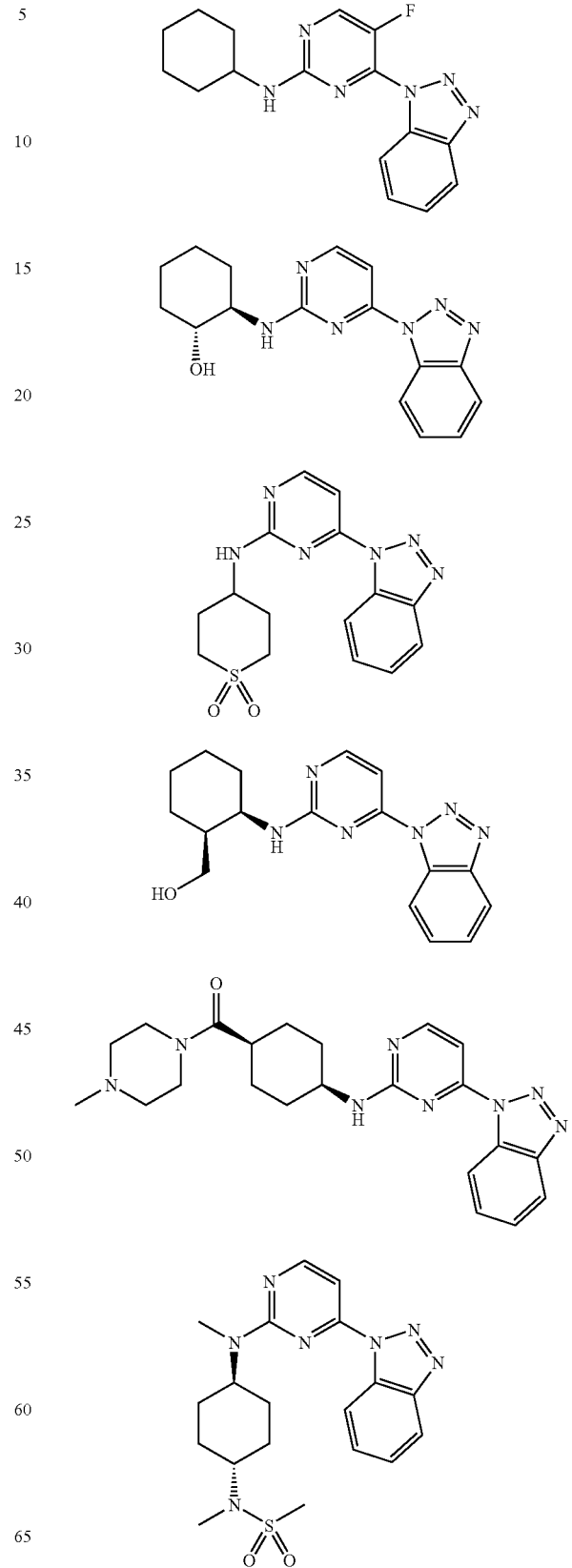

TABLE 1-continued
Representative compounds of Formula I.
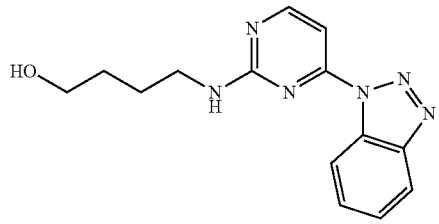 [SMILES: OCCCCNc1nccc(-n2nnc3ccccc32)n1]
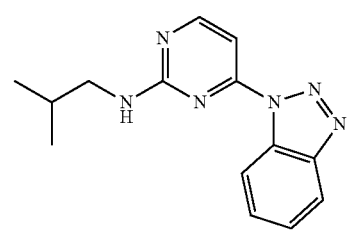 [SMILES: CC(C)CNc1nccc(-n2nnc3ccccc32)n1]
Chiral
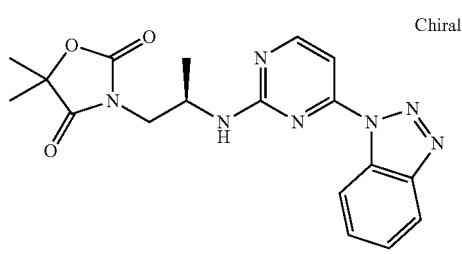 [SMILES: C[C@H](CN1C(=O)OC(C)(C)C1=O)Nc1nccc(-n2nnc3ccccc32)n1]
Chiral
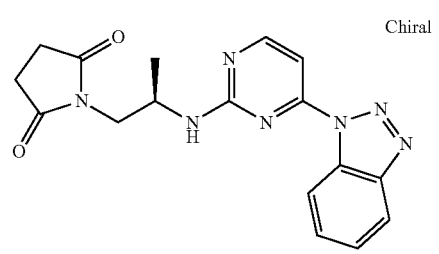 [SMILES: C[C@H](CN1C(=O)CCC1=O)Nc1nccc(-n2nnc3ccccc32)n1]
Chiral
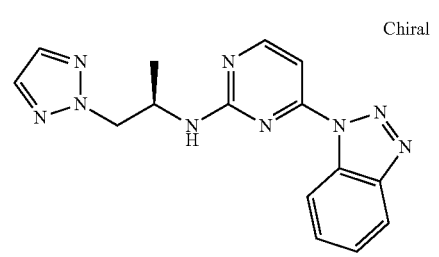 [SMILES: C[C@H](Cn1nccn1)Nc1nccc(-n2nnc3ccccc32)n1]
Chiral
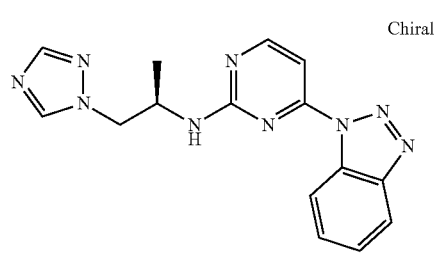
TABLE 1-continued
Representative compounds of Formula I.
Chiral
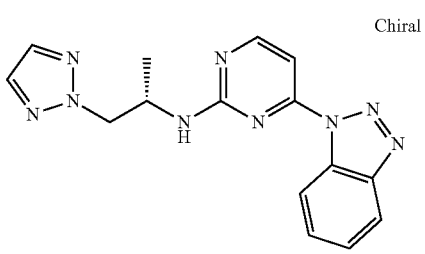 [SMILES: C[C@@H](Cn1nccn1)Nc1nccc(-n2nnc3ccccc32)n1]
Chiral
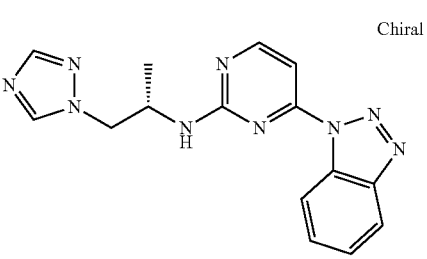 [SMILES: C[C@@H](Cn1cncn1)Nc1nccc(-n2nnc3ccccc32)n1]
Chiral
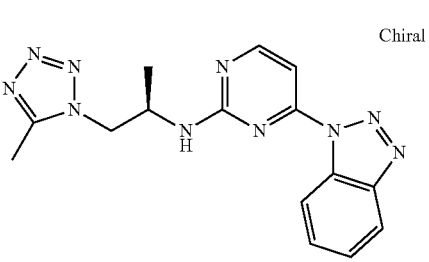 [SMILES: Cc1nnnn1C[C@@H](C)Nc1nccc(-n2nnc3ccccc32)n1]
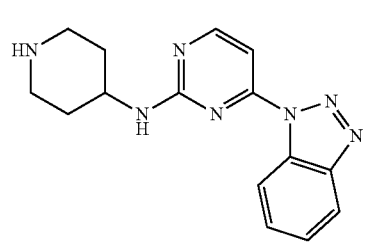 [SMILES: c1ccc2c(c1)nnn2-c1ccnc(NC2CCNCC2)n1]
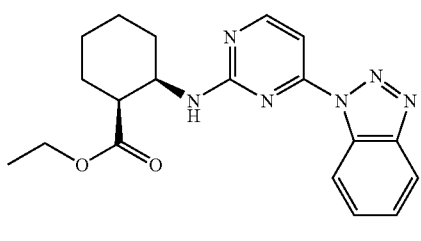 [SMILES: CCOC(=O)[C@H]1CCCC[C@H]1Nc1nccc(-n2nnc3ccccc32)n1]
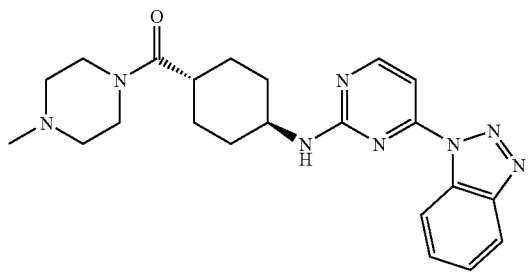 [SMILES: CN1CCN(C(=O)[C@H]2CC[C@H](Nc3nccc(-n4nnc5ccccc54)n3)CC2)CC1]

TABLE 1-continued

Representative compounds of Formula I.

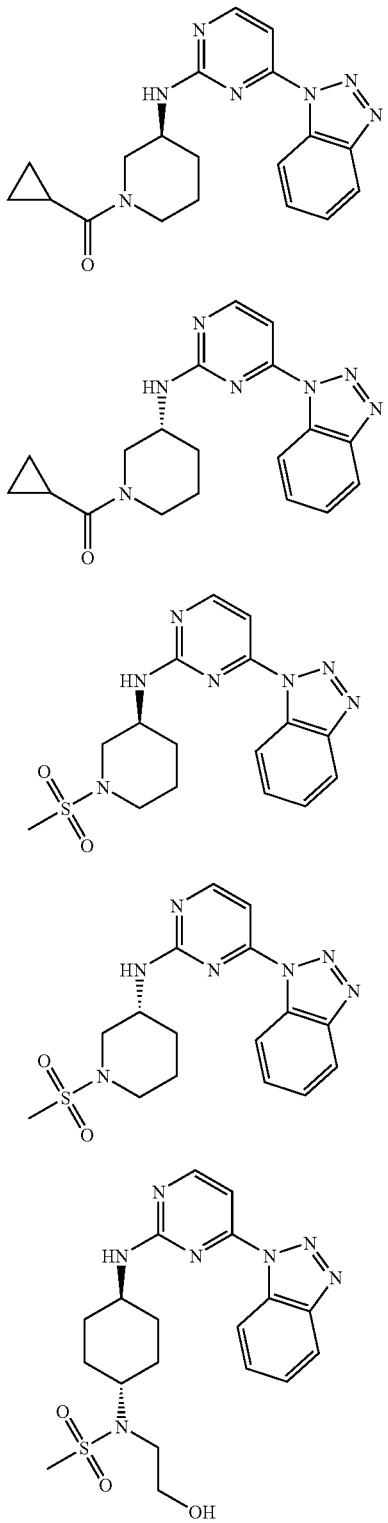

Synthesis

Compounds of the present invention can be made by a variety of methods depicted in the illustrative examples shown in the Examples section below. The starting materials and reagents used in preparing these compounds generally are either available from commercial suppliers, such as Aldrich Chemical Co., or are prepared by methods known to those skilled in the art following procedures set forth in references such as *Fieser and Fieser's Reagents for Organic Synthesis*; Wiley & Sons: New York, 1991, Volumes 1-15; *Rodd's Chemistry of Carbon Compounds*, Elsevier Science Publishers, 1989, Volumes 1-5 and Supplementals; and *Organic Reactions*, Wiley & Sons: New York, 1991, Volumes 1-40. The following synthetic reaction schemes are merely illustrative of some methods by which the compounds of the present invention can be synthesized, and various modifications to these synthetic reaction schemes can be made and will be suggested to one skilled in the art having referred to the disclosure contained in this application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reaction described herein preferably are conducted under inert atmosphere, at atmospheric pressure, at a reaction temperature range of from about −78° C. to about 230° C., and most preferably and conveniently at room (or ambient) temperature, e.g., about 20° C.

SCHEME I:

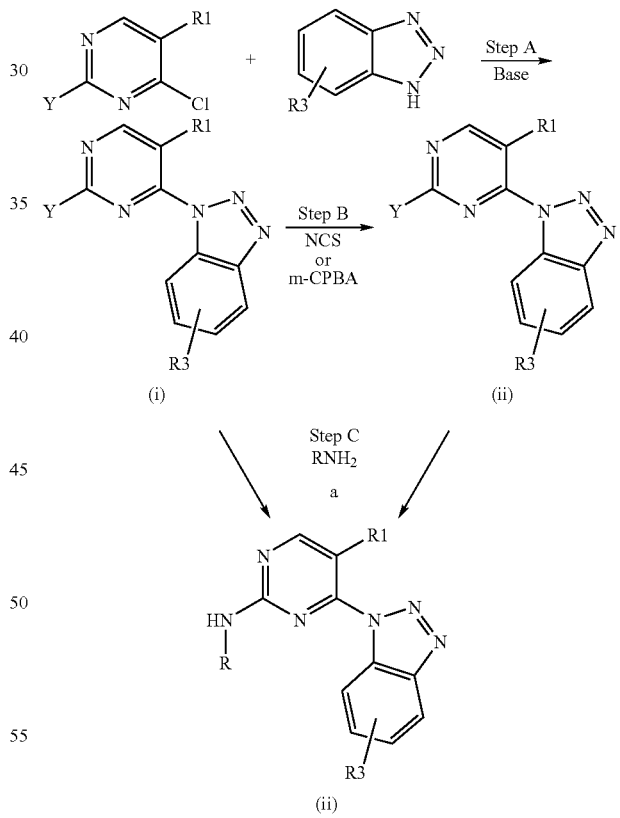

In Scheme I, $R_1$, R and $R_3$ and z are as defined above, Y is Cl or SMe, and Z is $MeSO_2$ or Cl. In Step A, a substituted 4-chloropyrimidine undergoes a $S_NAr$ reaction with a variably substituted 1H-benzotriazole in the presence of a base such as sodium hydride and in a polar aprotic solvent such as N,N-dimethylformamide at a temperature ranging between 0° C. and about RT.

In Step B the thiomethyl group Y is converted to a leaving group by oxidation with 3-chloroperoxybenzoic acid in apro tic solvents such as chloroform, or by chlorination with N-chlorosuccinimide.

In Step C, the leaving group Y or Z (Cl or MeSO$_2$) is displaced by a primary amine a thermally, by heating the mixture in a polar aprotic solvent such as 1-methyl-2-pyrrolidinone at a temperature ranging between about 100° C. and about 130° C. or by treatment with a base such as triethylamine at a temperature ranging between RT and 60° C. in a polar aprotic solvent such as tetrahydrofuran. Amines a may comprise, for example: cycloalkylamines such as variably substituted cyclohexylamines and cyclopentylamines; alkyl amines such as isobutylamine; hydroxyalkylamines such as 4-amino-1-butanol; heterocyclic amines such as 4-aminotetrahydropyran, 4-amino-1-BOC-piperidine. Numerous variably substituted alkyl, cycloalkyl and heterocyclic amines a are commercially available or are readily prepared by techniques known to those skilled in the art.

The products can then be purified, for example, by extraction, crystallization, preparative HPLC, flash chromatography, thin layer chromatography, and the like.

A compound of generic formula (iv) can undergo the transformations shown in Scheme II to give compounds that are the object of this invention.

In Scheme II, the variables are as defined herein. $R_a$ is $COR_{11}$, $Ar^1$, $CH_2CONR_8R_9$, $SO_2R_{11}$, or $SO_2NR_8R_9$. $R_b$ is alkyl, heteroalkyl, (heterocyclic)alkyl. $R_c$ and $R_d$ are independently H, alkyl, cycloalkyl, alkoxyalkyl, hydroxyalkyl, or heterocyclic. $R_e$ and $R_f$ are independently H, alkyl, cycloalkyl or heterocyclic. Z is $Ar^1$ or heterocyclic. $R_g$ is $COR^{11}$, $SO_2R^{11}$, $COAr^1$, $SO_2Ar^1$ or $SO_2NR^5R^8$. $R_h$ is alkyl or aryl.

Step F: b or c, NMP, heating or d, NMP, MW or NaBH$_4$, e, MeOH.
Step G: NaH, f, NMP.
Step H: NaOH, THF.
Step I: g, BOP, DIPEA, THF.
Step J: LAH, THF.
Step N: 1. IBX, DMSO; 2. h, NaBH(OAc)$_3$, AcOH, DCE.
Step K: PPh$_3$, DIAD, i, PhMe.
Step L: j, N$_2$H$_4$, EtOH, heating.
Step M: 1. HCl, THF; 2. k, THF.

When $R^x$ is NH$_2$ a compound of generic formula (iv) can under undergo an acylation or a sulfonylation reaction, as described in Step F, using for example an acylating agent b such as acetic anhydride in a polar aprotic solvent such as 1-methyl-2-pyrrolidinone at a temperature ranging between about RT and 70° C.; under the same conditions (iv) can be

SCHEME II:

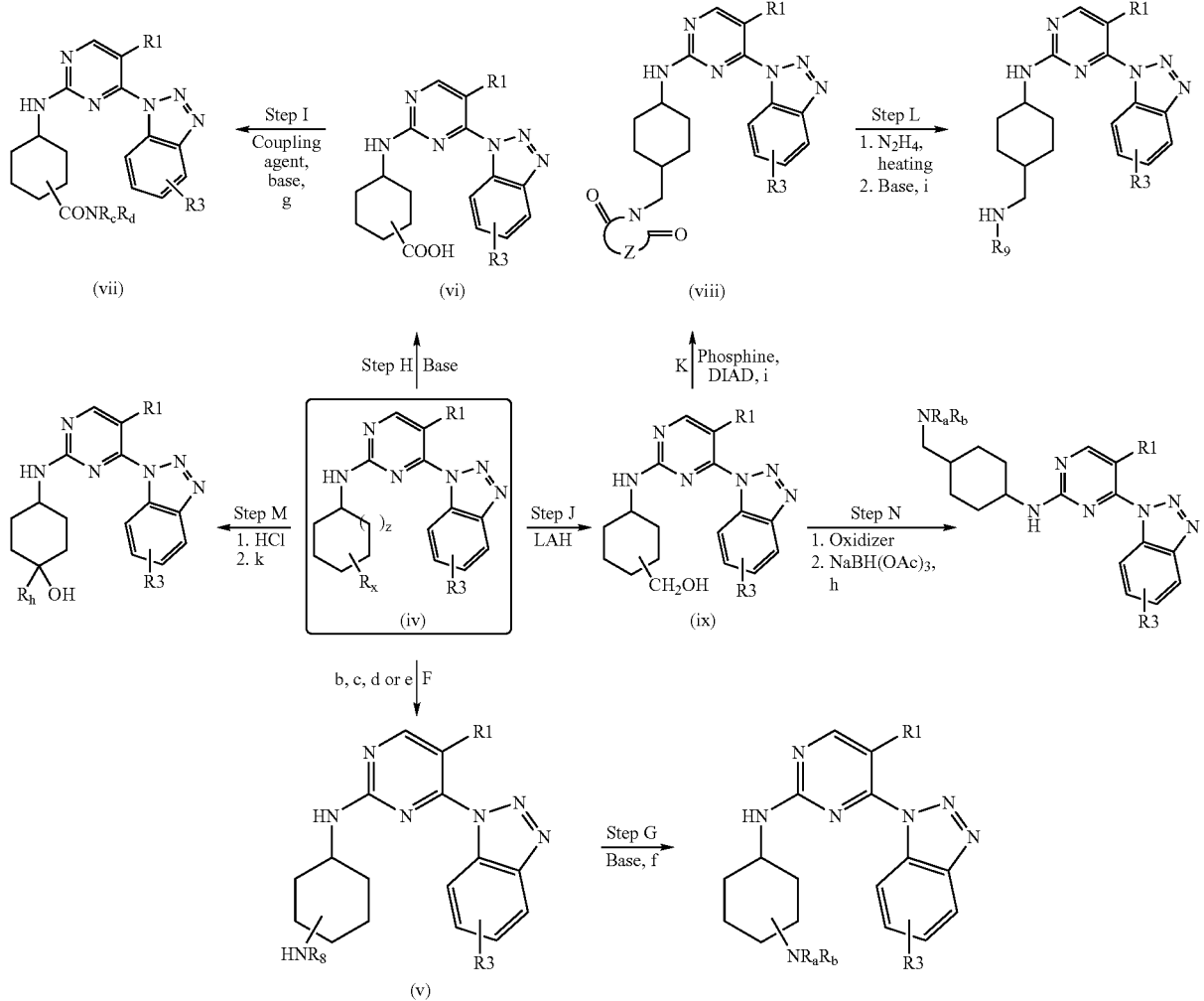

sulfonylated using, for example, methanesulfonic anhydride as sulfonylating agent c. Alternatively (iv) can undergo an arylation reaction using an heteroarylhalide d, for example, 2-fluoropyridine under microwave conditions in a polar aprotic solvent such as 1-methyl-2-pyrrolidinone at high temperature.

The acylating and sulfonylating agents b and c may comprise for example alkyl anhydrides, cyclic anhydrides, acyl and benzoyl chlorides, alkylsulfonyl anhydrides and alkylsulfonyl and benzoyl sulfonyl chlorides.

An alternative way to obtain product of generic formula (v) is by a reductive amination reaction, using, for example, sodium borohydride and an aldehyde e such as formaldehyde in a polar protic solvent such as methanol and the product can subsequently be acylated or sulfonylated using the same conditions as described above. Numerous alkyl, cycloalkyl and aryl aldehydes e are commercially available or are readily prepared by techniques well known to those skilled in the art.

In Step G an amine, amide or sulfonamide of generic formula (v) is alkylated using a base such as sodium hydride and an alkylating agent f such as methyl iodide in a polar aprotic solvent such as 1-methyl-2-pyrrolidinone. Alkylating agents f may comprise alkyl halides, heteroalkyl and (heterocyclic)alkyl halides.

When $R_x$ is COOMe or COOEt an ester of formula (iv) can be hydrolyzed to the corresponding carboxylic acid using an aqueous solution of an inorganic base such as sodium hydroxide in a polar aprotic solvent such as tetrahydrofuran as described in Step H. Subsequently a carboxylic acid (vi) can be coupled with a primary or secondary amine g in the presence of a coupling agent such as BOP and a base such as diisopropylethylamine in a polar aprotic solvent such as tetrahydrofuran as described in Step I to give an amide of generic formula (vii). Amines g may comprise for example alkylamines, alkoxyalkylamines, hydroxyalkylamines, cycloalkylamines and heterocyclic amines.

When $R_x$ is COOEt or COOMe an ester of formula (iv) can be reduced to the corresponding alcohol by treatment with lithium aluminum hydride in a polar aprotic solvent such as THF at temperatures ranging between about −78° C. and about RT as described in Step J. The alcohol of generic formula (ix) can be oxidized to the corresponding aldehyde by treatment with an oxidizing agent such as o-iodoxybenzoic acid in a polar aprotic solvent such as DMSO. The aldehyde obtained in this way can subsequently undergo a reductive amination reaction with a primary or secondary amine h such as morpholine in the presence of sodium triacetoxyborohydride and glacial acetic acid in an a polar solvent such as 1,2-dichloroethane (Step N). Amines h may comprise for example alkylamines, cycloalkylamines and heterocyclic amines. Alternatively the alcohol (ix) can undergo a Mitsunobu reaction with an imide i such as phthalimide in the presence of triphenylphosphine and DIAD in an a polar aprotic solvent such as toluene as described in Step K. The imines i may comprise cyclic and heterocyclic imines. A compound of generic formula (viii) when Z is phthalimide can be treated with hydrazine in a polar protic solvent such as ethanol at high temperature to give the corresponding primary amine which can then be acylated or sulfonylated by treatment with an acylating or sulfonylating agent such as acetyl chloride in presence of a base such as triethylamine as described in Step L. Acylating and sulfonylating agents may include acyl and aryl chlorides, sulfonyl and benzenesulfonyl chloride which are either commercially available or readily prepared through techniques known to those of ordinary skill in the art.

When $R_x$ is $O(CH_2)_2O$, a ketal (iv) can be converted in the corresponding ketone by treatment with an aqueous solution of HCl in a polar aprotic solvent such as tetrahydrofuran at high temperature; the ketone obtained in this manner can undergo an addition reaction with a Grignard reactant k in a polar aprotic solvent such as tetrahydrofuran at low temperature to give the corresponding tertiary alcohol as described in Step M. Numerous alkyl-, cycloalkyl- and aryl-Grignard reactants k are commercially available or are readily prepared by techniques known to those of ordinary skill in the art.

The products can then be purified, e.g., by extraction, crystallization, preparative HPLC, flash chromatography, thin layer chromatography and the like.

Utility

The compounds of this invention are CDK and JNK modulators, and as such are expected to be effective in the treatment of a wide range of CDK and JNK mediated disorders. Exemplary JNK mediated disorders include, without limitation, autoimmune disorders, inflammatory disorders, metabolic disorders, neurological diseases, and cancer. Accordingly, compounds of the invention can be used to treat one or more of such disorders. In some embodiments, compounds of the invention are used to treat a JNK mediated disorder such as rheumatoid arthritis, asthma, type II diabetes, Alzheimer's disease, Parkinson's disease or stroke. Exemplary CDK mediated disorders include, without limitation, inflammation (e.g., benign prostate hyperplasia, familial adenomauosis, polyposis, neuro-fibromatosis, atherosclerosis, pulmonary fibrosis, arthritis, psoriasis, inflammatory bowel disease, transplantation rejection infections), viral infections (including, without limitation, herpesvirus, poxvirus, Epstein-Barr virus), autoimmune disease (e.g., lupus, rheumatoid arthritis, psoriasis, inflammatory bowel disease), neurodegenerative disorders (including, without limitation, Alzheimer's disease), and neuro-degenerative diseases (for example, Parkinson's disease, amyotrophic lateral sclerosis, retinitis pigmentosa, spinal muscular atrophy, and cerebral degeneration).

Administration and Pharmaceutical Composition

The invention includes pharmaceutical compositions comprising at least one compound of the present invention, or an individual isomer, racemic or non-racemic mixture of isomers or a pharmaceutically acceptable salt or solvate thereof, together with at least one pharmaceutically acceptable carrier, and optionally other therapeutic and/or prophylactic ingredients.

In general, the compounds of the invention will be administered in a therapeutically effective amount by any of the accepted modes of administration for agents that serve similar utilities. Suitable dosage ranges are typically 1-500 mg daily, preferably 1-100 mg daily, and most preferably 1-30 mg daily, depending upon numerous factors such as the severity of the disease to be treated, the age and relative health of the subject, the potency of the compound used, the route and form of administration, the indication towards which the administration is directed, and the preferences and experience of the medical practitioner involved. One of ordinary skill in the art of treating such diseases will be able, without undue experimentation and in reliance upon personal knowledge and the disclosure of this application, to ascertain a therapeutically effective amount of the compounds of the present invention for a given disease.

Compounds of the invention may be administered as pharmaceutical formulations including those suitable for oral (including buccal and sub-lingual), rectal, nasal, topical, pulmonary, vaginal, or parenteral (including intramuscular, intraarterial, intrathecal, subcutaneous and intravenous) administration or in a form suitable for administration by inhalation or insufflation. The preferred manner of administration is generally oral using a convenient daily dosage regimen which can be adjusted according to the degree of affliction.

A compound or compounds of the invention, together with one or more conventional adjuvants, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semisolids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. Formulations containing about one (1) mg of active ingredient or, more broadly, about 0.01 to about one hundred (100) mg, per tablet, are accordingly suitable representative unit dosage forms.

The compounds of the invention may be formulated in a wide variety of oral administration dosage forms. The pharmaceutical compositions and dosage forms may comprise a compound or compounds of the present invention or pharmaceutically acceptable salts thereof as the active component. The pharmaceutically acceptable carriers may be either solid or liquid. Solid form preparations include powders, tablets, pills, capsules, cachets, suppositories, and dispersible granules. A solid carrier may be one or more substances which may also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. The powders and tablets preferably contain from about one (1) to about seventy (70) percent of the active compound. Suitable carriers include but are not limited to magnesium carbonate, magnesium stearate, talc, sugar, lactose, pectin, dextrin, starch, gelatin, tragacanth, methylcellulose, sodium carboxy-methylcellulose, a low melting wax, cocoa butter, and the like. The term "preparation" is intended to include the formulation of the active compound with encapsulating material as carrier, providing a capsule in which the active component, with or without carriers, is surrounded by a carrier, which is in association with it. Similarly, cachets and lozenges are included. Tablets, powders, capsules, pills, cachets, and lozenges may be as solid forms suitable for oral administration.

Other forms suitable for oral administration include liquid form preparations including emulsions, syrups, elixirs, aqueous solutions, aqueous suspensions, or solid form preparations which are intended to be converted shortly before use to liquid form preparations. Emulsions may be prepared in solutions, for example, in aqueous propylene glycol solutions or may contain emulsifying agents, for example, such as lecithin, sorbitan monooleate, or acacia. Aqueous solutions can be prepared by dissolving the active component in water and adding suitable colorants, flavors, stabilizers, and thickening agents. Aqueous suspensions can be prepared by dispersing the finely divided active component in water with viscous material, such as natural or synthetic gums, resins, methylcellulose, sodium carboxymethylcellulose, and other well known suspending agents. Solid form preparations include solutions, suspensions, and emulsions, and may contain, in addition to the active component, colorants, flavors, stabilizers, buffers, artificial and natural sweeteners, dispersants, thickeners, solubilizing agents, and the like.

The compounds of the invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilization from solution for constitution before use with a suitable vehicle, e.g., sterile, pyrogen-free water.

The compounds of the invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

The compounds of the invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the invention may be formulated for vaginal administration. Pessaries, tampons, creams, gels, pastes, foams or sprays containing in addition to the active ingredient such carriers as are known in the art to be appropriate.

The subject compounds may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chloro-fluorocarbon (CFC), for example, dichlorodifluoromethane, trichlorofluoromethane, or dichloro-tetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatin or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to an skin-adhesive solid support. The compound of interest can also be combined with a penetration enhancer, e.g., Azone (1-dodecylazacycloheptan-2-one). Sustained release delivery systems are inserted subcutaneously into the sub-dermal layer by surgery or injection. The subdermal implants encapsulate the compound in a lipid soluble membrane, e.g., silicone rubber, or a biodegradable polymer, e.g., polylactic acid.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Other suitable pharmaceutical carriers and their formulations are described in *Remington: The Science and Practice of Pharmacy* 1995, edited by E. W. Martin, Mack Publishing Company, 19th edition, Easton, Pa. Representative pharmaceutical formulations containing a compound of the present invention are described below.

The compounds of this invention may be used in combination (administered in combination or sequentially) with known anti-cancer treatments such as radiation therapy or with cytostatic or cytotoxic agents, such as for example, but not limited to, DNA interactive agents, such as cisplatin or doxorubicin; topoisomerase II inhibitors such as etoposide: topoisomerase I inhibitors such as CPT-11 or topotecan; tublin interacting agents, such as paclitaxel, docetaxel or epothilones; hormonal agents such as tamoxifen: thymidilaate synthaes inhibitors, such as 5-fluorouracil; and antimetabolites such as methotrexate. Compounds of formula I may also be useful in combination with modulators of p53 transactivation.

If formulated as a fixed dose, the above-described combination products include the compounds of this invention within the dosage range described above and the other pharmaceutically active agent or treatment within its approved dose range. For example, an early cdk1 inhibitor olomucine has been found to act synergistically with well known cytotoxic agents in inducing apoptosis. (*J. Cell Sci.* (1995) 108: 2897-904). Compounds of formula I may also be administered sequentially with known anticancer or cytoxic agents when concomitant administration or a combination is inappropriate. This invention is not limited in the sequence of administration: compounds of formula I may be administered either prior to or after administration of the known anticancer or cytotoxic agent. For example, the cytotoxic activity of the cdk inhibitor flavopiridol is affected by the sequence of administration with anticancer agents. (*Cancer Res* (1997) 57:3375).

The pharmacological properties of the compounds of this invention may be confirmed by a number of pharmacological assays. The exemplified pharmacological assays which follow have been carried out with the compounds according to the invention and their salts. The compounds of the invention exhibited cdk4/cyclin D activity with $IC_{50}$ values and Ki values of less than 1.0 µM. Additionally, the antiproliferative potency of some compounds of the invention was tested in the human colon tumor cell line HCT116 with $IC_{90}$ values reported from an MTT assay of less than 30 µM, preferably less than 5 µM.

Additional objects, advantages, and novel features of this invention will become apparent to those skilled in the art upon examination of the following examples thereof, which are not intended to be limiting.

EXAMPLES

LIST OF ABBREVIATIONS

BOP Benzotriazol-1-yloxytris(dimethylamino)phosphonium hexafluorophosphate
DCE 1,2-Dichloroethane
DCM Dichloromethane/Methylene chloride
DIPEA Diisopropylethylamine
DMF N,N-dimethylformamide
DIAD Diisopropyl azodicarboxylate
DMSO Dimethyl sulfoxide
EtOAc Ethyl acetate
LAH Lithium aluminum hydride
IBX o-Iodoxybenzoic acid
m-CPBA 3-Chloroperoxybenzoic acid
MeOH Methanol
MsCl Methanesulfonyl chloride
MW Microwaves
NCS N-Chlorosuccinimide
NMP 1-Methyl-2-pyrrolidinone
RT Room temperature
STABH Sodium triacetoxyborohydride
TBS t-butylsilyl
TEA Triethylamine
THF Tetrahydrofuran
TLC Thin layer chromatography Example 1

Synthesis of 2,4,5-trichloro-pyrimidine

The synthesis of 2,4,5-trichloro-pyrimidine was carried out according to the process shown in Scheme A.

SCHEME A

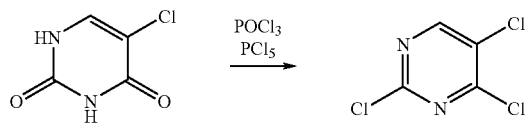

5-Chlorouracil (4.5 g, 30.82 mmol) was dissolved in phosphorus oxychloride (100 mL) and phosphorus pentachloride (19.2 g, 92.46 mmol) was added. The reaction mixture was heated at reflux overnight; it was then cooled to RT and the solvent was evaporated under reduced pressure. The residue was cooled to 0° C. and ice flakes were carefully added. The resulting mixture was stirred for 10 minutes; it was then partitioned between water and DCM. The organic phase was separated and washed 3 times with water. The aqueous layers were combined and extracted twice with DCM. The combined organic extracts were dried over $Na_2SO_4$, filtered and evaporated under reduced pressure to give 6 g (95% yield) of 2,4,5-trichloro-pyrimidine as a yellow oil without further purifications.

Example 2

Synthesis of
1-(2,5-dichloro-pyrimidin-4-yl)-1H-benzotriazole

The synthesis of 1-(2,5-dichloro-pyrimidin-4-yl)-1H-benzotriazole was carried out according to the process shown in Scheme B.

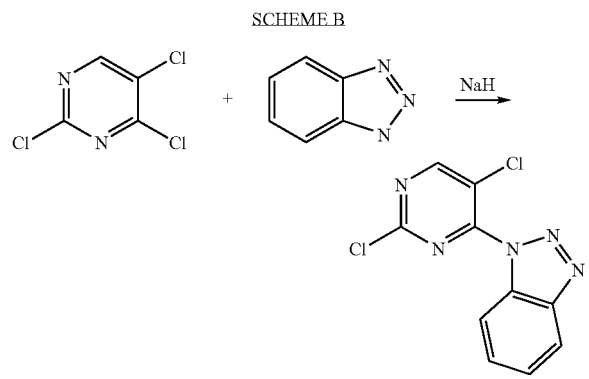

A solution of benzotriazole (2.14 g, 18.03 mmol) in DMF (10 mL) was slowly added at 0° C. to a solution of NaH (60% in mineral oil, 0.850 g, 21.3 mmol) in DMF (20 mL) under nitrogen atmosphere. The reaction mixture was stirred at 0° C. for 15 minutes; a solution of 2,4,5-trichloropyrimidine (3 g, 16.39 mmol) in DMF (20 mL) was then slowly added at 0° C. The reaction mixture was allowed to reach RT while stirring overnight. The solvent was evaporated under reduced pressure; the residue was taken up with EtOAc and washed 3× with water. The aqueous layers were combined and extracted 3 times with EtOAc. The combined organic extracts were dried over $Na_2SO_4$, filtered and evaporated under reduced pressure to give a crude oil. This material was purified via flash chromatography (heptane/EtOAc, 8/2) to give 1.5 g (34% yield) of 1-(2,5-dichloro-pyrimidin-4-yl)-1H-benzotriazole.

The following compounds were similarly prepared using the appropriate chloropyrimidine:

1-(2-Chloro-pyrimidin-4-yl)-1H-benzotriazole;

1-(2-Chloro-5-fluoro-pyrimidin-4-yl)-1H-benzotriazole; and 1-(2-Chloro-5-methyl-pyrimidin-4-yl)-1H-benzotriazole.

Example 3

Synthesis of 1-(2-methanesulfonyl-pyrimidin-4-yl)-H-benzotriazole

The synthesis of 1-(2-methanesulfonyl-pyrimidin-4-yl)-1H-benzotriazole was carried out according to the process shown in Scheme C.

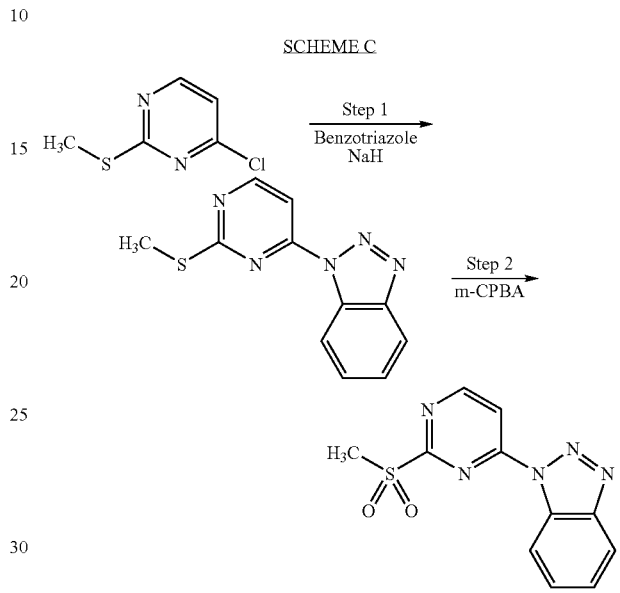

Step 1: synthesis of 1-(2-methylsulfanyl-pyrimidin-4-yl)-1H-benzotriazole

A 1 L round bottom flask was loaded with sodium hydride dispersion (10.0 g, 250 mmol, 60% in mineral oil) and 200 mL of DMF, and the resulting slurry cooled with an ice bath. Benzotriazole (18.02 g, 151 mmol) was added portionwise over a 10-12 min period. The reaction mixture was stirred for 10 min to allow gas evolution to subside; the ice bath was then removed and 4-chloro-2-methylthiopyrimidine (24.07 g, 150 mmol) was added. The resulting mixture was stirred at RT for 15 minutes, then placed in a 90° C. oil bath for 1.5 hour. The heating bath was turned off and the reaction mixture was allowed to slowly cool with stirring overnight. The reaction mixture was then poured into 500 mL of water and stirred for 20 min, and then filtered. The collected solids were washed with 3 portions of water and 3 portions of a mixture of hexanes/EtOAc (10:1 to 5:1), then dried to give 1-(2-methylsulfanyl-pyrimidin-4-yl)-1H-benzotriazole as an off-white solid (27.05 g, 74% yield), mp=180.5-181.7° C.; MS=244 $(M+H)^+$.

Step 2: synthesis of 1-(2-methanesulfonyl-pyrimidin-4-yl)-1H-benzotriazole 1-(2-Methylsulfanyl-pyrimidin-4-yl)-1H-benzotriazole (27.05 g, 111 mmol) was dissolved/suspended in 600 mL of $CHCl_3$ in a 2 L round bottom flask. The mixture was cooled with an ice bath and m-CPBA (58.03 g, 259 mmol, ca. 77%) was slowly added portionwise, while maintaining the reaction temperature below 15° C. The reaction mixture was slowly warmed to RT and stirred for 16 hours, then refluxed for 1 hour. It was cooled and treated with aqueous sodium thiosulfate; the organic layer was separated and washed with 3 portions of aqueous sodium bicarbonate. It was then dried over sodium sulfate, filtered and concentrated under reduced pressure until the formation of a suspension, which was filtered and dried to give the 1-(2-methanesulfonyl-pyrimidin-4-yl)-1H-benzotriazole as a white solid (20.78 g, 68% yield), mp=201.8-202.5° C.; MS=276 (M+H)$^+$.

Example 4

Synthesis of N-Pyrimidin-2-yl-cyclohexane-trans-1,4-diamine

The synthesis of N-Pyrimidin-2-yl-cyclohexane-trans-1,4-diamine was carried out according to the process shown in Scheme D.

SCHEME D

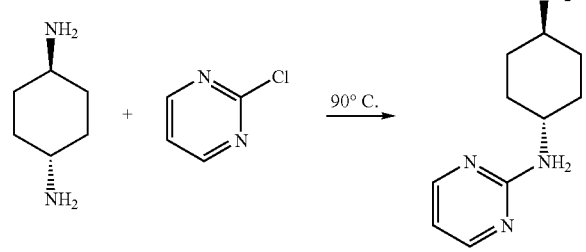

To a 90° C. solution of trans-1,4-diaminocyclohexane (10.10 g, 88 mmol) in dioxane/MeOH (40 mL/40 mL) was slowly added a solution of 2-chloropyrimidine (3.14 g, 45 mmol) in dioxane/MeOH (40 mL/40 mL). The reaction mixture was refluxed overnight, then cooled and the suspension that formed was filtered. The filtrate was concentrated under reduced pressure to form another suspension which was filtered again. The collected liquids were partitioned between EtOAc and aqueous NaHCO$_3$. The product remained in the aqueous layer, and was extracted with 3 portions of CH$_2$Cl$_2$, dried over Na$_2$SO$_4$ and filtered; the solvent was evaporated under reduced pressure. The crude residue was recrystallized from hexanes/CH$_2$Cl$_2$ (1/1) and dried to give N-pyrimidin-2-yl-cyclohexane-trans-1,4-diamine as an off-white solid (1.20 g, 14% yield), mp=126.9-128.4° C.; MS=193 (M+H)$^+$.

Example 5

Synthesis of Amines

The synthesis of various amines were carried out according to the process shown in Scheme E.

SCHEME E

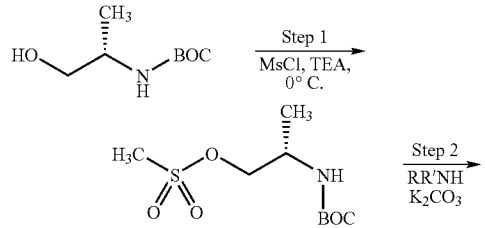

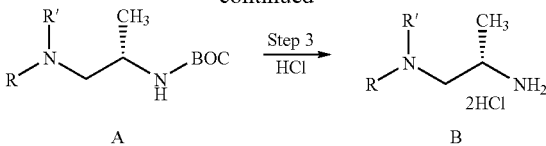

Step 1: Synthesis of methanesulfonic acid (S)-2-tert-butoxycarbonylamino-propyl ester 2-(S)-Boc-amino-propanol (10 g, 57.1 mmol, 1.00 equivalents) was dissolved in DCM (200 mL) under nitrogen atmosphere; and triethylamine (7.49 g, 10.32 mL, 74.2 mmol, 1.30 eq) was added at RT. The reaction mixture was cooled to 0° C. and mesyl chloride (7.39 g, 4.99 mL, 64.5 mmol, 1.13 eq) was added under nitrogen atmosphere. The resulting mixture was stirred at 0° C. for 3 hours, then washed 3 times with H$_2$O (100 mL), the aqueous phases were combined, and extracted 3 times with DCM (50 mL). The organic extracts were combined, dried over Na$_2$SO$_4$, filtered and evaporated to provide methanesulfonic acid (S)-2-tert-butoxycarbonyl-amino-propyl ester as a white solid (14.17 g, 98% yield). $^1$H NMR (400 MHz, CDCl$_3$) δ ppm 4.56-4.70 (1 H, m), 4.17-4.27 (1 H, m), 4.10-4.17 (1 H, m), 3.89-4.02 (1 H, m), 2.97-3.05 (3 H, m), 1.38-1.47 (9 H, m), 1.22 (3 H, d, J=6.85 Hz).

In the same manner was prepared methanesulfonic acid (R)-2-tert-butoxycarbonylamino-propyl ester (white solid) using the 2-(R)-boc-2-amino-propanol as starting material (yield=14.09 g, 97% yield); $^1$H NMR (400 MHz, CDCl$_3$) δ ppm 4.55-4.67 (1 H, m), 4.17-4.27 (1 H, m), 4.11-4.17 (1 H, m), 3.90-4.02 (1 H, m), 3.02 (3 H, s), 1.43 (9 H, s), 1.22 (3 H, d, J=6.85 Hz).

Step 2: Synthesis of Amine A

Methanesulfonic acid (S)-2-tert-butoxycarbonylamino-propyl ester (1.00 g, 3.94 mmol, 1 eq) was dissolved in DMF (16 mL), under nitrogen atmosphere, K$_2$CO$_3$ (1.09 g, 7.89 mmol, 2 eq) and the appropriate amine of the formula RR'NH (3.95 mmol, 1 equiv,) were then added at RT. The reaction mixture was stirred at 90° C. for 1 hour. The resulting mixture was concentrated to provide a crude solid which was dissolved with a 1:1 iPrOH/CHCl$_3$ mixture, washed twice with H$_2$O (10 mL). The aqueous phases were combined, extracted 3 times with a 1:1 iPrOH/CHCl$_3$ mixture (20 mL). The organic extracts were combined, dried over Na$_2$SO$_4$, filtered and evaporated to provide the crude desired amine.

Similar reactions were carried out with the (S)- and (R)-boc amino mesyltate derivatives, and the following amines to obtain corresponding products: Succinimide; 2-pyrrolidinone; 5,5-dimethyloxazolidine-2,4-dione; 5-methyl-1H-tetrazole; 1,2,3-triazol; 1,2,4-triazole; methyl-4-imidazole carboxylate; and methyl-1,2,3-triazole-3-carboxylate.

$^1$H NMR's of the crude mixtures were performed. These boc amino derivatives were used in the next step without purification.

Step 3: Synthesis of Amine B

The (S)-boc-amino derivative A (3.5 mmol, 1 equivalent) was dissolved in a solution of 4N HCl in 1,4-dioxane (5 mL). The reaction mixture was stirred for 18 hours at RT. The reaction mixture was concentrated under reduced pressure providing a crude solid which was used without further purification in the next step.

Using this procedure the following amines were prepared:
3-((R)-2-Amino-propyl)-5,5-dimethyl-oxazolidine-2,4-dione;
1-((R)-2-Amino-propyl)-pyrrolidine-2,5-dione;
(R)-1-Methyl-2-[1,2,3]triazol-2-yl-ethylamine;
(R)-1-Methyl-2-[1,2,4]triazol-1-yl-ethylamine;
1-((S)-2-Amino-propyl)-pyrrolidine-2,5-dione;
(S)-1-Methyl-2-[1,2,3]triazol-2-yl-ethylamine;
(S)-1-Methyl-2-[1,2,4]triazol-1-yl-ethylamine; and
(R)-1-Methyl-2-(5-methyl-tetrazol-1-yl)-ethylamine.

Example 6

Synthesis of (4-benzotriazol-1-yl-5-chloro-pyrimidin-2-yl)-cyclohexyl-amine

The synthesis of (4-benzotriazol-1-yl-5-chloro-pyrimidin-2-yl)-cyclohexyl-amine was carried out according to the process shown in Scheme F.

SCHEME F

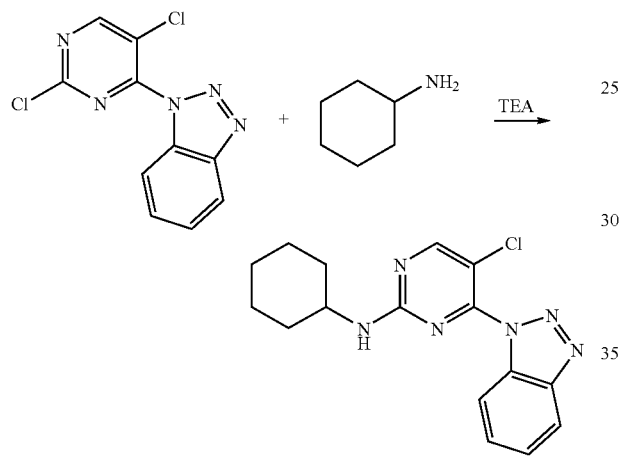

Cyclohexylamine (0.21 mL, 1.88 mmol) was added in portions to a solution of 1-(2,5-dichloro-pyrimidin-4-yl)-1H-benzotriazole (250 mg, 0.94 mmol) in THF (30 mL) at RT under nitrogen atmosphere. The resultant colorless solution was stirred at RT for 4 hours. TEA (2.82 mmol) was then added and the reaction mixture was stirred at RT overnight. The mixture was partitioned between water (50 mL) and EtOAc (50 mL). The organic layer was separated, washed twice with water (50 mL) and once with brine (50 mL), then dried over $Na_2SO_4$, filtered and evaporated under reduced pressure to give an off-white solid. This crude material was purified via flash chromatography (toluene/EtOAc, 98/2) to afford 162 mg (53% yield) of (4-benzotriazol-1-yl-5-chloro-pyrimidin-2-yl)-cyclohexyl-amine as an off-white solid. MS: 329.14 $(M+1)^+$, 301.14 $((M+1)^+–28)$.

The following compounds were prepared using the similar procedure and the appropriate amine and pyrimidine derivatives:
trans-4-(4-Benzotriazol-1-yl-pyrimidin-2-ylamino)-cyclohexanecarbonitrile; MS: 320.15 $(M+1)^+$, 292.18 $((M+1)^+–28)$;
(4-Benzotriazol-1-yl-5-methyl-pyrimidin-2-yl)-cyclohexyl-amine; MS: 309.23 $(M+1)^+$, 281.24 $((M+1)^+–28)$;
(4-Benzotriazol-1-yl-5-fluoro-pyrimidin-2-yl)-cyclohexyl-amine; MS: 313.17 $(M+1)^+$, 285.21 $((M+1)^+–28)$;
3-[(R)-2-(4-Benzotriazol-1-yl-pyrimidin-2-ylamino)-propyl]-5,5-dimethyl-oxazolidine-2,4-dione; MS: 381.94 (M+1), 353.98 ((M+1)–28);
1-[(R)-2-(4-Benzotriazol-1-yl-pyrimidin-2-ylamino)-propyl]-pyrrolidine-2,5-dione; MS: 351.96 (M+1), 324.01 ((M+1)–28);
(4-Benzotriazol-1-yl-pyrimidin-2-yl)-((R)-1-methyl-2-[1,2,3]triazol-2-yl-ethyl)-amine; MS: 321.99 (M+1), 293.98 ((M+1)–28);
(4-Benzotriazol-1-yl-pyrimidin-2-yl)-((R)-1-methyl-2-[1,2,4]triazol-1-yl-ethyl)-amine; MS: 321.99 (M+1), 293.98 ((M+1)–28);
1-[(S)-2-(4-Benzotriazol-1-yl-pyrimidin-2-ylamino)-propyl]-pyrrolidine-2,5-dione; MS: 351.96 (M+1), 324.1 ((M+1)–28);
(4-Benzotriazol-1-yl-pyrimidin-2-yl)-((S)-1-methyl-2-[1,2,3]triazol-2-yl-ethyl)-amine; MS: 321.99 (M+1), 293.98 ((M+1)–28);
(4-Benzotriazol-1-yl-pyrimidin-2-yl)-[(R)-1-methyl-2-(5-methyl-tetrazol-1-yl)-ethyl]-amine; MS: 337.16 $(M+1)^+$, 309.13 $((M+1)^+–28)$; and
(4-Benzotriazol-1-yl-pyrimidin-2-yl)-((S)-1-methyl-2-[1,2,4]triazol-1-yl-ethyl)-amine; MS: 322.17 (M+1), 294.15 ((M+1)–28).

Example 7

Synthesis of trans-4-(4-benzotriazol-1-yl-pyrimidin-2-ylamino)-cyclohexanol

The synthesis of trans-4-(4-benzotriazol-1-yl-pyrimidin-2-ylamino)-cyclohexanol was carried out according to the process shown in Scheme G.

SCHEME G

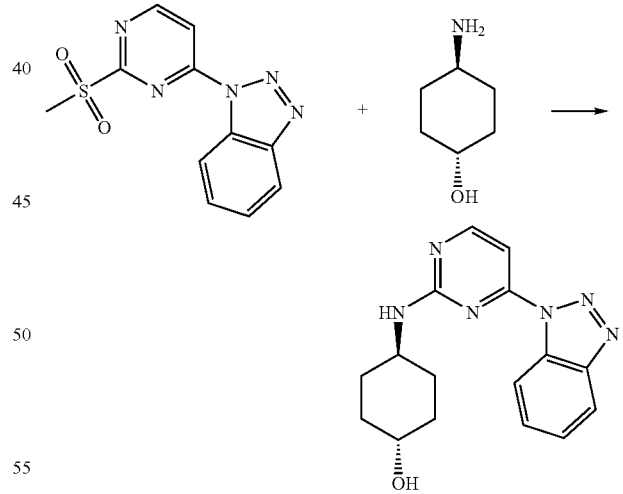

To a solution of 1-(2-methanesulfonyl-pyrimidin-4-yl)-1H-benzotriazole (1.59 g, 6 mmol) in 15 mL of NMP was added trans-4-aminocyclohexane (3.11 g, 27 mmol) and the resulting mixture was stirred at 120° C. for 2 hours. It was then cooled, poured onto 100 mL of water, stirred and allowed to stand overnight. The resulting suspension was filtered, the collected solids were washed with water and dissolved with $CH_2Cl_2$; the solvent was removed under reduced pressure. The solid residue formed was taken up with EtOAc, filtered and dried to give trans-4-(4-benzotriazol-1-yl-pyrimidin-2- ylamino)-cyclohexanol as a white solid (910 mg, 51% yield), mp=224.8-228.1° C.; MS=311 (M+H)⁺.

The following compounds were prepared using a similar procedure and the appropriate amines:

cis-4-(4-Benzotriazol-1-yl-pyrimidin-2-ylamino)-cyclohexanol (white solid); mp=220.0-221.0° C.; MS=311 (M+H)⁺;

trans-2-(4-Benzotriazol-1-yl-pyrimidin-2-ylamino)-cyclohexanol (white crystalline solid); mp=166.9-169.3° C.; MS=311 (M+H)⁺;

(1R,3R)-3-(4-Benzotriazol-1-yl-pyrimidin-2-ylamino)-cyclopentanol (white solid); mp=194.5-196.5° C.; MS=297 (M+H)⁺;

(1S,3S)-3-(4-Benzotriazol-1-yl-pyrimidin-2-ylamino)-cyclopentanol (white solid); mp=194.1-195.9° C.; MS=297 (M+H)⁺;

(4-Benzotriazol-1-yl-pyrimidin-2-yl)-(4-ethyl-cyclohexyl)-amine (white solid); mp=191.2-191.7° C.; MS=323 (M+H)⁺;

(4-Benzotriazol-1-yl-pyrimidin-2-yl)-piperidin-4-yl-amine (white solid, obtained from the standard tert-butyl carbamate deprotection of 4-(4-benzotriazol-1-yl-pyrimdin-2-ylamino)-piperidine-1-carboxylic acid tert-butyl ester; which was obtained using tert-butyl 4-amino-1-piperidinecarboxylate); mp=230.1-233.9° C.; MS=296 (M+H)⁺;

(4-Benzotriazol-1-yl-pyrimidin-2-yl)-(4-methyl-cyclohexyl)-amine (white solid); mp=192.5-196.0° C.; MS=309 (M+H)⁺;

(4-Benzotriazol-1-yl-pyrimidin-2-yl)-(trans-4-methoxy-cyclohexyl)-amine (white solid) (4-methoxy-cyclohexylamine was obtained from 4-methoxy-cyclohexanone oxime as described in J. Org. Chem. (1985) 50:1160, which was obtained from 4-methoxy-cyclohexanone as described in J. Med. Chem. (1977) 20:289, which was obtained from 4-methoxy-cyclohexanol as described in J. Med. Chem. (1989) 32:355); mp=184.0-186.9° C.; MS=325 (M+H)⁺;

N-(4-Benzotriazol-1-yl-pyrimidin-2-yl)-N'-pyrimidin-2-yl-cyclohexane-trans-1,4-diamine (white solid) (N-Pyrimidin-2-yl-cyclohexane-trans-1,4-diamine was prepared as described in Preparation 4); mp=286.0-286.4° C.; MS=388 (M+H)⁺;

N-(4-Benzotriazol-1-yl-pyrimidin-2-yl)-N'-pyrimidin-2-yl-cyclohexane-trans-1,4-diamine bis-methane sulfonate salt which was prepared adding an excess of methanesulfonic acid to a solution of N-(4-Benzotriazol-1-yl-pyrimidin-2-yl)-N'-pyrimidin-2-yl-cyclohexane-trans-1,4-diamine bis-methane (150 mg) in 100 mL of CH₂Cl₂ and approximately 20 mL of MeOH. The resulting mixture was concentrated and recrystallized from CH₂Cl₂/EtOAc. The solid was filtered and dried to give the methanesulfonic acid salt as a white solid (214 mg, 95% yield); mp=282.6-288.9° C.; MS=388 (M+H)⁺.

Similarly, methanesulfonic acid salt of the following compounds were prepared:

(4-Benzotriazol-1-yl-pyrimidin-2-yl)-(1,4-dioxa-spiro[4.5]dec-8-yl)-amine (white solid); mp=207.9-209.0° C.; MS=353 (M+H)⁺;

(4-Benzotriazol-1-yl-pyrimidin-2-yl)-(tetrahydro-pyran-4-yl)-amine (white fine-needle crystals); mp=202.0-202.4° C.; MS=297 (M+H)⁺; and (4-Benzotriazol-1-yl-pyrimidin-2-yl)-(1,1-dioxo-hexahydro-1λ⁶-thiopyran-4-yl)-amine (white powder); mp=268.5-270.2° C.; MS=345 (M+H)⁺.

Example 8

Synthesis of (4-benzotriazol-1-yl-pyrimidin-2-yl)-cyclohexyl-amine

Synthesis of (4-benzotriazol-1-yl-pyrimidin-2-yl)-cyclohexyl-amine was carried out according to the process shown in Scheme H.

SCHEME H

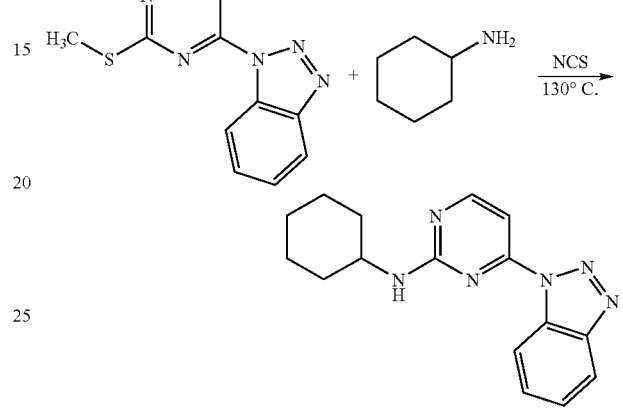

To a solution of 1-(2-methylsulfanyl-pyrimidin-4-yl)-1H-benzotriazole (376 mg, 1.5 mmol) in 4 mL of NMP were added N-chlorosuccinamide (250 mg, 1.9 mmol) and 0.5 mL of water. The mixture was placed in an oil bath at 130° C. for 5-10 minutes, cyclohexylamine (450 mg, 5 mmol) was then added and the reaction mixture was stirred in an oil bath at 130° C. for 30 minutes. The cooled reaction mixture was partitioned between water (40 mL) and EtOAc (40 mL). The organic layer was separated and washed twice with water (40 mL), then dried over Na₂SO₄, filtered and the solvent removed under reduced pressure. The crude residue was purified by flash chromatography and recrystallized from CH₂Cl₂/EtOAc to give (4-benzotriazol-1-yl-pyrimidin-2-yl)-cyclohexyl-amine as a white short-needle crystalline solid (255 mg, 56% yield). mp=202.0-204.0° C.; MS=295 (M+H)⁺.

Example 9

Synthesis of (1S,2R)-[2-(4-benzotriazol-1-yl-pyrimidin-2-ylamino)-cyclohexyl]-methanol Synthesis of (1S,2R)-[2-(4-benzotriazol-1-yl-pyrimidin-2-ylamino)-cyclohexyl]-methanol was carried out according to the process shown in Scheme I.

SCHEME I

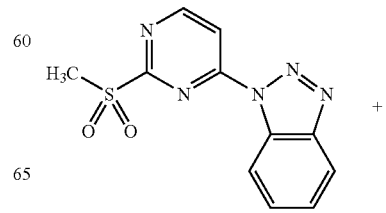

-continued

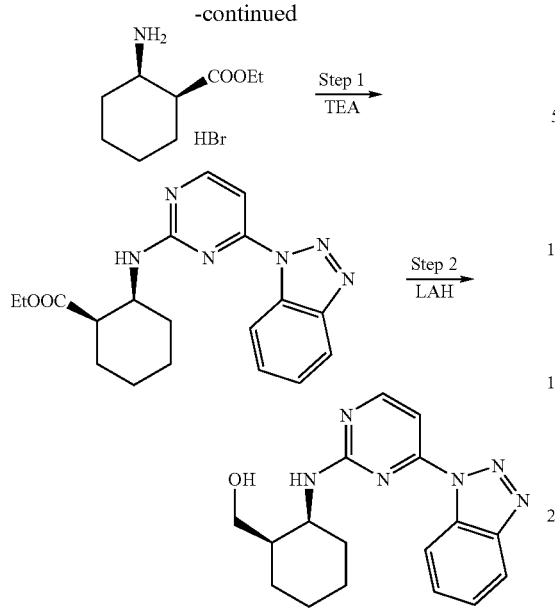

Step 1: Synthesis of cis-(1S,2R)-2-(4-benzotriazol-1-yl-pyrimidin-2-ylamino)-cyclohexane-carboxylic acid ethyl ester (1S,2R)-cis-2-Amino-1-cyclohexanecarboxylic acid ethyl ester hydrobromide (0.41 g, 1.62 mmol) and triethylamine (0.30 mL, 2.16 mmol) were added to a solution of 1-(2-methane-sulfonyl-pyrimidin-4-yl)-1H-benzotriazole (0.30 g, 1.09 mmol) in 2 mL of NMP. The reaction mixture was stirred for 45 minutes at 120° C. and then poured onto 50 mL of ethyl acetate. The organic layer was separated, washed with water, dried over $Na_2SO_4$ and filtered; the solvent was evaporated under reduced pressure. The crude residue was triturated with a solution of methanol and dichloromethane; it was then filtered and dried to give the cis-(1S,2R)-2-(4-benzotriazol-1-yl-pyrimidin-2-ylamino)-cyclohexanecarboxylic acid ethyl ester as an off-white solid (0.22 g, 55% yield); mp=106.3-107.9° C.; MS=367 (M+H)$^+$.

Step 2: Synthesis of (1S,2R)-[2-(4-benzotriazol-1-yl-pyrimidin-2-ylamino)-cyclohexyl]-methanol Lithium aluminum hydride (1.0 M in THF, 0.52 mL, 0.52 mmol) was added dropwise to a −78° C. solution of cis-(1S, 2R)-2-(4-benzotriazole-1-yl-pyrimidin-2-ylamino)-cyclohexane-carboxylic acid ethyl ester (0.19 g, 0.52 mmol) in 5 mL of THF. The reaction mixture was stirred for 2 hours, then warmed to RT over a period of 10 minutes. After a standard Fieser work-up (1:1:3 $H_2O$, 15% NaOH, $H_2O$), the reaction mixture was allowed to stir at RT for about 18 hours. Ethyl acetate was added and the mixture was filtered. The filtrate was concentrated under reduced pressure, and the crude residue dissolved in chloroform, filtered through a pad of celite, concentrated under reduced pressure, and dried to give (1S, 2R)-[2-(4-benzotriazol-1-yl-pyrimidin-2-ylamino)-cyclohexyl]-methanol as a white solid (0.04 g, 24% yield); mp=206.1-207.8° C.; MS=325 (M+H)$^+$.

trans-[4-(4-Benzotriazol-1-yl-pyrimidin-2-ylamino)-cyclohexyl]-methanol was prepared in a similar manner using the appropriate aminoester; MS: 325.19 (M+1)$^+$, 297.17 ((M+1)$^+$−28).

Example 10

Synthesis of N-(4-Benzotriazol-1-yl-pyrimidin-2-yl)-cyclohexane-trans-1,4-diamine Synthesis of N-(4-Benzotriazol-1-yl-pyrimidin-2-yl)-cyclohexane-trans-1,4-diamine was carried out according to the process shown in Scheme J.

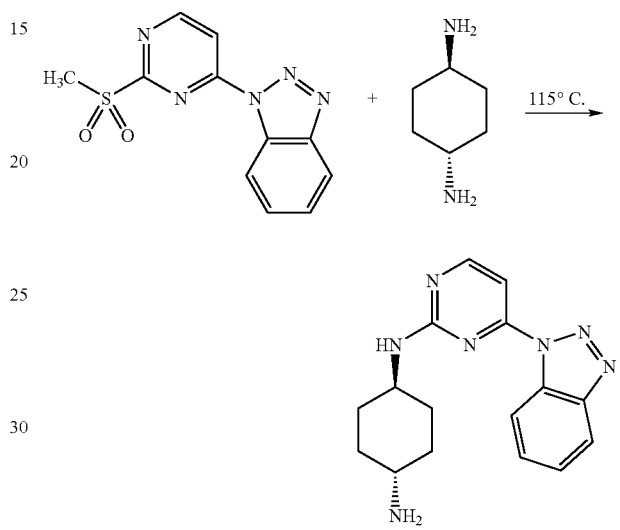

SCHEME J

A warm solution of 1-(2-methanesulfonyl-pyrimidin-4-yl)-1H-benzotriazole (10.07 g, 37 mmol) in 80 mL of NMP was added dropwise over a 10 minutes period via addition funnel to a 115° C. solution of trans-1,4-diaminocyclohexane (25.58 g, 224 mmol) in 100 mL of NMP. The reaction mixture was stirred for 1.5 hour in an oil bath at 115-120° C.; then it was slowly cooled to RT overnight. The reaction mixture was poured into 300 mL of water and stirred for 4 hours; it was then extracted twice with EtOAc (400 mL). The combined organic extracts were washed once with water (the product is water soluble), dried over $Na_2SO_4$ and filtered. The solvent was evaporated under reduced pressure until the product began to crystallize out. The solid was filtered, washed with EtOAc/hexanes and dried to give the first crop of the title compound. Additional crops were obtained in a similar manner from the mother liquors to give a total of 6.47 g (57% yield) of N-(4-benzotriazol-1-yl-pyrimidin-2-yl)-cyclohexane-trans-1,4-diamine as an off-white solid; mp=223.5-227.8° C.; MS=310 (M+H)$^+$.

Example 11

Synthesis of N-[trans-4-(4-Benzotriazol-1-yl-pyrimidin-2-ylamino)-cyclohexyl]-acetamide Synthesis of N-[trans-4-(4-Benzotriazol-1-yl-pyrimidin-2-ylamino)-cyclohexyl]-acetamide was carried out according to the process shown in Scheme K.

SCHEME K

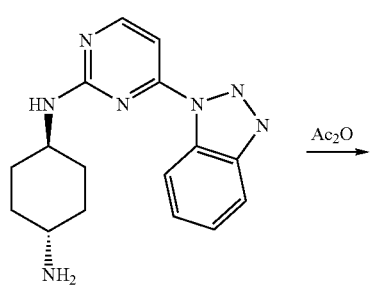

To a suspension of N-(4-benzotriazol-yl-pyrimidin-2-yl)-cyclohexane-trans-1,4-diamine (0.22 g, 0.71 mmol) in 1.5 mL NMP was added acetic anhydride (0.13 mL, 1.38 mmol). The reaction was stirred for 1 hour. Ethyl acetate was added to the suspension and the resulting mixture was stirred for 10 minutes. The precipitate was filtered, triturated with dichloromethane, and dried to give N-[trans-4-(4-benzotriazol-1-yl-pyrimidin-2-ylamino)-cyclohexyl]-acetamide as a white solid (0.18 g, 74% yield); mp=286.6-287.6° C.; MS=352 (M+H)+.

The following compounds were similarly prepared, using the appropriate acylating agent:

N-[trans-4-(4-Benzotriazol-1-yl-pyrimidin-2-ylamino)-cyclohexyl]-acetamide mesylate (white solid); mp=202.2-206.6° C.; MS=352 (M+H)+;

N-[trans-4-(4-Benzotriazol-1-yl-pyrimidin-2-ylamino)-cyclohexyl]-methanesulfonamide (white solid); mp=279.2-280.0° C.; MS=388 (M+H)+;

Methanesulfonate(4-benzotriazol-1-yl-pyrimidin-2-yl)-(4-methanesulfonylamino-cyclohexyl)-ammonium (white solid, 161 mg, 90% yield); mp=252.3-256.6° C.; MS=388 (M+H)+;

N-[trans-4-(4-Benzotriazol-1-yl-pyrimidin-2-ylamino)-cyclohexyl]-propionamide (white solid); mp=293.0-294.3° C.; MS=366 (M+H)+;

Ethanesulfonic acid [trans-4-(4-benzotriazol-1-yl-pyrimidin-2-ylamino)-cyclohexyl]-amide (white solid); mp=282.1-287.3° C.; MS=402 (M+H)+;

Dimethylsulfamic acid [trans-4-(4-benzotriazol-1-yl-pyrimidin-2-yl-amino)-cyclohexyl]amide (white solid); mp=242.0-244.0° C.; MS=417 (M+H)+; and 2-[4-(4-Benzotriazol-1-yl-pyrimidin-2-ylamino)-piperidin-1-yl]-acetamide (off-white solid); mp=247.9-249.3° C.; MS=353 (M+H)+.

Example 12

Synthesis of N-[trans-4-(4-benzotriazol-1-yl-pyrimidin-2-ylamino)-cyclohexyl]-N-methyl-acetamide Synthesis of N-[trans-4-(4-benzotriazol-1-yl-pyrimidin-2-ylamino)-cyclohexyl]-N-methyl-acetamide was carried out according to the process shown in Scheme L.

SCHEME L

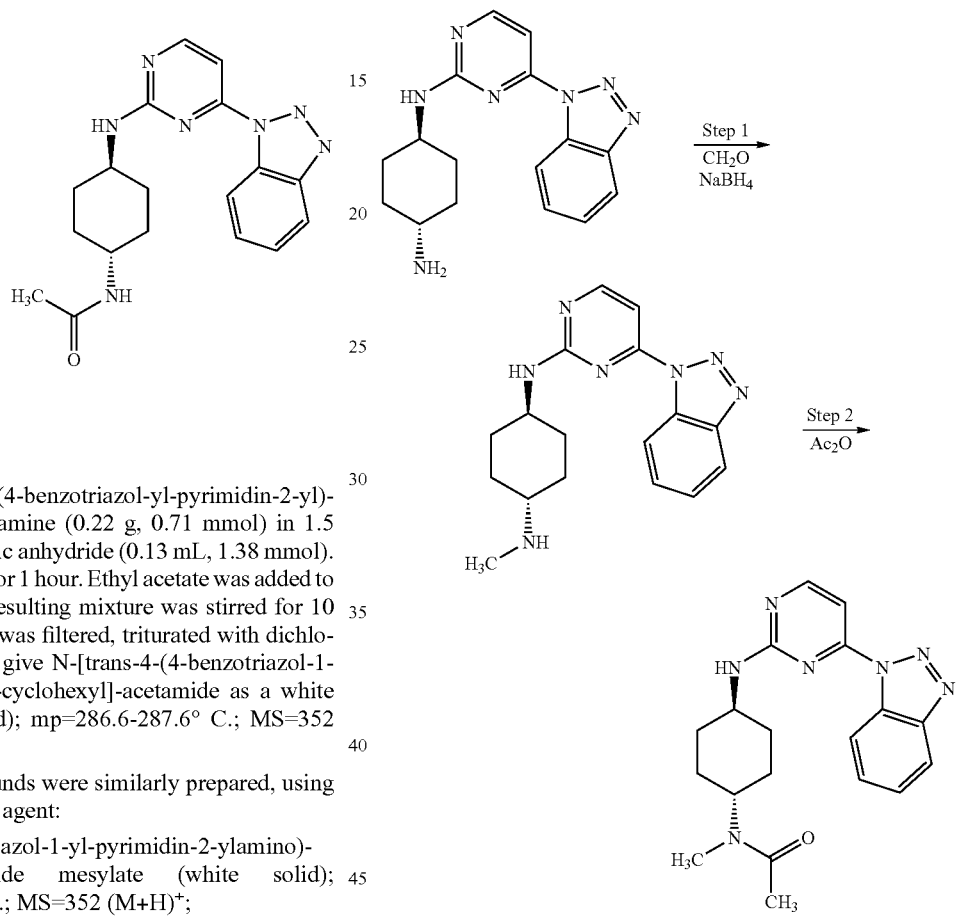

Step 1: Synthesis of (4-benzotriazol-yl-pyrimidin-2-yl)-N'-methyl-cyclohexane-trans-1,4-diamine A suspension of N-4-benzotriazol-yl-pyrimidin-2-yl)-cyclohexane-trans-1,4-diamine (0.30 g, 0.97 mmol), formaldehyde (0.5 mL, 37% in water, 0.87 mmol) and methanol (5 mL) was stirred for 4 hours at RT under nitrogen atmosphere. Sodium borohydride (0.06 g, 1.59 mmol) was added portionwise and the suspension was stirred for 1 hour. A solution of sodium hydroxide (1 M, 10 mL) was added. The reaction mixture was cooled in a 25° C. water bath and stirred for 30 minutes. Ethyl acetate (50 mL) was added and the resulting mixture was stirred for 5 minutes, then filtered. The organic layer of the filtrate was discarded. The aqueous layer was extracted with EtOAc; the organic layer was separated; dried over Na$_2$SO$_4$ and filtered; the solvent was evaporated under reduced pressure. The crude solid was purified by flash column chromatography using 15% MeOH/CH$_2$Cl$_2$ to give (4-benzotriazol-yl-pyrimidin-2-yl)-N'-methyl-cyclohexane-trans-1,4-diamine as a solid (0.05 g, 16% yield). MS=324 (M+H)+.

Step 2: Synthesis of N-[trans-4-(4-benzotriazol-1-yl-pyrimidin-2-ylamino)-cyclohexyl]-N-methyl-acetamide The title compound was obtained as an off-white powder in a similar manner as described in Example 11 from (4-benzotriazol-yl-pyrimidin-2-yl)-N'-methyl-cyclohexane-trans-1,4-diamine. MS=366 (M+H)+.

N-[trans-4-(4-Benzotriazol-1-yl-pyrimidin-2-ylamino)-cyclohexyl]-N-methyl-methanesulfonamide (off-white solid) was prepared in a similar manner using methanesulfonyl chloride; mp=249.9-251.7° C.; MS=402 (M+H)+.

Example 13

Synthesis of N-(4-benzotriazol-1-yl-pyrimidin-2-yl)-N'-pyridin-2-yl-cyclohexane-trans-1,4-diamine hydrochloride Synthesis of N-(4-benzotriazol-1-yl-pyrimidin-2-yl)-N'-pyridin-2-yl-cyclohexane-trans-1,4-diamine hydrochloride was carried out according to the process shown in Scheme M.

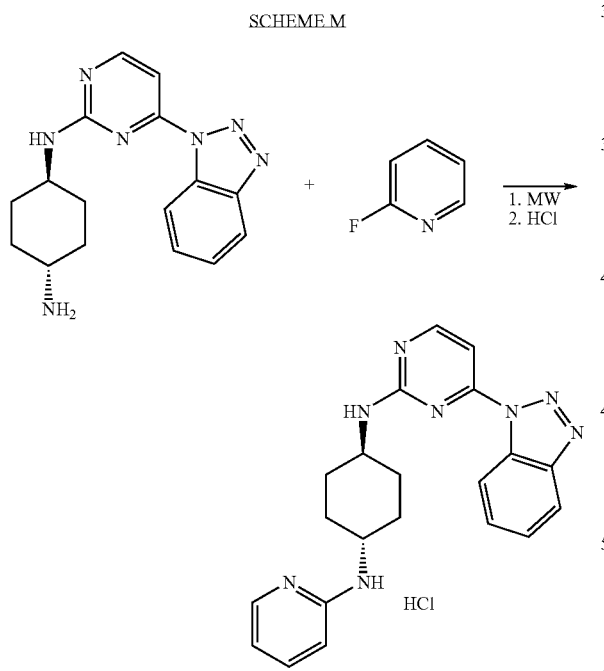

SCHEME M

A solution of N-(4-benzotriazol-yl-pyrimidin-2-yl)-cyclohexane-trans-1,4-diamine (0.20 g, 0.65 mmol) and 2-fluoropyridine (0.11 mL, 1.28 mmol) 1.5 mL NMP was heated in a microwave reactor at 230° C. for 20 minutes. The NMP was removed by distillation. The solid was washed with saturated sodium bicarbonate, triturated with ether, and purified by preparative TLC. The free base obtained in this manner was transformed into the corresponding hydrochloride salt by addition of HCl in ether to give the title compound as a yellow solid (0.04 g, 16% yield); mp=207.0-210.0° C. MS=387 (M+H)+.

Example 14

Synthesis of N-{trans-4-[(4-benzotriazol-1-yl-pyrimidin-2-yl)-methyl-amino]-cyclohexyl}-N-methyl-methanesulfonamide Synthesis of N-{trans-4-[(4-benzotriazol-1-yl-pyrimidin-2-yl)-methyl-amino]-cyclo-hexyl}-N-methyl-methanesulfonamide was carried out according to the process shown in Scheme N.

SCHEME N

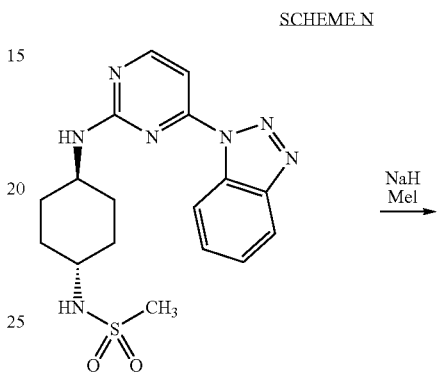

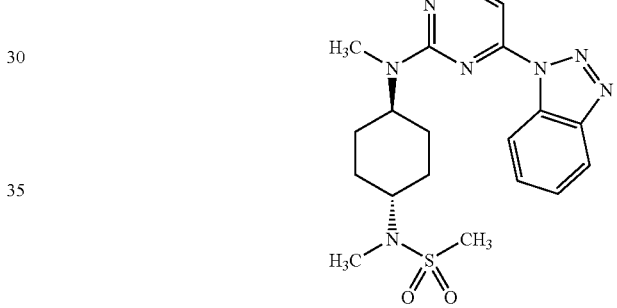

To a solution of N-[trans-4-(4-benzotriazol-1-yl-pyrimidin-2-ylamino)-cyclohexyl]-methanesulfonamide (0.13 g, 0.3 mmol) in 4 mL of NMP was added an excess of NaH (dispersion in mineral oil). Immediately the mixture turned yellow in color and the reaction appeared to be slightly exothermic; it was then stirred at RT for 10-15 minutes, then a couple of drops of iodomethane were added. The yellow color faded and the reaction mixture was stirred for 15 minutes. It was then poured into 100 mL of water and extracted with 100 mL of EtOAc. The organic layer was separated and washed twice with 100 mL of water; it was then dried over Na2SO4 and filtered. The solvent was evaporated under reduced pressure and the crude residue was purified by flash chromatography (EtOAc/hexanes, 1:1). Recrystallization from EtOAc/hexanes gave the title product as a white solid (51 mg, 37% yield); mp=203.5-204.0° C.; MS=416 (M+H)+.

Example 15

Synthesis of 1-[trans-4-(4-benzotriazol-1-yl-pyrimidin-2-ylamino)-cyclohexyl]-pyrrolidine-2,5-dione Synthesis of 1-[trans-4-(4-benzotriazol-1-yl-pyrimidin-2-ylamino)-cyclohexyl]-pyrrolidine-2,5-dione was carried out according to the process shown in Scheme O.

SCHEME O

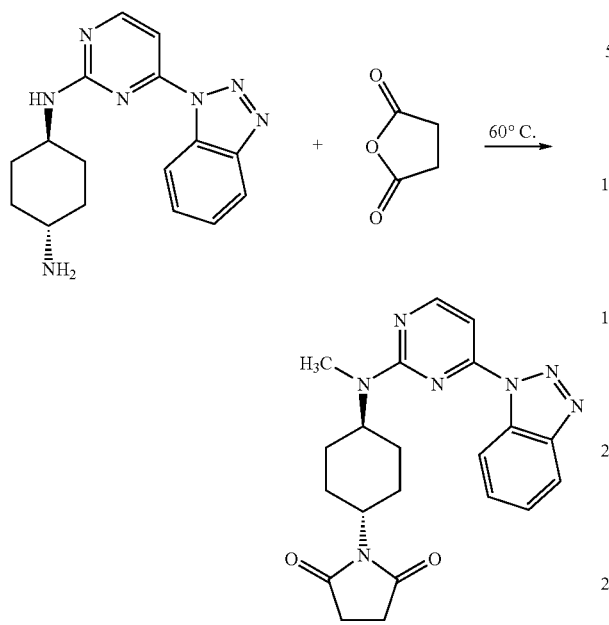

A solution of N-(4-benzotriazol-yl-pyrimidin-2-yl)-cyclohexane-trans-1,4-diamine (0.26 g, 0.8 mmol) and succinic anhydride (0.09 g, 0.9 mmol) in 2 mL of NMP was placed in a reaction tube, sealed then heated to 60-65° C. for 17 hours. The cooled reaction mixture was concentrated and treated with 8 mL of acetic anhydride and sodium acetate (0.09 g, 1.10 mmol). The mixture was heated to reflux and stirred for 21 hours. The reaction mixture was poured onto ice cold water and neutralized with 1 M sodium hydroxide. The precipitate was filtered and purified by preparative TLC to give the title compound as a white solid (0.07 g, 21% yield). mp=205.0-210.0° C.; MS=392 (M+H)⁺.

Example 16

Synthesis of 4-(4-benzotriazol-1-yl-pyrimidin-2-ylamino)-cyclohexanone

Synthesis of 4-(4-benzotriazol-1-yl-pyrimidin-2-ylamino)-cyclohexanone was carried out according to the process shown in Scheme P.

SCHEME P

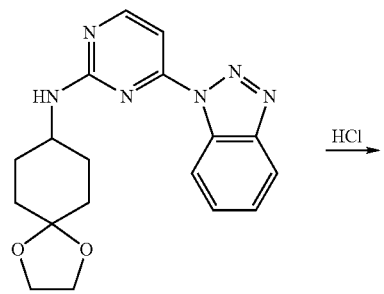

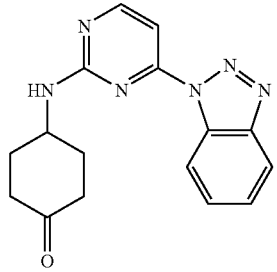

To a suspension of (4-benzotriazol-1-yl-pyrimidin-2-yl)-(1,4-dioxa-spiro[4.5]dec-8-yl)-amine (prepared in a similar manner as described in Example 2) (1.53 g, 4 mmol) in 80 mL of THF was added 25 mL of a 3 M aqueous solution of HCl. The reaction mixture was stirred at RT for 20 minutes. The reaction was heated to reflux for 30 minutes. It was then cooled, and poured onto an aqueous NaHCO₃ solution. The resulting mixture was extracted with EtOAc, dried over Na₂SO₄ and filtered. The solvent was evaporated under reduced pressure until the product began to crystallize out of solution; it was then filtered and dried to give the title product as a white powder (942 mg, 70% yield); mp=204.9-206.5° C.; MS=309 (M+H)⁺.

Example 17

Synthesis of 4-(4-benzotriazol-1-yl-pyrimidin-2-ylamino)-1-methyl-cyclohexanol

Synthesis of 4-(4-benzotriazol-1-yl-pyrimidin-2-ylamino)-1-methyl-cyclohexanol was carried out according to the process shown in Scheme Q.

SCHEME Q

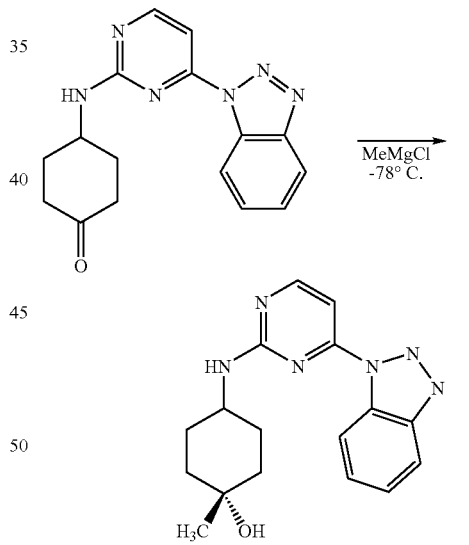

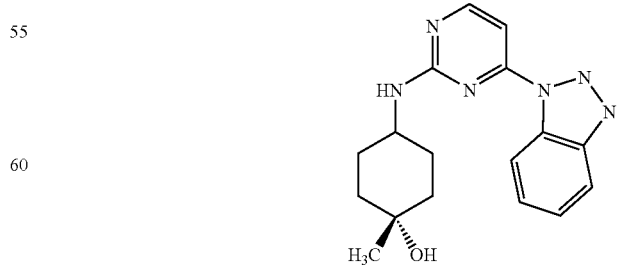

To a solution of 4-(4-benzotriazol-1-yl-pyrimidin-2-ylamino)-cyclohexanone (764 mg, 2.5 mmol) in 80 mL of THF, cooled at −78° C., was added dropwise methylmagnesium chloride (3.5 mL, 3.0 M in THF, 10.5 mmol). The reaction mixture immediately turned bright yellow in color; it was then allowed to warm to RT. The reaction did not reach completion, so it was re-cooled to −78° C. and an additional aliquot of MeMgCl (3 mL, 9 mmol) was added. The resulting mixture was warmed to RT and then poured onto an aqueous solution of $NH_4Cl$; it was extracted with EtOAc. The organic layer was separated, dried over $Na_2SO_4$ and filtered; the solvent was evaporated under reduced pressure. The crude residue was purified by column chromatography (1-5/99-95 MeOH/$CH_2Cl_2$) to give: a less polar trans-isomer (130 mg, 16% yield, mp=193.0-195.4° C.; MS=325 (M+H)$^+$), and the more polar cis-isomer (360 mg, 45% yield, mp=202.1-205.6° C.; MS=325 (M+H)$^+$) as white crystalline solids.

Example 18

Synthesis of trans-4-(4-benzotriazol-1-yl-5-chloro-pyrimidin-2-ylamino)-cyclohexanecarboxylic acid Synthesis of trans-4-(4-benzotriazol-1-yl-5-chloro-pyrimidin-2-ylamino)-cyclohexane-carboxylic acid was carried out according to the process shown in Scheme R.

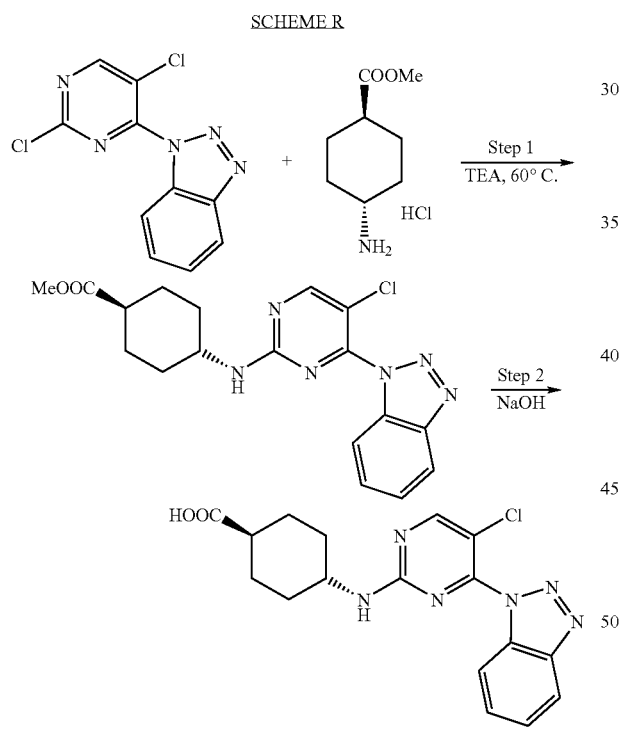

SCHEME R

Step 1: Synthesis of 4-(4-benzotriazol-1-yl-5-chloro-pyrimidin-2-ylamino)-cyclohexane-carboxylic acid methyl ester trans-4-Amino-cyclohexanecarboxylic acid methyl ester (727 mg, 3.76 mmol) was added in portions, at RT under nitrogen atmosphere, to a solution of 1-(2,5-dichloro-pyrimidin-4-yl)-1H-benzotriazole (500 mg, 1.88 mmol) in THF (50 mL) followed by TEA (0.79 mL, 5.64 mmol). The resultant white suspension was stirred at RT overnight, and then at 60° C. for 2.5 days. The mixture was partitioned between water (100 mL) and EtOAc (100 mL). The organic layer was separated, washed twice with water (100 mL) and once with brine (100 mL), then dried over $Na_2SO_4$, filtered and the solvent evaporated under reduced pressure to give an off-white solid. This crude material was purified via flash chromatography (toluene/EtOAc, 90/10) to afford 538 mg (74% yield) of 4-(4-benzotriazol-1-yl-5-chloro-pyrimidin-2-ylamino)-cyclohexanecarboxylic acid methyl ester as an off-white solid. MS: 387.10 (M+1)$^+$, 359.13 ((M+1)$^+$−28).

The following compounds were similarly prepared using the appropriate pyrimidine:
trans-4-(4-Benzotriazol-1-yl-5-fluoro-pyrimidin-2-ylamino)-cyclohexanecarboxylic acid methyl ester; MS: 371.12 (M+1)$^+$, 343.14 ((M+1)$^+$−28);
trans-4-(4-Benzotriazol-1-yl-5-methyl-pyrimidin-2-ylamino)-cyclohexanecarboxylic acid methyl ester; MS: 367.20 (M+1)$^+$, 339.23 ((M+1)$^+$−28); and
trans-4-(4-Benzotriazol-1-yl-pyrimidin-2-ylamino)-cyclohexanecarboxylic acid methyl ester; MS: 353.21 (M+1)$^+$, 325.19 ((M+1)$^+$−28).

Step 2: Synthesis of trans-4-(4-benzotriazol-1-yl-5-chloro-pyrimidin-2-ylamino)-cyclohexane-carboxylic acid An aqueous solution of NaOH (2 M, 10 mL) was added to a colorless solution of 4-(4-benzotriazol-1-yl-5-chloro-pyrimidin-2-ylamino)-cyclohexanecarboxylic acid methyl ester (482 mg, 1.25 mmol) in THF (10 mL) at RT. The reaction mixture was stirred at RT overnight; it was then diluted with water (15 mL) and acidified until pH 3 by addition of HCl (2 M). The white precipitate formed was collected by filtration, washed with water and air dried to give 435 mg (85% yield) of trans-4-(4-benzotriazol-1-yl-5-chloro-pyrimidin-2-ylamino)-cyclohexane-carboxylic acid as a white solid. MS: 373.12 (M+1)$^+$, 345.15 ((M+1)$^+$−28).

The following compounds were similarly prepared using the appropriate pyrimidine:
trans-4-(4-Benzotriazol-1-yl-pyrimidin-2-ylamino)-cyclohexanecarboxylic acid; MS: 339.21 (M+1)$^+$, 311.21 ((M+1)$^+$−28); and
trans-4-(4-Benzotriazol-1-yl-5-fluoro-pyrimidin-2-ylamino)-cyclohexanecarboxylic acid; MS: 357.12 (M+1)$^+$, 329.15 ((M+1)$^+$−28).

Example 19

Synthesis of trans-4-(4-benzotriazol-1-yl-5-chloro-pyrimidin-2-ylamino)-cyclohexanecarboxylic acid ethylamide Synthesis of trans-4-(4-benzotriazol-1-yl-5-chloro-pyrimidin-2-ylamino)-cyclohexane-carboxylic acid ethylamide was carried out according to the process shown in Scheme S.

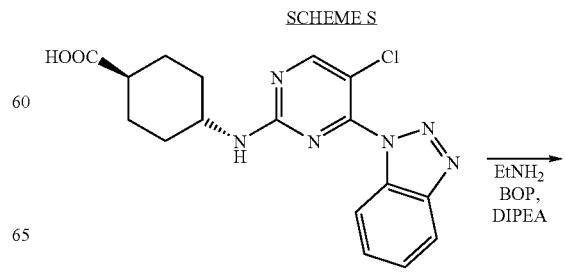

SCHEME S

-continued

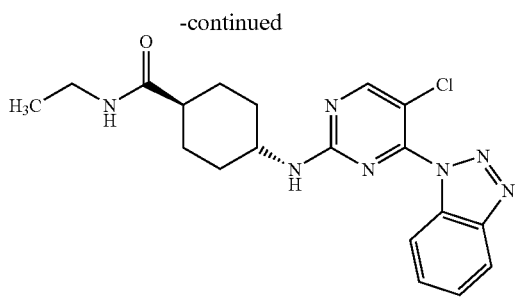

A mixture of trans-4-(4-benzotriazol-1-yl-5-chloro-pyrimidin-2-ylamino)-cyclohexane-carboxylic acid (70 mg, 0.17 mmol), ethyl amine (21 µL, 0.26 mmol), BOP (114 mg, 0.26 mmol) and DIPEA (59 µL, 0.34 mmol) in THF (60 mL) was stirred at RT for 2 days. The white solid formed was removed by filtration and the filtrate was diluted with water (25 mL) and extracted 3 times with a mixture isopropanol/chloroform (1/1, 20 mL). The combined organic extracts were dried over $Na_2SO_4$, filtered and evaporated under reduced pressure to give an off white residue that was purified via flash chromatography (DCM/MeOH, 98/2) to afford 68 mg (quantitative yield) of trans-4-(4-benzotriazol-1-yl-5-chloro-pyrimidin-2-ylamino)-cyclohexane-carboxylic acid ethylamide as a white solid. MS: 400.17 (M+1)$^+$, 372.17 ((M+1)$^+$−28). 1H NMR (250 MHz, CD$_3$OD) δ ppm: 8.55 (1 H, s), 8.09-8.21 (2 H, m), 7.69 (1 H, dd, J=7.50 Hz), 7.55 (1 H, dd, J=7.50 Hz), 3.71-3.88 (1 H, m), 3.18 (2 H, q, J=7.29 Hz), 2.10-2.25 (3 H, m), 1.82-1.95 (2 H, m), 1.50-1.71 (2 H, m), 1.26-1.48 (2 H, m), 1.10 (3 H, t, J=7.29 Hz).

The following compounds were similarly prepared using the appropriate amine and pyrimidine derivatives:

- trans-[4-(4-Benzotriazol-1-yl-pyrimidin-2-ylamino)-cyclohexyl]-(4-methyl-piperazin-1-yl)-methanone; $^1$H NMR (400 MHz, MeOD) δ ppm 8.54-8.99 (1 H, bd), 8.44 (1H, d, J=5.38 Hz), 8.11 (1 H, d, J=8.31 Hz), 7.70 (1 H, m), 7.55 (1 H, m), 7.44 (1H, d, J=5.38 Hz), 4.15-4.29 (1 H, m), 3.70-4.10 (2 H, m), 3.14-3.39 (6 H, m), 2.90 (3H, s), 2.83-2.94 (1 H, m), 2.00-2.13 (2 H, m), 1.80-1.99 (4 H, m), 1.65-1.77 (2 H, m);
- trans-4-(4-Benzotriazol-1-yl-pyrimidin-2-ylamino)-cyclohexanecarboxylic acid cyclopropylamide; MS: 378.22 (M+1)$^+$, 350.22 ((M+1)$^+$−28);
- trans-[4-(4-Benzotriazol-1-yl-pyrimidin-2-ylamino)-cyclohexyl]-pyrrolidin-1-yl-methanone; MS: 391.21 (M+1)$^+$;
- trans-4-(4-Benzotriazol-1-yl-pyrimidin-2-ylamino)-cyclohexanecarboxylic acid (2-hydroxy-ethyl)-amide; MS: 382.18 (M+1)$^+$; cis-[4-(4-Benzotriazol-1-yl-pyrimidin-2-ylamino)-cyclohexyl]-(4-methyl-piperazin-1-yl)-methanone; MS: 421.23 (M+1)$^+$;
- trans-4-(4-Benzotriazol-1-yl-pyrimidin-2-ylamino)-cyclohexanecarboxylic acid (tetrahydro-pyran-4-yl)-amide; MS: 422.24 (M+1)$^+$;
- trans-4-(4-Benzotriazol-1-yl-pyrimidin-2-ylamino)-cyclohexanecarboxylic acid (2-hydroxy-ethyl)-methyl-amide; MS: 396.12 (M+1)$^+$;
- trans-[4-(4-Benzotriazol-1-yl-pyrimidin-2-ylamino)-cyclohexyl]-morpholin-4-yl-methanone; MS: 408.26 (M+1)$^+$;
- trans-4-(4-Benzotriazol-1-yl-pyrimidin-2-ylamino)-cyclohexanecarboxylic acid (2-amino-2-methyl-propyl)-amide; MS: 409.27 (M+1)$^+$;
- trans-4-(4-Benzotriazol-1-yl-pyrimidin-2-ylamino)-cyclohexanecarboxylic acid ethylamide; MS: 366.19 (M+1)$^+$, 338.23 ((M+1)$^+$−28);
- trans-[4-(4-Benzotriazol-1-yl-5-fluoro-pyrimidin-2-ylamino)-cyclohexyl]-morpholin-4-yl-methanone; MS: 426.15 (M+1)$^+$, 398.14 ((M+1)$^+$−28);
- trans-[4-(4-Benzotriazol-1-yl-5-methyl-pyrimidin-2-ylamino)-cyclohexyl]-morpholin-4-yl-methanone; MS: 422.18 (M+1)$^+$, 394.15 ((M+1)$^+$−28);
- trans-4-(4-Benzotriazol-1-yl-5-fluoro-pyrimidin-2-ylamino)-cyclohexanecarboxylic acid ethylamide; MS: 384.15 (M+1)$^+$, 356.17 ((M+1)$^+$−28); and
- trans-4-(4-Benzotriazol-1-yl-5-methyl-pyrimidin-2-ylamino)-cyclohexanecarboxylic acid ethylamide; MS: 380.18 (M+1)$^+$, 352.21 ((M+1)$^+$−28).

Example 20

Synthesis of trans-(4-aminomethyl-cyclohexyl)-(4-benzotriazol-1-yl-pyrimidin-2-yl)-amine Synthesis of trans-(4-aminomethyl-cyclohexyl)-(4-benzotriazol-1-yl-pyrimidin-2-yl)-amine was carried out according to the process shown in Scheme T.

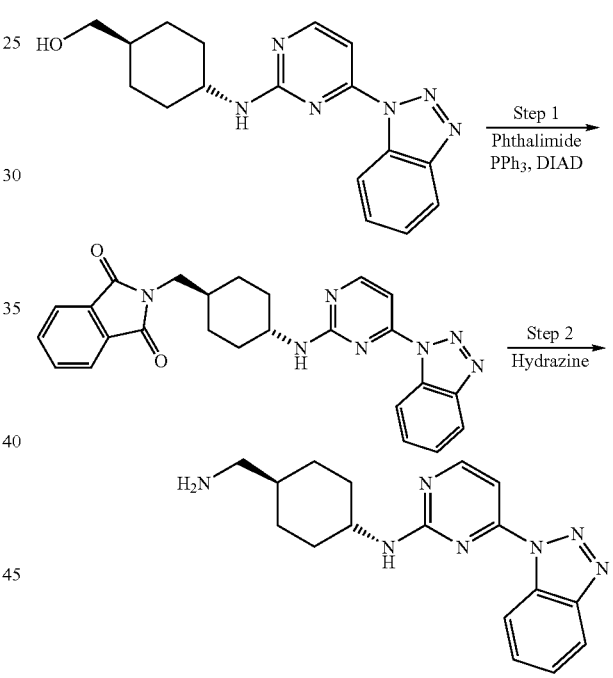

Step 1: Synthesis of trans-2-[4-(4-Benzotriazol-1-yl-pyrimidin-2-ylamino)-cyclohexylmethyl]-isoindole-1,3-dione Triphenylphosphine (972 mg, 1.2 eq) was added to a solution of trans-[4-(4-benzotriazol-1-yl-pyrimidin-2-ylamino)-cyclohexyl]-methanol (1 g, 1 equivalent; prepared in a similar manner as described in Example 4) in toluene (100 mL), it was then followed by the dropwise addition of DIAD (0.73 mL, 1.2 eq). The reaction mixture was stirred at RT for 10 minutes and then phthalimide (545 mg, 1.2 eq) was added. The mixture was stirred overnight at RT, water was then added and the resulting mixture was extracted 3 times with EtOAc. The combined organic extracts were dried over $Na_2SO_4$, filtered and the solvent was evaporated under reduced pressure. The crude residue was triturated with MeOH to give 976 mg (70% yield) of trans-2-[4-(4-benzotriazol-1-yl-pyrimidin-2-ylamino)-cyclohexylmethyl]-isoindole-1,3-dione; MS=454.40 (M+1)⁺.

trans-4-[4-(4-Benzotriazol-1-yl-pyrimidin-2-ylamino)-cyclohexylmethyl]-morpholine-3,5-dione was prepared in a similar manner using the appropriate imide; MS: 422.35 (M+1)⁺.

Step 2: Synthesis of trans-(4-aminomethyl-cyclohexyl)-(4-benzotriazol-1-yl-pyrimidin-2-yl)-amine Hydrazine monohydrate (0.28 mL, 2.7 eq) was added to a solution of trans-2-[4-(4-benzotriazol-1-yl-pyrimidin-2-ylamino)-cyclohexylmethyl]-isoindole-1,3-dione (976 mg, 1 equivalent) in EtOH (60 mL). The reaction mixture was stirred overnight at 70° C., a second aliquot of hydrazine monohydrate (0.22 mL, 2.0 eq) was then added and the mixture was stirred at reflux for 7 hours. The solvent was then evaporated under reduced pressure, the residue was dissolved in a mixture of isopropanol and chloroform and it was acidified until pH 3 by the addition of HCl (1 M). The organic phase was washed 3 times with water. The aqueous phase was basified to pH 8-9 by the addition of NaOH (1 M) and it was extracted 5 times with a mixture of isopropanol and chloroform. The combined organic extracts were dried over $Na_2SO_4$, filtered and the solvent was evaporated under reduced pressure. This acid/base extraction procedure was repeated 3 times in order to remove phthalazinone. trans-(4-Aminomethyl-cyclohexyl)-(4-benzotriazol-1-yl-pyrimidin-2-yl)-amine was obtained in 71% purity (450 mg, 65% yield). ¹H NMR (400 MHz, $CD_3OD$) δ ppm 8.53-8.85 (1 H, bd), 8.40 (1 H, d, J=5.50 Hz), 8.09 (1 H, d, J=8.31 Hz), 7.67 (1 H, m), 7.53 (1 H, m), 7.39 (1 H, d, J=5.50 Hz), 3.76-3.89 (1 H, m), 2.60 (2 H, d, J=6.60 Hz), 2.11-2.28 (2 H, m), 1.88-2.02 (2 H, m), 1.08-1.54 (5 H, m).

Example 21

Synthesis of trans-N-[4-(4-benzotriazol-1-yl-pyrimidin-2-ylamino)-cyclohexyl-methyl]-acetamide Synthesis of trans-N-[4-(4-benzotriazol-1-yl-pyrimidin-2-ylamino)-cyclohexylmethyl]-acetamide was carried out according to the process shown in Scheme U.

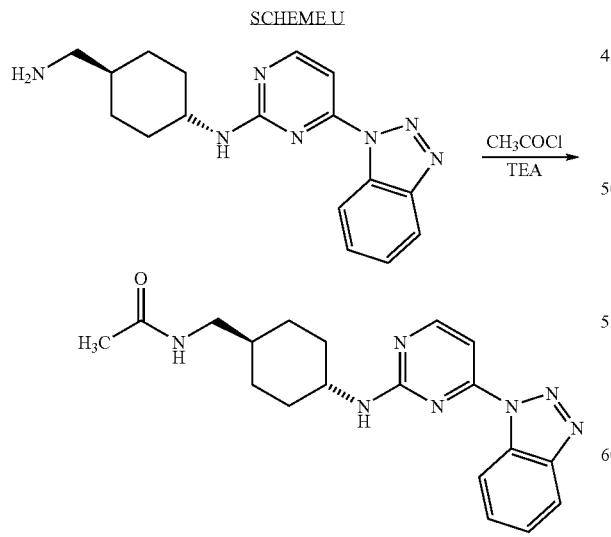

TEA (52 µL, 0.37 mmol) was added, under nitrogen atmosphere, to a solution of trans-(4-aminomethyl-cyclohexyl)-(4-benzotriazol-1-yl-pyrimidin-2-yl)-amine (60 mg, 0.185 mmol) in DCM (3 mL). The mixture was cooled to −78° C. and acetyl chloride (13.2 µL, 0.185 mmol) was added. The reaction mixture was stirred at RT overnight; it was then poured in water and extracted 3 times with a mixture of isopropanol and chloroform. The combined organic extracts were dried over $Na_2SO_4$, filtered and the solvent was evaporated under reduced pressure. The crude residue was purified via preparative TLC to give 10 mg of trans-N-[4-(4-benzotriazol-1-yl-pyrimidin-2-ylamino)-cyclohexylmethyl]-acetamide. ¹H NMR (400 MHz, $CDCl_3$) δ ppm 8.55 (1 H, d, J=8.19 Hz), 8.41 (1 H, d, J=5.14 Hz), 8.12 (1 H, d, J=8.19 Hz), 7.57-7.67 (1 H, m), 7.42-7.51 (2 H, m), 7.16-7.24 (0.3 H, m), 5.55-5.64 (0.7 H, m), 5.18-5.43 (1 H, m), 3.80-3.93 (1 H, m), 3.11-3.25 (2 H, m), 2.27 (1 H, s), 2.19-2.35 (2 H, m), 2.00 (2 H, s), 1.85-1.95 (2 H, m), 1.50-1.63 (1 H, m), 1.11-1.37 (4 H, m).

trans-N—N'-[4-(4-benzotriazol-1-yl-pyrimidin-2-ylamino)-cyclohexylmethyl]-dimethyl-sulfanoyl urea was prepared in a similar manner using dimethylsulfamoyl chloride as the acylating agent. ¹H NMR (400 MHz, $CDCl_3$) δ ppm 8.52 (1 H, d, J=8.19 Hz), 8.34-8.42 (1H, bd), 8.11 (1 H, d, J=8.19 Hz), 7.60 (1 H, m), 7.41-7.51 (2 H, m), 3.75-3.89 (1 H, m), 2.94 (2H, d, J=6.36 Hz), 2.79 (6 H, s), 2.20-2.33 (2 H, m), 1.86-2.00 (2 H, m), 1.48-1.62 (1 H, m), 1.09-1.39 (4 H, m).

Example 22

Synthesis of (4-benzotriazol-1-yl-pyrimidin-2-yl)-(4-morpholin-4-ylmethyl-cyclohexyl)-amine Synthesis of (4-benzotriazol-1-yl-pyrimidin-2-yl)-(4-morpholin-4-ylmethyl-cyclohexyl)-amine was carried out according to the process shown in Scheme V.

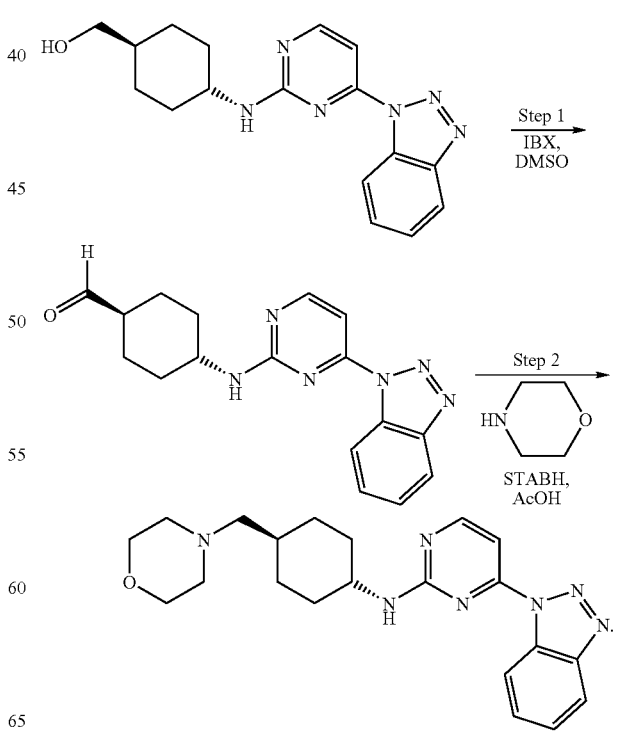

Step 1: Synthesis of 4-(4-benzotriazol-1-yl-pyrimidin-2-ylamino)-cyclohexanecarbaldehyde Iodoxybenzoic acid (830 mg, 2.96 mmol) was added to a solution of trans-[4-(4-benzo-triazol-1-yl-pyrimidin-2-ylamino)-cyclohexyl]-methanol (640 mg, 1.97 mmol) in DMSO (10 mL) and the resulting mixture was stirred at RT for 23 hours. An additional aliquot of o-iodoxy-benzoic acid (830 mg, 2.96 mmol) was then added. After a few hours, the reaction was stopped. Water was added and the resulting mixture was stirred for 20 minutes, the solid formed was filtered and the filtrate was extracted 3 times with EtOAc. The combined organic extracts were washed once with water, dried over $Na_2SO_4$ and filtered; the solvent was evaporated under reduced pressure. The white solid formed was washed several times with EtOAc and it was combined with the previous obtained solid to give 789 mg of crude residue. This crude material was purified via flash chromatography (heptane/EtOAc, with a gradient from 20% to 50% of EtOAc) to give 452 mg (70% yield) of 4-(4-benzotriazol-1-yl-pyrimidin-2-ylamino)-cyclo-hexanecarbaldehyde.

Step 2: Synthesis of (4-benzotriazol-1-yl-pyrimidin-2-yl)-(4-morpholin-4-ylmethyl-cyclohexyl)-amine A mixture of 4-(4-benzotriazol-1-yl-pyrimidin-2-ylamino)-cyclohexanecarbaldehyde (39 mg), morpholine (14 μL) and acetic acid (2 drops) in DCE (2 mL) was stirred at RT for 2 hours; sodium triacetoxyborohydride was then added. The resulting mixture was stirred for 3 hours at RT. Water was added; the organic layer was separated and washed 3 times with water. The aqueous layer was re-extracted with DCM. The combined organic extracts were dried over $Na_2SO_4$ and filtered; the solvent was evaporated under reduced pressure and the residue was purified via preparative TLC to afford 13.2 mg of (4-benzotriazol-1-yl-pyrimidin-2-yl)-(4-morpholin-4-ylmethyl-cyclohexyl)-amine. $^1$H NMR (400 MHz, $CDCl_3$) δ ppm 8.56 (1 H, d, J=8.31 Hz), 8.36-8.46 (1 H, bd), 8.12 (1 H, d, J=8.31 Hz), 7.55-7.69 (1 H, m), 7.40-7.52 (2H, m), 5.22-5.64 (1 H, m), 3.49-3.96 (5 H, m), 2.12-2.56 (6 H, m), 1.46-2.04 (5 H, m), 1.03-1.46 (4 H, m).

The following compounds were similarly prepared using the appropriate amine:

trans-4-[4-(4-Benzotriazol-1-yl-pyrimidin-2-ylamino)-cyclohexylmethyl]-piperazine-1-carboxylic acid tert-butyl ester. $^1$H NMR (400 MHz, $CDCl_3$) δ ppm 8.56 (1 H, d, J=8.43 Hz), 8.41 (1 H, bd), 8.12 (1 H, d, J=8.43 Hz), 7.61 (1 H, m), 7.43-7.51 (2H, m), 5.10-5.87 (1 H, m), 3.81-3.94 (1 H, m), 3.39-3.47 (4 H, m), 2.33-2.42 (3 H, m), 2.19-2.32 (4 H, m), 1.87-2.02 (2 H, m), 1.50-1.83 (2 H, m), 1.45 (9H, s), 1.05-1.41 (4 H, m); and trans-(4-Benzotriazol-1-yl-pyrimidin-2-yl)-{4-[(2-methoxy-ethylamino)-methyl]-cyclohexyl}-amine. $^1$H NMR (400 MHz, $CDCl_3$) δ ppm 8.56 (1 H, d, J=8.31 Hz), 8.38-8.45 (1 H, m), 8.12 (1 H, d, J=8.31 Hz), 7.61 (1 H, m), 7.42-7.50 (2 H, m), 5.17-5.64 (1 H, bd), 3.76-3.94 (1 H, m), 3.47-3.54 (2 H, m), 3.36 (3 H, s), 2.75-2.82 (2 H, m), 2.50-2.58 (2 H, m), 2.18-2.35 (1 H, m), 1.89-1.99 (1 H, m), 1.60-1.83 (4 H, m), 1.10-1.41 (4 H, m).

Example 23

Synthesis of trans-N-(4-Amino-cyclohexyl)-2-(4-methyl-piperazin-1-yl)-acetamide Synthesis of trans-N-(4-Amino-cyclohexyl)-2-(4-methyl-piperazin-1-yl)-acetamide was carried out according to the process shown in Scheme W.

SCHEME W

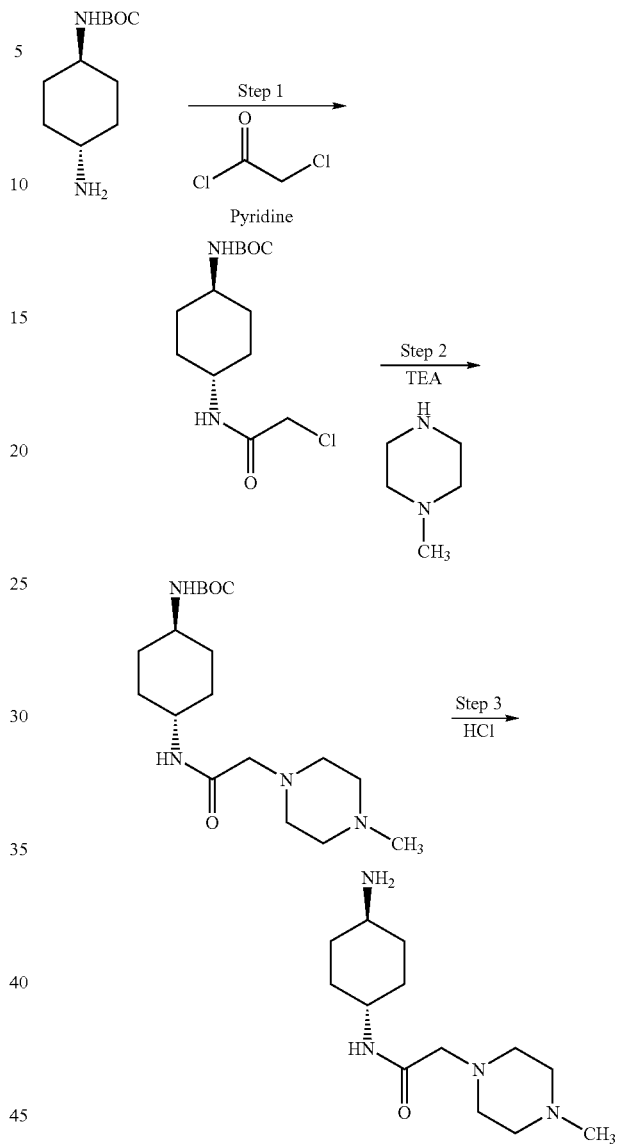

Step 1: Synthesis of trans-[4-(2-Chloro-acetylamino)-cyclohexyl]-carbamic acid tert-butyl ester To an ice-cooled solution of trans-4-methyl-cyclohexylamine (520 mg, 1.5 mmol) in DCM (15 mL) was added pyridine (0.36 mL, 4.5 mmol), followed by chloroacetyl chloride (1 equivalent) added dropwise. The mixture was allowed to warm up to RT and was stirred over 3 days. An additional aliquot of pyridine (1 equivalent) and chloroacetyl chloride (1 equivalent) was added and the resulting mixture was stirred overnight. The reaction mixture was diluted with EtOAc, washed with a saturated aqueous solution of $NaHCO_3$, extracted into EtOAc, and washed again with water. The combined organic layers were dried over $Na_2SO_4$, filtered and concentrated under reduced pressure to yield 478 mg of trans-[4-(2-chloro-acetylamino)-cyclo-hexyl]-carbamic acid tert-butyl ester without further purification.

Step 2: Synthesis of trans-{4-[2-(4-Methyl-piperazin-1-yl)-acetylamino]-cyclohexyl}-carbamic acid tert-butyl ester A solution of trans-[4-(2-chloro-acetylamino)-cyclohexyl]-carbamic acid tert-butyl ester (330 mg, 1.14 mmol) in DCM (12 mL) was added to a solution of methylpiperazine (0.1 mL, 0.95 mmol) in DCM (1 mL) at RT. The resulting mixture was allowed to stir overnight, then diluted with DCM, and washed with a saturated aqueous solution of NaHCO$_3$. The aqueous phase was extracted with DCM and then EtOAc. The combined organic phases were dried over Na$_2$SO$_4$, filtered and concentrated under reduced pressure to yield 199 mg of trans-{4-[2-(4-methyl-piperazin-1-yl)-acetylamino]-cyclohexyl}-carbamic acid tert-butyl ester without further purification.

Step 3: Synthesis of trans-N-(4-Amino-cyclohexyl)-2-(4-methyl-piperazin-1-yl)-acetamide An aqueous solution of HCl (2 M, 15 mL) was added to a solution of trans-{4-[2-(4-methyl-piperazin-1-yl)-acetylamino]-cyclohexyl}-carbamic acid tert-butyl ester (199 mg, 0.56 mmol) in MeOH (15 mL) at RT, and the resulting mixture was stirred overnight. The reaction mixture was concentrated under reduced pressure to give a solid residue. Et$_2$O was added to this material, and the resulting suspension was sonicated. The ether phase was decanted away, leaving a powdery brown solid which was purified by preparative TLC. The resulting oil was dissolved in the minimum quantity of MeOH, and Et$_2$O was added. A solid precipitated; the liquid phase was decanted away to give, after drying, 75 mg of trans-N-(4-amino-cyclohexyl)-2-(4-methyl-piperazin-1-yl)-acetamide as a fine powder.

In a similar manner, utilizing the appropriate starting materials, the following compounds were also prepared:
- trans-N-(4-Amino-cyclohexyl)-2-morpholin-4-yl-acetamide;
- trans-N-(4-Amino-cyclohexyl)-2-methoxy-acetamide; and
- trans-N-(4-Amino-cyclohexyl)-2-hydroxy-acetamide.

Example 24

Synthesis of trans-N-[4-(4-Benzotriazol-1-yl-pyrimidin-2-ylamino)-cyclohexyl]-2-methoxy-acetamide Synthesis of trans-N-[4-(4-Benzotriazol-1-yl-pyrimidin-2-ylamino)-cyclohexyl]-2-methoxy-acetamide was carried out according to the process shown in Scheme X.

SCHEME X

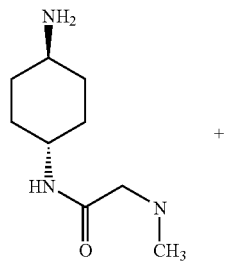

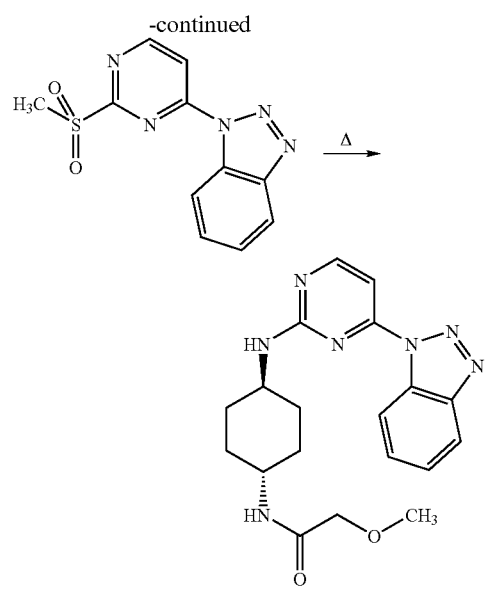

To a 10 mL sealable tube loaded with 1-(2-methanesulfonyl-pyrimidin-4-yl)-1H-benzotriazole (99.1 mg, 0.36 mmol) were added NMP (1 mL) and diisopropylethylamine (0.19 mL, 1.09 mmol). To a second 5 mL sealable tube loaded with N-(4-amino-cyclohexyl)-2-methoxy-acetamide (100 mg, 0.36 mmol) was added NMP (1 mL). Both tubes were heated at 120° C. and at complete dissolution of the solids the solution of 1-(2-methanesulfonyl-pyrimidin-4-yl)-1H-benzotriazole was transferred via cannula into the tube containing the solution of N-(4-amino-cyclohexyl)-2-methoxy-acetamide. The resulting mixture was stirred for 1.5 hours at 120° C., then cooled to RT and poured into water (15 mL). The resulting mixture was stirred overnight, then diluted with DCM and washed with water. The aqueous layer was separated and extracted with DCM. The combined organic layers were dried over Na$_2$SO$_4$, filtered and concentrated under reduced pressure to give an oil which was dissolved in a small amount of EtOAc and hexane was added to precipitate the solids. The resulting mixture was allowed to settle for 1 h, after which the liquid supernatant was carefully decanted away. The remaining solid was dried under reduced pressure to yield 86 mg (63% yield) of trans-N-[4-(4-benzotriazol-1-yl-pyrimidin-2-ylamino)-cyclohexyl]-2-methoxy-acetamide. MS=381 [M+H]$^+$; MP=233.5-235.4° C.

In a similar manner, utilizing the appropriate starting material, the following compounds were also prepared:
- trans-N-[4-(4-Benzotriazol-1-yl-pyrimidin-2-ylamino)-cyclohexyl]-2-hydroxy-acetamide, MS=368 [M+H]$^+$;
- trans-N-[4-(4-Benzotriazol-1-yl-pyrimidin-2-ylamino)-cyclohexyl]-2-morpholin-4-yl-acetamide, MS=437 [M+H]$^+$; and
- trans-N-[4-(4-Benzotriazol-1-yl-pyrimidin-2-ylamino)-cyclohexyl]-2-(4-methyl-piperazin-1-yl)-acetamide, MS=450 [M+H]$^+$.

Example 25

Synthesis of [3-(4-benzotriazol-1-ylpyrimidin-2-ylamino)-piperidin-1-yl]cyclo-propyl-methanone Step A: To NMP (10 mL) in a 20 mL vial was added 1-(2-methanesulfonyl-pyrimidin-4-yl)-1H-benzotriazole (1.1 g) and (S)—N—(BOC)-3-aminopiperidine (2 g), and the mixture heated at 90° C. for 2 h. The reaction mixture was then cooled to RT and quenched with water. The solid that separated was washed with water, then dried. The product, 3-(4-benzotriazol-1-yl-pyrimidin-2-ylamino)-N—BOC-piperidine, which was used without further purification.

Step B: To DCM (20 mL) was added HCl (20 mL, 2 N in MeOH) and 3-(4-benzotriazol-1-yl-pyrimidin-2-ylamino)-N—BOC-piperidine (1.0 g), and the mixture stirred at RT for 5 h. The reaction mixture was then concentrated, and the residue titurated with MeOH. The resulting solid was filtered and dried at 50° C. overnight under reduced pressure. The product, (4-benzotriazol-1-yl-pyrimidin-2-yl)-piperidin-3-ylamine, was used without further purification.

Step C: To DCM (8 mL) was added (4-benzotriazol-1-yl-pyrimidin-2-yl)-piperidin-3-ylamine (0.15 g), methanesulfonyl chloride (35 μL) and TEA (0.285 mL), and the mixture stirred at RT. The product was purified by column chromatography on silica, using 100% DCM to 15% MeOH/DCM, then recrystallized from EtOAc to provide (4-benzotriazol-1-yl-pyrimidin-2-yl)-(1-methanesulfonyl-piperidin-3-yl)-amine. Mp=196.0-197.0° C., $^1$H nmr (300 MHz, DMSO-d6): δ ppm 1.40-1.76 (m, 2H), 1.78-2.14 (m, 2H), 2.72-2.86 (m, 2H), 2.89 (s, 3H), 3.49 (m, 1H), 3.78 (m, 1H), 4.02 (m, 1H), 7.41 (d, J=5.27 Hz, 1H), 7.58 (t, J=7.35 Hz, 1H), 7.73 (m, 1H), 8.22 (d, J=8.29 Hz, 1H), 8.55 (d, J=5.27 Hz, 1H), 8.88 (d, 1H).

Step D: To DCM (8 mL) was added (4-benzotriazol-1-yl-pyrimidin-2-yl)-piperidin-3-ylamine (0.15 g), cyclopropylformyl chloride (40.5 μL) and TEA (0.285 mL), and the mixture stirred at RT. The product was purified by column chromatography on silica, using 100% DCM to 10% MeOH/DCM, then recrystallized from EtOAc to provide [3-(4-benzotriazol-1-yl-pyrimidin-2-ylamino)]-cyclopropylmethanone. Mp=99.0-100.0° C., $^1$H nmr (300 MHz, DMSO-d6): δ ppm 0.54-0.82 (m, 4H), 1.40-1.77 (m, 2H), 1.78-1.93 (m, 2H), 2.01-2.19 (m, 2H), 3.13 (t, J=11.11 Hz, 2H), 3.84-4.10 (m, 2H), 4.32 (d, J=11.68 Hz, 1H), 7.37 (d, J=5.27 Hz, 1H), 7.48-7.61 (m, 1H), 7.62-7.74 (m, 1H), 8.08-8.23 (d, 1H), 8.51 (d, J=5.27 Hz, 1H), 8.67 (d, J=8.29 Hz, 1H).

Step E: Similarly, proceeding as set forth in Steps A-D above, but substituting (R)—N—(BOC)-3-aminopiperidine for (S)—N—(BOC)-3-aminopiperidine, the corresponding optical isomers of (4-benzotriazol-1-yl-pyrimidin-2-yl)-(1-methanesulfonyl-piperidin-3-yl)-amine and [3-(4-benzotriazol-1-yl-pyrimidin-2-ylamino)]-cyclopropylmethanone were prepared. (4-Benzo-triazol-1-yl-pyrimidin-2-yl)-(1-methanesulfonyl-piperidin-3-yl)-amine: mp=196.0-197.0° C., $^1$H nmr (300 MHz, DMSO-d6): δ ppm 1.50-1.75 (m, 2H), 1.85-2.10 (m, 2H), 2.73-2.84 (m, 2H), 2.87 (s, 3H), 3.32-3.61 (m, 1H), 3.82 (m, J=11.30, 4.14 Hz, 1H), 4.06 (m, 1H), 7.39 (d, J=5.27 Hz, 4H), 7.49-7.62 (m, 1H), 7.64-7.78 (m, 2H), 8.17 (d, J=10.17 Hz, 1H), 8.53 (d, J=5.65 Hz, 1H), 8.67 (d, J=8.29 Hz, 1H). [3-(4-Benzotriazol-1-yl-pyrimidin-2-ylamino)]-cyclopropyl-methanone: mp=99.0-100.0° C., $^1$H nmr (300 MHz, DMSO-d6): δ ppm 0.43-0.68 (m, 2H), 0.67-0.83 (m, 2H), 1.44-1.78 (m, 2H), 1.77-1.94 (m, 2H), 2.01-2.19 (m, 1H), 3.13 (t, 2H), 3.75-4.16 (m, 2H), 4.32 (d, J=10.93 Hz, 1H), 7.25-7.45 (m, 1H), 7.55 (t, J=7.72 Hz, 1H), 7.63-7.78 (m, 1H), 8.17 (d, J=10.17 Hz, 1H), 8.51 (d, J=5.27 Hz, 1H), 8.67 (d, J=8.29 Hz, 1H).

Step F: To NMP (3 mL) was added 1-(2-methanesulfonyl-pyrimidin-4-yl)-1H-benzo-triazole (0.2 g) and N-(4-aminocyclohexyl)-N-(2-TBSO-ethyl)-methanesulfonamide (0.636 g), and the reaction stirred at 85° C. until reaction was complete. The reaction mixture was cooled to RT, quenched with water, and purified by column chromatography using 100% DCM to 10% MeOH/DCM. The product (~0.2 g) was de-protected by stirring with TBAF/THF (1.5 mL, 1.0 M in THF) in THF (1.5 mL) for 5 h at RT. The product was quenched with water, and the solid that separated was filtered, washed with water, and dried at 50° C. under reduced pressure to provide N-[4-(4-benzotriazol-1-yl-pyrimidin-2-ylamino)-cyclohexyl]-N-(2-hydroxyethyl)-methane-sulfonamide. Mp=230.0-231.0° C. $^1$H nmr (300 MHz, DMSO-d6): δ ppm 1.23-1.58 (m, 2H), 1.67-1.94 (m, 2H), 2.13 (d, J=12.81 Hz, 2H), 2.94 (s, 3H), 3.24 (t, J=6.59 Hz, 2H), 3.46-3/67 (m, 2H), 3.69-3.92 (m, 1H), 4.45 (br. S., 1H), 7.31 (d, 1H), 7.33-7.41 (m, 1H), 7.48-7.61 (m, 1H), 7.65-7.82 (m, 1H), 8.17 (d, J=8.29 Hz, 1H), 8.48 (d, J=5.65 Hz, 1H), 8.69 (d, J=8.67 Hz, 1H).

Example 26

Formulations

Pharmaceutical preparations for delivery by various routes are formulated as shown in the following Tables. "Active ingredient" or "Active compound" as used in the Tables means one or more of the Compounds of Formula I.

| Composition for Oral Administration | |
| --- | --- |
| Ingredient | % wt./wt. |
| Active ingredient | 20.0% |
| Lactose | 79.5% |
| Magnesium stearate | 0.5% |

The ingredients are mixed and dispensed into capsules containing about 100 mg each; one capsule would approximate a total daily dosage.

| Composition for Oral Administration | |
| --- | --- |
| Ingredient | % wt./wt. |
| Active ingredient | 20.0% |
| Magnesium stearate | 0.5% |
| Crosscarmellose sodium | 2.0% |
| Lactose | 76.5% |
| PVP (polyvinylpyrrolidine) | 1.0% |

The ingredients are combined and granulated using a solvent such as methanol. The formulation is then dried and formed into tablets (containing about 20 mg of active compound) with an appropriate tablet machine.

| Composition for Oral Administration | |
| --- | --- |
| Ingredient | Amount |
| Active compound | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum K (Vanderbilt Co.) | 1.0 g |
| Flavoring | 0.035 ml |
| Colorings | 0.5 mg |
| Distilled water | q.s. to 100 ml |

The ingredients are mixed to form a suspension for oral administration.

| Parenteral Formulation | |
|---|---|
| Ingredient | % wt./wt. |
| Active ingredient | 0.25 g |
| Sodium Chloride | qs to make isotonic |
| Water for injection | 100 ml |

The active ingredient is dissolved in a portion of the water for injection. A sufficient quantity of sodium chloride is then added with stirring to make the solution isotonic. The solution is made up to weight with the remainder of the water for injection, filtered through a 0.2 micron membrane filter and packaged under sterile conditions.

| Suppository Formulation | |
|---|---|
| Ingredient | % wt./wt. |
| Active ingredient | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

| Topical Formulation | |
|---|---|
| Ingredients | grams |
| Active compound | 0.2-2 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water | q.s. 100 |

All of the ingredients, except water, are combined and heated to about 60° C. with stirring. A sufficient quantity of water at about 60° C. is then added with vigorous stirring to emulsify the ingredients, and water then added q.s. about 100 g.

Example 27

Nasal Spray Formulations

Several aqueous suspensions containing from about 0.025-0.5 percent active compound are prepared as nasal spray formulations. The formulations optionally contain inactive ingredients such as, for example, microcrystalline cellulose, sodium carboxymethylcellulose, dextrose, and the like. Hydrochloric acid may be added to adjust pH. The nasal spray formulations may be delivered via a nasal spray metered pump typically delivering about 50-100 microliters of formulation per actuation. A typical dosing schedule is 2-4 sprays every 4-12 hours.

Example 28

Kinase Assays

A: IC$_{50}$ Measurement

To determine inhibition of Cdk4, Cdk2 and Cdk1 activity, kinase assays were conducted using FlashPlate™ assays (NEN™-Life Science Products). FlashPlate assays were performed using recombinant human cyclin B-CDK1, human cyclin E-CDK2 or human cyclin D1-CDK4 complexes. GST-cyclinE (GST-cycE), CDK2, GST-cyclinB (GST-cycB), CDK1, GST-CDK4 and cyclin D1 (cycD1) cDNA clones in baculovirus vectors were provided by Dr. W. Harper at the Baylor College of Medicine, Houston, Tex. Proteins were co-expressed in High Five™ insect cells and the complex was purified on glutathione Sepharose® resin (Pharmacia, Piscataway, N.J.) as previously described (J. W. Harper et al., *Cell* (1993) 75:805-16). A 6×-Histidine tagged truncated form of retinoblastoma (Rb) protein (amino acids 386-928) was used as the substrate for the cycD1-CDK4, cycB-CDK1 and the cycE-CDK2 assays (the expression plasmid was provided by Dr. Veronica Sullivan, Department of Molecular Virology, Roche Research Centre, Welwyn Garden City, United Kingdom). The Rb protein is a natural substrate for phosphorylation by CDK4, CDK2 and CDK1 (see Herwig and Strauss *Eur. J. Biochem.* (1997) 246:581-601 and the references cited therein).

The expression of the 62 Kd protein was under the control of an IPTG inducible promoter in an M15 *E. coli* strain. Cells were lysed by sonication and purification was carried out by binding lysates at pH 8.0 to a Ni-chelated agarose column pretreated with 1 mM imidazole. The resin was then washed several times with incrementally decreasing pH buffers to pH 6.0, and eluted with 500 mM imidazole. Eluted protein was dialysed against 20 mM HEPES pH 7.5, 30% glycerol, 200 mM NaCl, and 1 mM DTT. Purified Rb fusion protein stocks were quantitated for protein concentration, aliquoted, and stored at −70° C.

For all three kinase assays reported herein, 96-well Flash-Plates were coated with Rb protein at 10 µg/ml, using 100 µl per well. Plates were incubated at 4° C. overnight or at RT for 3 hours on a shaker. To control for nonspecific phosphorylation, one row of wells was coated with 100 µl/well coating buffer (20 mM HEPES, 0.2 M NaCl). Plates were then washed twice with wash buffer (0.01% Tween® 20 in phosphate-buffered saline). Compounds to be tested ("test compounds") were added to the wells at 5× final concentration. Reactions were initiated by immediate addition of 40 µl reaction mix (25 mM HEPES, 20 mM MgCl$_2$, 0.002% Tween 20, 2 mM DTT, 1 µM ATP, 4 nM $^{33}$P-ATP) and a sufficient amount of enzyme to give counts that were at least 10-fold above background. Plates were incubated at RT on a shaker for 30 minutes. Plates were washed four times with the wash buffer, sealed, and counted on the TopCount scintillation counter (Packard Instrument Co., Downers Grove, Ill.]. The percent inhibition of Rb phosphorylation, which is a measure of the inhibition of CDK activity, was determined according to the following formula:

$$100 \times \left(1 - \frac{\text{test compound} - \text{nonspecific}}{\text{total} - \text{nonspecific}}\right)$$

where "test compound" refers to the average counts per minute of the test duplicates, "nonspecific" refers to the average counts per minute when no CyclinD/Cdk4, etc., was added, and "total" refers to the average counts per minute when no compound was added. The IC$_{50}$ value is the concentration of test compound that reduces by 50% the protein-kinase induced incorporation of the radiolabel under the test conditions described.

B. $K_i$ Measurement

Alternatively, inhibition activity may be measured using Ki. Using the protein constructs described above in Example 28(A) above, CDK1, CDK2, and CDK4 HTRF assays were set up. These were done in 96-well format and read in 384-well plate format. The assays were run at 3× their respective Kms for ATP.

In the CDK4 assay, test compounds were diluted to 3× their final concentrations in 25 mM Hepes, pH 7.0, 6.25 mM $MgCl_2$, 1.5 mM DTT, 135 µM ATP. The DMSO concentration was no greater than 4.76%. Twenty microliters were added to the wells of a 96-well plate. The kinase reaction was initiated by the addition of 40 µl/well of a solution containing 0.185 µM Rb and 2.25 µg/ml CDK4 in 25 mM HEPES, pH 7.0, 6.25 mM $MgCl_2$, 0.003% Tween-20, 0.3 mg/ml BSA, 1.5 mM DTT. Blank wells without CDK4 were included. The plates were incubated at 37° C. for 30 minutes with shaking. The kinase reaction was terminated by the addition of 15 µl/well of 1.6 µM anti-phospho-Rb (Ser 780) antibody (Cell Signaling Inc.) in 25 mM HEPES, pH 7.0, 24 mM EDTA, 0.2 mg/ml BSA. After 30 minutes at 37° C., 15 µl/well of 3 nM Lance-Eu-W1024 labeled anti-rabbit IgG and 60 nM Allophycocyanin conjugated anti-His6 (PerkinElmer Life Sciences) in 25 mM Hepes, pH 7.0, 0.5 mg/ml BSA were added. Following a one hour incubation at 37° C., 35 µl of each well, in duplicate, were transferred to 384-well black plates. The plates were read using either ViewLux or Victor V readers (PerkinElmer Life Sciences) using an excitation wavelength of 340 nm and dual emission wavelengths of 615 nm and 665 nm. IC50 values (the concentration of test compounds reducing the assay control fluorescence read-out by 50%) were first calculated from net readings at 665 nm, normalized for europium readings at 615 nm. For ATP competitive inhibitors, the Ki values were calculated according to the following equation:

$Ki=IC50/(1+S/Km)$ where S refers to the substrate concentration and Km refers to the Michaelis-Menten constant.

The CDK1 and CDK2 assays were similarly run except for small differences in reagent and protein concentrations:

The compound and enzyme buffers for both assays contained 10 mM $MgCl_2$. For CDK1 and CDK2, the respective reagent ATP concentrations were 162 µM and 90 µM. CDK1 at a reagent concentration of 0.15 ng/µl and CDK2 at a reagent concentration of 0.06 ng/µl were used. Reagent concentrations of detection reagents were adjusted between 3-12 nM Eu-Ab and 60-90 nM APC-antiHis 6 to give signal to background ratios of at least 10 to 1.

Example 29

Cell Based Assays (Tetrazolium dye proliferation assay) ("MTT Assay")

Proliferation was evaluated by the tetrazolium dye assay according to the procedure of Denizot and Lang (F. Denizot and R. Lang, *J Immunol Meth* (1986) 89:271-77). The cell line used was HCT116, a colorectal carcinoma cell line obtained from the American Type Cell Culture Collection (ATCC; Rockville, Md.). The cells were grown in McCoy's 5A medium supplemented with 10% FCS and L-glutamine.

Cells were plated at the appropriate seeding density to give logarithmic growth over the course of the assay in a 96-well tissue culture plate. Plates were incubated overnight at 37° C. in a humidified incubator with 5% $CO_2$. The next day, test compounds were serially diluted to four times the final concentration in the appropriate medium containing 1.2% DMSO. One-fourth final volume of each dilution was added in duplicate to the plates containing cells. The same volume of 1.2% DMSO in medium was added to a row of "control wells" such that the final concentration of DMSO in each well was 0.3%. Wells to which no cells were added served as the "blank." Wells to which no inhibitor was added served as "no inhibitor control." The plates were returned to the incubator, and at set time points (determined by their growth curves) plates were analyzed as described below.

3-(4,5-dimethylthiazole-2-yl)-2,5-diphenyl-2H-tetrazolium bromide (thiazolyl blue; MTT; Sigma) was added to each well to yield a final concentration of 1 mg/ml. Plates were returned to the incubator for 2.5-3 hours at 37° C. The MTT-containing medium was removed and the resulting formazan metabolite was solubilized in 100% ethanol with shaking for 15 minutes at RT. Absorbance readings were taken in a microtiter plate reader (Dynatech and Molecular Devices plate readers were used interchangeably) at a wavelength of 570 nm with a 650 nm reference. Percent inhibition (% INH) is calculated by subtracting the absorbance of the blank well from all wells, then subtracting the ratio of the average absorbance of each test duplicate ($S_{AVE}$) by the average of the controls ($C_{AVE}$) from 1.00. The final number is then multiplied by 100 (% INH=$(1.00-S_{AVE}/C_{AVE})\times100$). The concentration at which 90% inhibition of cell proliferation is obtained (the $IC_{90}$) is determined from the linear regression of a plot of the logarithm of the concentration versus percent inhibition.

SW1353 cells purchased from American Tissue Culture Collection (ATCC) are grown in a 6-well plate at a density of $3\times10^5$ cells per well containing 2 ml of Dulbecco's modified Eagle's medium (Invitrogen) supplemented with 10% fetal bovine serum (Invitrogen) until confluency at 37° C. Cells are then placed with serum-free medium for 2 hrs at 37° C. Compound stock (10 mM) is diluted in dimethylsulfoxide (DMSO) and added to each well as a 1000× concentrated solution in a volume of 3 µl, mixed and preincubated with cells for 30 minutes. The compound vehicle DMSO is maintained at a final concentration of 0.3% in all samples. TNF (Roche Biochem) is added as a 10× concentrated solution made up in growth media and added in a volume of 30 µl per well with a final concentration of 1 ng/ml in a total volume of 300 µl serum-free medium. Cell plates are then incubated for 20 minutes at 37° C. After the removal of cell media, the cell lysates are collected in 120 µl of lysis buffer (Biosource). Protein concentrations for the lysate samples are determined by Lowry assay according to manufacturer's (Bio-Rad) instruction.

Cell lysate samples (15 µg of total proteins per sample) are loaded on 10% NuPAGE Bis-Tris gel (Invitrogen) and transferred to nitrocellulose membrane (Invitrogen). The membrane is blocked in 5% dry milk in 1×TBS for 1 hour at RT. To determine the levels of both phosphorylated and total cJun in the samples, the membrane is simultaneously probed with rabbit anti-p-cjun and mouse anti-total cJun antibodies (Cell Signaling) in Odyssey blocking buffer (Li-cor) with 0.1% Tween 20 (Roche Biochem) for overnight at 4° C.

The membrane is washed 3 times in 1×PBS with 0.1% Tween® 20. As the secondary antibodies, IRDye 700 goat anti-mouse IgG (Rockland) and IRDye 800 goat anti-rabbit IgG (Rockland) are used in a dilution of 1:6500 in Odyssey blocking buffer. The membrane Blot is scanned and quantified using the Odyssey Infrared Imager (Li-cor Cat. No. 9201).

The normalized intensities of p-c-Jun vs total c-Jun are used for $IC_{50}$ calculation with the Xlfit3 program of Microsoft Excel. The $IC_{50}$ value is interpolated from a graph of inhibitor concentration vs. percent inhibition.

Example 30

JNK Assay In Vitro

JNK activity is measured by phosphorylation of GST-ATF2 (19-96) with [γ-$^{33}$P] ATP. The enzyme reaction is conducted at Km concentrations of ATP and the substrate at final volume of 40 µl in buffer containing 25 mM Hepes, pH 7.5, 2 mM dithiothreitol, 150 mM NaCl, 20 mM MgCl$_2$, 0.001% Tween® 20, 0.1% BSA and 10% DMSO. Human JNK2α2 assay contains 1 nM enzyme, 1 µM ATF2, 8 µM ATP with 1 uCi [γ-$^{33}$P] ATP. Human JNK1α1 assay contains 2 nM enzyme, 1 µM ATF2, 6 µM ATP with 1 µCi [γ-$^{33}$P] ATP. Human JNK3 (Upstate Biotech #14-501 M) assay contains 2 nM enzyme, 1 µM ATF2, 4 µM ATP with 1 µCi [γ-$^{33}$P] ATP. The enzyme assay is carried out in the presence or absence of ten compound concentrations. JNK and compound are pre-incubated for 10 minutes. Then, the enzymatic reaction is initiated by addition of ATP and the substrate. The reaction mixture is incubated at 30° C. for 30 minutes. At the end of incubation, the reaction is terminated by transferring 25 µl of the reaction mixture to 150 µl of 10% glutathione sepharose slurry (Amersham #27-4574-01) containing 135 mM EDTA. The reaction product is captured on the affinity resin and washed on a filtration plate (Millipore, MABVNOB50) with phosphate buffered saline for six times to remove free radio nucleotide. Then the incorporation of $^{33}$P into ATF2 is quantified on a microplate scintillation counter (Packard Topcount). Compound inhibition potency on JNK is measured by IC$_{50}$ value generated from ten concentration inhibition curve fitted into the 3-parameter model: % inhibition=Maximum/$(1+(IC_{50}/[Inhibitor])^{slope})$. Data are analyzed on Microsoft Excel for parameter estimation.

Example 31

Rat In Vivo TNFα-Induced IL-6 Production Assay

Female Wistar-Han rats procured from Charles River Laboratories are allowed to acclimate for one week prior to use and achieve an approximate body weight of 95-130 g. Rats are administered test compound via oral gavage, subcutaneous injection or intravenous injection (tail vein) 30 min prior to an intra-peritoneal challenge of 0.5 µg recombinant rat TNF-α (Biosource). Blood is collected via cardiocentesis 90 min after TNF-α challenge. Plasma is prepared using lithium heparin separation tubes (BD microtainer) and frozen at −80° C. until analyzed. IL-6 levels are determined using a rat specific IL-6 ELISA kit (Biosource). The percent inhibition and ED$_{50}$ values (calculated as the dose of compound at which TNF-α production is 50% of the control value) are determined.

Example 32

Rodent Collagen-Induced Arthritis

Female Lewis rats procured from Harlan Laboratories at 7-8 weeks of age are allowed to acclimate for one week prior to use and achieve an approximate body weight of 120-140 g. On day 0 of study, rats are primed intradermally (i.d.) on several sites on the back with an emulsion of 100 µg Bovine Type II Collagen (Chondrex) in Incomplete Freund's adjuvant (IFA; total of 0.1 ml in 2-3 sites). Arthritis induction is generally observed 12-14 days from priming; however a booster injection of 100 µg collagen/IFA is given around days 7-10 (i.d. up to 0.1 ml total) at base of tail or an alternate site on back to synchronize disease induction. Compound dosing can be prophylactic (starting at time of boost or 1-2 days prior) or therapeutic (beginning after boost and coinciding with initial disease scores of 1-2—see clinical scoring below). Animals are evaluated for the development and progression of disease over the next 21 days.

Rats are evaluated using a scoring system (described below), paw volume measurements using a plethysmometer for each paw, or measuring paw or joint thickness with a caliper. Baseline measurements are performed on day 0 and starting again at the first signs or swelling for up to three times per week until the end of the experiment. Scoring was evaluated as follows for each paw:

1=swelling and/or redness of paw or one digit.

2=swelling in two or more joints.

3=gross swelling of the paw with more than two joints involved.

4=severe arthritis of the entire paw and digits.

The arthritic index for each rat was evaluated by adding the four scores of the individual paws, giving a maximum score of 16. In order to serially measure disease onset and progression, the paw volume of the hind paws is also determined through the use of a plethysmometer.

At the end of the study, the hind paws (and other tissues) are harvested for weight determination, histology, cellular and/or molecular analysis. Additionally, blood is collected via cardiocentesis, plasma is prepared using lithium heparin separation tubes (BD microtainer) and frozen at −80° C. until analyzed. Inflammatory cytokine levels (e.g., TNF-α, IL-1 and IL-6) from the plasma or from homogenized joint tissue are determined using rat-specific ELISA kits (R&D). The level of disease protection or inhibition is determined as a composite of changes in clinical scores, paw volumes and histopathology compared to control animals.

Example 33

IL-8 Production Assay in TNFα-Induced Human Chondrosarcoma SW1353 Cells

SW1353 cells are purchased from the American Tissue Culture Collection and maintained in growth media consisting of DMEM medium (Invitrogen) with 10% fetal bovine serum (Invitrogen), ascorbic acids (Sigma) and penicillin (Invitrogen) under the culture condition of 37° C. in 5% CO$_2$. Cells are plated at a density of 1.0×10$^4$ cells per well in 100 µl of media 48 hours before the compound treatment. Immediately before the compound treatment, media is replaced with 160 µl of fresh media. Compound stock (10 mM) is diluted in growth media and added to each well as a 10× concentrated solution in a volume of 20 µl, mixed and allowed to pre-incubate with cells for 30 minutes. The compound vehicle (DMSO) is maintained at a final concentration of 1% in all samples. After 30 minutes the cells are activated with 10 ng/ml of TNF-α (Roche Biochem). TNF-α is added as a 10× concentrated solution made up in growth media and added in a volume of 20 µl per well. Cell plates are cultured for 5 hours. Cell media are harvested and stored at −20° C. Media aliquots are analyzed by sandwich ELISA for the presence of IL-8 as per the manufacturer's instructions (BD Bioscience). The IC$_{50}$ values are calculated as the concentration of the compound at which the IL-8 production was reduced to 50% of the control value using Xlfit3 in Microsoft Excel program. Certain compounds have an IC$_{50}$ value ranging from 0.1-20 µM in this assay.

What is claimed:
1. A compound of the formula:

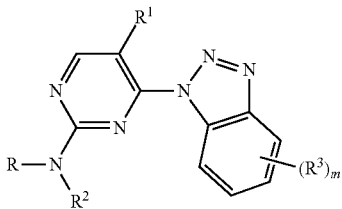

or a pharmaceutically acceptable salt thereof,
wherein
R is lower alkyl, hydroxy lower alkyl, or a radical selected from:

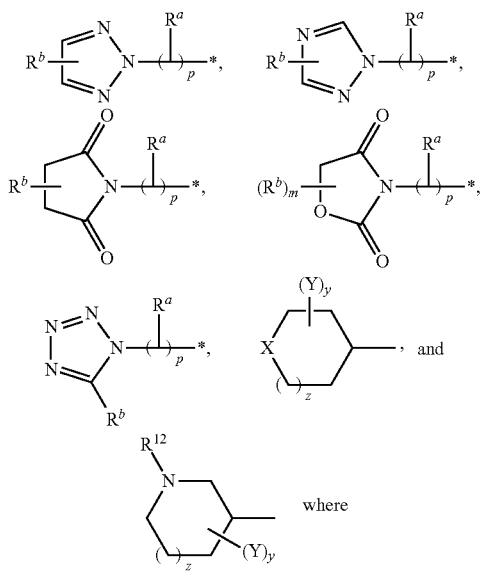

where each $R^a$ is independently H, lower alkyl, OH, or hydroxy-lower alkyl;
each $R^b$ is independently H, lower alkyl, halo, nitro, or halo-lower alkyl;
p is 1, 2, 3, or 4;
X is O, $CR^4R^5$, C(=O), or $S(O)_x$;
$R^1$ is hydrogen, halo, alkyl, or $NH_2$;
each of $R^3$ is independently halo, $-NO_2$, lower alkyl, $-CN$, $-OR^7$, $-NR^8R^9$, $-C(O)-R^7$, $-O-C(O)R^7$, $-CF_3$, $-CHF_2$, $-SO_2-R^{10}$, or two of $R^3$ form alkylene dioxy;
$R^4$ is hydrogen, lower alkyl, cyano, $-(CH_2)_nOR^7$, $-(CH_2)_nNR^8R^9$, $-(CH_2)_n-C(O)-NR^8R^9$, $-(CH_2)_n-OC(O)NR^8R^9$, $-(CH_2)_n-C(O)-OR^7$; $-NR^7-SO_2-R^{10}$, $-(CH_2)_n-NR^8-C(O)-R^{11}$, or $-(CH_2)_n-NR^8-C(O)-OR^6$;
$R^5$ is hydrogen or alkyl;
or $R^4$ and $R^5$ together form alkylene dioxy;
$R^6$ is hydrogen, lower alkyl, heteroalkyl, cycloalkyl, heterocyclylalkyl, or $-NR^8R^9$;
$R^{10}$ is alkyl, cycloalkyl, heterocyclylalkyl, or $-NR^8R^9$;
$R^{11}$ is alkyl, cycloalkyl, heteroalkyl, or (heterocyclyl)alkyl;
$R^2$ and $R^7$ are each independently hydrogen, lower alkyl, hydroxyalkyl, or cycloalkyl;
$R^8$ is hydrogen, lower alkyl, or acyl;
$R^9$ is hydrogen, lower alkyl, heteroalkyl, aryl, heteroaryl, heterocyclyl, cycloalkyl;
or $R^8$ and $R^9$ together with the nitrogen atom to which they are connected to form a heterocyclyl comprising at least one nitrogen ring atom, optionally substituted with OH, oxo, lower alkyl, lower alkoxy, or acyl;
$R^{12}$ is H, lower alkyl, cycloalkyl, $-C(O)-R^7$, $-SO_2-R^{11}$;
each of m and x is independently an integer from 0 to 2;
Y is hydrogen, $-(CH_2)_n-OR^7$, $-(CH_2)_n-C(O)-R^7$ or $-(CH_2)_n-C(O)OR^7$;
each of y and z is independently 0 or 1; and
n is an integer from 0 to 4.

2. The compound of claim 1, wherein $R^2$ is hydrogen or methyl.
3. The compound of claim 2, wherein m is 0.
4. The compound of claim 3, wherein $R^1$ is hydrogen, methyl, chloro, or fluoro.
5. The compound of claim 1, wherein X is $CR^4R^5$.
6. The compound of claim 5, wherein $R^5$ is hydrogen or methyl.
7. The compound of claim 5, wherein z is 1, and $R^4$ is $-NR^7-SO_2-R^{10}$.
8. The compound of claim 7, wherein $R^7$ is hydrogen or methyl, and $R^{10}$ is methyl, ethyl, or $-N(CH_3)_2$.
9. The compound of claim 5, wherein z is 1, and $R^4$ is hydrogen, lower alkyl, cyano, $-(CH_2)_nOR^7$, or $-(CH_2)_nNR^8R^9$, or $R^4$ and $R^5$ together form alkylene dioxy.
10. The compound of claim 9, wherein $R^4$ is $-(CH_2)_nOR^7$, n is 0 or 1, and $R^7$ is hydrogen or methyl.
11. The compound of claim 9, wherein $R^4$ is $-(CH_2)_nNR^8R^9$.
12. The compound of claim 11, wherein n is 0 and $R^8$ is hydrogen, and $R^9$ is hydrogen, pyrimidin-2-yl, or pyridin-2-yl.
13. The compound of claim 11, wherein n is 0 and $R^8$ and $R^9$ together with the nitrogen atom to which they are connected to form 2,5-dioxo-pyrrolidin-1-yl.
14. The compound of claim 9, wherein $R^4$ is hydrogen, methyl, ethyl, or cyano.
15. The compound of claim 9, wherein $R^4$ and $R^5$ together form ethylene dioxy.
16. The compound of claim 5, wherein z is 1, and $R^4$ is $-(CH_2)_n-NR^8-C(O)R^{11}$, wherein n, $R^8$, and $R^{11}$ are those defined in claim 1.
17. The compound of claim 16, wherein n is 0, $R^8$ is hydrogen or methyl, and $R^{11}$ is methyl, ethyl, methoxymethyl, hydroxymethyl, (morpholin-4-yl)methyl, or (4-methyl-piperazin-l-yl)methyl.
18. The compound of claim 5, wherein z is 1, and $R^4$ is $-(CH_2)_n-C(O)-NR^8R^9$.
19. The compound of claim 18, wherein n is 0, and $R^8$ and $R^9$ together with the nitrogen atom to which they are connected to form morpholin-4-yl, pyrrolidin-1-yl, or 4-methyl-piperazin-1-yl.
20. The compound of claim 18, wherein n is 0, and $R^8$ is hydrogen or methyl, and $R^9$ is (2-amino-2-methyl)propyl, (2-hydroxy)ethyl, tetrahydropyran-4-yl, cyclopropyl, or ethyl.
21. The compound of claim 5, wherein z is 1, and $R^4$ is $-(CH_2)_n-C(O)-OR^7$.
22. The compound of claim 21, wherein n is 0 and $R^7$ is hydrogen or methyl.
23. The compound of claim 5, wherein $R^4$ and $R^5$ are hydrogen, z is 0, y is 1, and Y is hydroxy on the 3-position of the cyclopentyl ring moiety.

24. The compound of claim 5, wherein $R^4$ and $R^5$ are hydrogen, z is 1, y is 1, and Y is hydroxy, hydroxymethyl, or —$CO_2CH_2CH_3$ group on the 2-position of the cyclohexyl ring moiety.

25. The compound of claim 1, wherein z is 1, and X is O, C(=O,), or $SO_2$.

26. The compound of claim 4, wherein R is

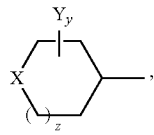

z is 1, and X is O or $CR^4R^5$.

27. The compound of claim 26, wherein X is O.

28. The compound of claim 26, wherein X is $CR^4R^5$.

29. The compound of claim 28, wherein R4 is —OH, —$OR^7$, —$C(O)NR^8R^9$, —$NR^8R^9$, or —$NR^7SO_2R^{10}$.

30. A composition comprising a compound of claim 1 and a pharmaceutically acceptable excipient.

31. A method for treating rheumatoid arthritis, comprising administering to a patient a therapeutically effective amount of a compound of claim 1.

32. The compound of claim 1, wherein R is a radical selected from:

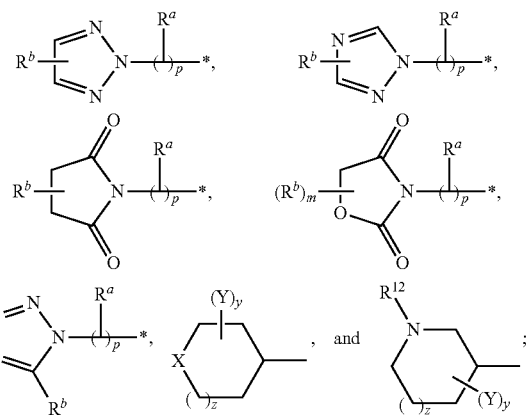

and wherein m, p, y, z, X, Y, $R^a$ and $R^b$ are as recited in claim 1.

* * * * *